US011183640B2

(12) United States Patent
Cho et al.

(10) Patent No.: US 11,183,640 B2
(45) Date of Patent: Nov. 23, 2021

(54) ORGANIC ELECTROLUMINESCENT DEVICE COMPRISING ELECTRONTRANSPORT LAYER AND ELECTRON BUFFER LAYER

(71) Applicant: ROHM AND HAAS ELECTRONIC MATERIALS KOREA LTD, Chungcheongnam-do (KR)

(72) Inventors: Sang-Hee Cho, Gyeonggi-do (KR); Doo-Hyeon Moon, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 461 days.

(21) Appl. No.: 16/331,541

(22) PCT Filed: Sep. 22, 2017

(86) PCT No.: PCT/KR2017/010483
§ 371 (c)(1),
(2) Date: Mar. 8, 2019

(87) PCT Pub. No.: WO2018/062778
PCT Pub. Date: Apr. 5, 2018

(65) Prior Publication Data

US 2019/0214572 A1 Jul. 11, 2019

(30) Foreign Application Priority Data

Sep. 29, 2016 (KR) ........................ 10-2016-0125799

(51) Int. Cl.
*H01L 51/50* (2006.01)
*H01L 51/00* (2006.01)
(Continued)

(52) U.S. Cl.
CPC ........ *H01L 51/0067* (2013.01); *C07D 403/10* (2013.01); *C07D 413/10* (2013.01);
(Continued)

(58) Field of Classification Search
None
See application file for complete search history.

(56) References Cited

U.S. PATENT DOCUMENTS 9,732,099 B1 8/2017 Jun et al.
2010/0200054 A1 8/2010 Mi-Young et al.
(Continued)

FOREIGN PATENT DOCUMENTS

KR 2009-0073852 A 7/2009
KR 2010-0118690 A 11/2010
(Continued)

OTHER PUBLICATIONS

Search Report for Chinese Patent Application No. 201780055496.4; dated Sep. 22, 2017.

*Primary Examiner* — Gregory D Clark
(74) *Attorney, Agent, or Firm* — G. Creston Campbell

(57) ABSTRACT

The present disclosure relates to an organic electroluminescent device comprising a first electrode, a second electrode facing the first electrode, a light-emitting layer between the first electrode and the second electrode, and an electron transport layer and an electron buffer layer between the light-emitting layer and the second electrode. An organic electroluminescent device having low driving voltage, high luminous efficiency and/or long lifespan can be provided by comprising the compound of the present disclosure in an electron buffer layer and an electron transport layer.

10 Claims, 2 Drawing Sheets

(51) Int. Cl.

| | |
|---|---|
| ***C09K 11/06*** | (2006.01) |
| ***C07D 403/10*** | (2006.01) |
| ***C07D 413/10*** | (2006.01) |

(52) U.S. Cl.

CPC .......... *C09K 11/06* (2013.01); *H01L 51/0071* (2013.01); *H01L 51/0072* (2013.01); *H01L 51/0077* (2013.01); *H01L 51/5004* (2013.01); *H01L 51/508* (2013.01); *H01L 51/5012* (2013.01); *H01L 51/5076* (2013.01); *H01L 2251/552* (2013.01)

(56) References Cited

U.S. PATENT DOCUMENTS

| | | | |
|---|---|---|---|
| 2017/0047524 | A1 | 2/2017 | Kim et al. |
| 2017/0077415 | A1 | 3/2017 | Kim et al. |
| 2017/0117485 | A1 | 4/2017 | Cho et al. |
| 2017/0207398 | A1 | 7/2017 | Yang et al. |

FOREIGN PATENT DOCUMENTS

| | | | | |
|---|---|---|---|---|
| KR | 2014-0138393 A | | 12/2014 | |
| KR | 2015-0002072 A | | 1/2015 | |
| KR | 2015002072 | * | 1/2015 | ............. H01L 51/50 |
| KR | 2015-0080213 A | | 7/2015 | |
| WO | 2017/156698 A | | 9/2017 | |

* cited by examiner

ORGANIC ELECTROLUMINESCENT DEVICE COMPRISING ELECTRONTRANSPORT LAYER AND ELECTRON BUFFER LAYER

TECHNICAL FIELD

The present disclosure relates to an organic electroluminescent device comprising an electron transport layer and an electron buffer layer.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic EL device (OLED) changes electric energy into light by applying electricity to an organic electroluminescent material, and commonly comprises an anode, a cathode, and an organic layer formed between the two electrodes. The organic layer of the organic EL device may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc., if necessary. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on their functions. In the organic EL device, holes from the anode and electrons from the cathode are injected into a light-emitting layer by the application of electric voltage, and excitons having high energy are produced by the recombination of the holes and electrons. The organic light-emitting compound moves into an excited state by the energy and emits light from an energy when the organic light-emitting compound returns to the ground state from the excited state.

In an organic EL device, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Also, an electron buffer layer is equipped to improve a problem of light-emitting luminance reduction which may occur due to the change of current properties in the device when the device is exposed to a high temperature during a process of producing panels. Thus, the properties of the compounds comprised in the electron buffer layer are important. In addition, the compound used in the electron buffer layer is desirable to perform a role of controlling an electron injection by the electron withdrawing characteristics and the electron affinity LUMO (lowest unoccupied molecular orbital) energy level, and thus may perform a role to improve the efficiency and the lifespan of the organic electroluminescent device.

Korean Patent Application Laid-Open No. 2015-0080213 discloses a combination of an anthracene-based compound and a heteroaryl-based compound comprised in a bilayer-structured electron transport layer, but without disclosing specific compounds thereof. Also, the document does not specifically disclose an organic electroluminescent device comprising an electron buffer layer.

Korean Patent Application Laid-Open No. 2010-0118690 discloses that luminescent efficiency may be increased by comprising a compound of a triazine and a benzimidazole linked via a phenyl, a dibenzofluorene or a pyridine in an electron transport layer. However, the document does not specifically disclose a compound of a triazine and a benzimidazole linked via a biphenyl group as an electron transport material, nor does it specifically disclose that the compound may be used as an electron buffer material.

Korean Patent Application Laid-Open No. 2015-0108330 specifically discloses the role of an electron buffer material based on the required material properties and various parameters thereof. Prior to the combination of the electron buffer layer and the electron transport layer of the present disclosure, the basic mechanism for the electron buffer layer is based on this document.

DISCLOSURE OF THE INVENTION

Problems to be Solved

The objective of the present disclosure is to provide an organic electroluminescent device having low driving voltage, high luminous efficiency and/or long lifespan by comprising the compound according to the present disclosure in an electron transport layer and an electron buffer layer.

Solution to Problems

As a result of intensive studies to solve the technical problem above, the present inventors found that the above objective can be achieved by a combination of the specific electron buffer material and the specific electron transport material. Specifically, the above objective can be achieved by an organic electroluminescent device comprising a first electrode, a second electrode facing the first electrode, a light-emitting layer between the first electrode and the second electrode, and an electron transport layer and an electron buffer layer between the light-emitting layer and the second electrode, wherein the electron buffer layer comprises at least one of the compound represented by the following formula 1 and the compound represented by the following formula 2, and the electron transport layer comprises a compound represented by the following formula 2:

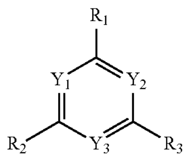

(1)

Wherein $Y_1$ to $Y_3$, each independently, represent N or $CR_4$, with a proviso that at least two of $Y_1$ to $Y_3$ represent N, and $R_1$ to $R_4$, each independently, represent hydrogen, a halogen, a substituted or unsubstituted (C1-C30)alkyl, a substituted or unsubstituted (C6-C60)aryl, or a substituted or unsubstituted (3- to 60-membered)heteroaryl, or $R_4$ may be linked to one of $R_1$ to $R_3$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, wherein $R_1$ to $R_3$ not linked with $R_4$ have the above definition, with a proviso that all of $R_1$ to $R_3$ are not hydrogen;

(2)

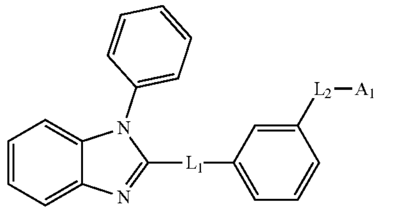

Wherein $L_1$ represents a substituted or unsubstituted (C6-C30) arylene, $L_2$ represents a single bond, or a substituted or unsubstituted (C6-C30)arylene, $A_1$ represents a substituted or unsubstituted (3- to 30-membered)heteroaryl, and the heteroaryl contains at least one heteroatom selected from B, N, O, S, Si, and P.

Effects of the Invention

By comprising the organic electroluminescent compound according to the present disclosure in an electron transport layer and an electron buffer layer, it is possible to provide an organic electroluminescent device having low driving voltage, high luminous efficiency and/or long lifespan.

EMBODIMENTS OF THE INVENTION

Figure 1:
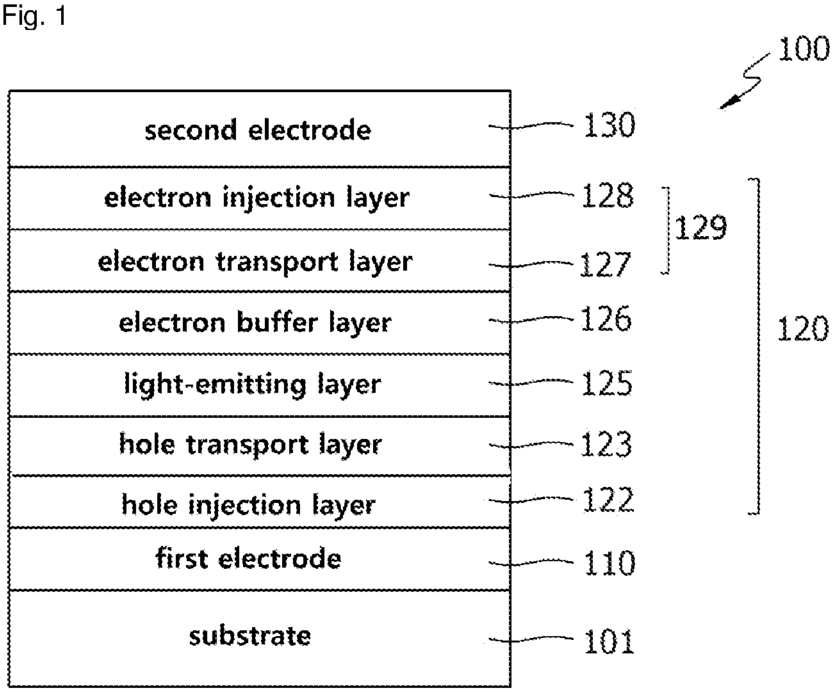
FIG. 1 illustrates a schematic sectional view of an organic electroluminescent device comprising an electron transport layer and an electron buffer layer according to one embodiment of the present disclosure.

Hereinafter, the present disclosure will be described in detail. However, the following description is intended to explain the disclosure, and is not meant in any way to restrict the scope of the disclosure.

The organic electroluminescent device according to one embodiment of the present disclosure may comprise a compound represented by formula 1 as a compound comprising a nitrogen-containing heteroaryl in an electron buffer layer, and a compound represented by formula 2 as a substituted heteroaryl compound which is linked with an imidazole via 3,4-biphenyl as a linker in an electron transport layer. Also, the organic electroluminescent device according to another embodiment of the present disclosure may comprise a compound represented by formula 2 as a substituted heteroaryl compound which is linked with an imidazole via 3,4-biphenyl as a linker in an electron buffer layer and an electron transport layer.

Hereinafter, the organic electroluminescent compounds represented by formulas 1 and 2 will be described in more detail.

In formula 1, $Y_1$ to $Y_3$, each independently, represent N or $CR_4$, with a proviso that at least two of $Y_1$ to $Y_3$ represent N.

In formula 1, $R_1$ to $R_4$, each independently, represent hydrogen, a halogen, a substituted or unsubstituted (C1-C30)alkyl, a substituted or unsubstituted (C6-C60)aryl, or a substituted or unsubstituted (3- to 60-membered)heteroaryl; as one embodiment, hydrogen, a substituted or unsubstituted (C6-C30)aryl, or a substituted or unsubstituted (5- to 50-membered)heteroaryl; and as another embodiment, hydrogen, a substituted or unsubstituted (C6-C25)aryl, or a substituted or unsubstituted (5- to 40-membered)heteroaryl. For example, $R_1$ to $R_3$, each independently, may represent hydrogen, a substituted or unsubstituted phenyl, a substituted indole, a substituted or unsubstituted naphthyl, a substituted or unsubstituted biphenyl, an unsubstituted terphenyl, an unsubstituted dibenzofuranyl, a substituted carbazolyl, a substituted benzocarbazolyl, or a substituted or unsubstituted (17- to 38-membered)heteroaryl, and the heteroaryl may contain at least one heteroatom selected from N, O, and S. For example, $R_4$ may represent hydrogen. Also, $R_4$ may be linked to one of $R_1$ to $R_3$ to form a substituted or unsubstituted, mono- or polycyclic, (C3-C30), preferably (C3-C25), more preferably (C5-C18), alicyclic or aromatic ring, or the combination thereof, whose carbon atom(s) may be replaced with at least one heteroatom selected from nitrogen, oxygen, and sulfur, wherein $R_1$ to $R_3$ not linked with $R_4$ have the above definition. For example, $R_4$ may be linked to one of $R_1$ to $R_3$ to form an unsubstituted benzofuran ring. It is preferable to exclude cases where all of $R_1$ to $R_3$ are hydrogen.

In formula 2, $L_1$ represents a substituted or unsubstituted (C6-C30)arylene; as one embodiment, a substituted or unsubstituted (C6-C25)arylene; as another embodiment, a substituted or unsubstituted (C6-C18)arylene; and for example, an unsubstituted phenylene, an unsubstituted dimethylfluorenylene, an unsubstituted diphenylfluorenylene, or an unsubstituted triphenylenylene.

In formula 2, $L_2$ represents a single bond, or a substituted or unsubstituted (C6-C30)arylene; as one embodiment, a single bond, or a substituted or unsubstituted (C6-C25) arylene; as another embodiment, a single bond, or a substituted or unsubstituted (C6-C18)arylene; and for example, a single bond, or an unsubstituted phenylene.

In formula 2, $A_1$ represents a substituted or unsubstituted (3- to 30-membered)heteroaryl; as one embodiment, a substituted or unsubstituted (3- to 25-membered)heteroaryl; and as another embodiment, a (5- to 18-membered)heteroaryl substituted with a (C6-C25)aryl(s). For example, $A_1$ may represent a substituted triazinyl, a substituted pyrimidinyl, or a substituted 13-membered heteroaryl containing nitrogen and/or oxygen, wherein the substituents of the substituted triazinyl, the substituted pyrimidinyl and the substituted 13-membered heteroaryl may be at least one of phenyl, biphenyl, naphthyl, dimethylfluorenyl, diphenylfluorenyl, terphenyl and phenanthrenyl.

According to one embodiment of the present disclosure, formula 1 may be represented by any one of the following formulas 3 to 8, preferably, any one of following formulas 3 to 5:

(3)

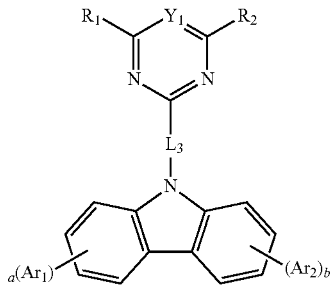

(4)

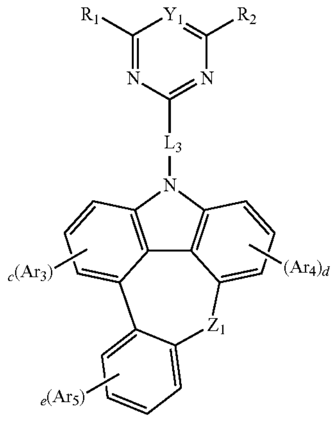

(5)

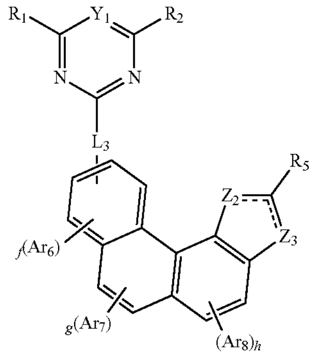

-continued (6)

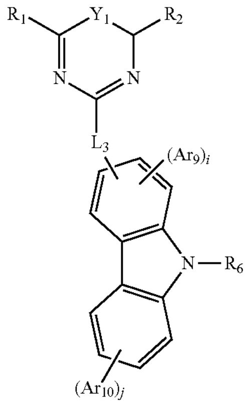

(7)

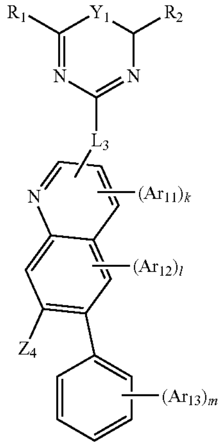

(8)

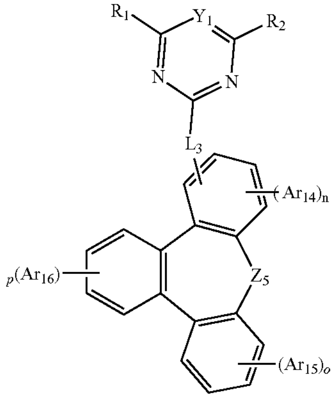

In formulas 3 to 8, $Y_1$ represents N or $CR_4$.

In formulas 3 to 8, $R_1$, $R_2$ and $R_4$, each independently, represent hydrogen, a halogen, a substituted or unsubstituted (C1-C30)alkyl, a substituted or unsubstituted (C6-C30)aryl, or a substituted or unsubstituted (3- to 30-membered)heteroaryl, or $R_4$ may be linked to $R_1$ or $R_2$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, wherein $R_1$ and $R_2$ not linked with $R_4$ have the above definition. As one embodiment, $R_1$, $R_2$ and $R_4$, each independently, represent hydrogen, a substituted or unsubstituted (C6-C25)aryl, or a substituted or unsubstituted (3- to 25-membered)heteroaryl, or $R_4$ may be linked to $R_1$ or $R_2$ to form a substituted or unsubstituted, mono- or polycyclic, (C5-C25) alicyclic or aromatic ring, or the combination thereof, whose carbon atom(s) may be replaced with at least one heteroatom selected from nitrogen, oxygen, and sulfur. As another embodiment, $R_1$, $R_2$ and $R_4$, each independently, represent hydrogen, a substituted or unsubstituted (C6-C18)aryl, or a substituted or unsubstituted (5- to 18-membered)heteroaryl, or $R_4$ may be linked to $R_1$ or $R_2$ to form a substituted or unsubstituted, mono- or polycyclic, (C5-C18) alicyclic or aromatic ring, or the combination thereof, whose carbon atom(s) may be replaced with oxygen. For example, $R_1$ and $R_2$, each independently, may represent hydrogen, a substituted or unsubstituted phenyl, an unsubstituted naphthyl, an unsubstituted biphenyl, an unsubstituted terphenyl, or an unsubstituted dibenzofuranyl, or $R_4$ may be linked to $R_1$ or $R_2$ to form an unsubstituted benzofuran ring.

In formulas 3 to 8, $L_3$ represents a single bond, a substituted or unsubstituted (C6-C30)arylene, or a substituted or unsubstituted (3- to 30-membered)heteroarylene; as one embodiment, a single bond, a substituted or unsubstituted (C6-C25)arylene, or a substituted or unsubstituted (5- to 25-membered)heteroarylene; as another embodiment, a single bond, a substituted or unsubstituted (C6-C18)arylene, or a substituted or unsubstituted (5- to 18-membered)heteroarylene; and for example, a single bond, an unsubstituted phenylene, an unsubstituted naphthylene, an unsubstituted biphenylene, or an unsubstituted benzocarbazolylene.

In formulas 4, 7 and 8, $Z_1$, $Z_4$ and $Z_5$, each independently, represent O, S, $NR_7$ or $CR_8C_9$; and as one embodiment, O, $NR_7$ or $CR_8C_9$. For example, $Z_1$ may represent O or $NR_7$; $Z_4$ represents $CR_8C_9$; and $Z_5$ represents $NR_7$.

In formula 5, any one of $Z_2$ and $Z_3$ represents =N— or =$CR_{10}$—, and the other of $Z_2$ and $Z_3$ represents O, S, $NR_{11}$ or $CR_{12}R_{13}$; and as one embodiment, any one of $Z_2$ and $Z_3$ represents =N— or =$CR_{10}$—, and the other thereof represents O or S. For example, $Z_3$ may represent S when $Z_2$ represents =N— or =$CR_{10}$—, and $Z_3$ represents =N— when $Z_2$ represents O.

In formulas 3 to 8, $Ar_1$ to $Ar_{16}$ and $R_5$ to $R_{13}$, each independently, represent hydrogen, deuterium, a halogen, a cyano, a carboxyl, a nitro, a hydroxyl, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C3-C30)cycloalkenyl, —$NR_{14}R_{15}$ or —$SiR_{16}R_{17}R_{18}$, or may be linked to an adjacent substituent to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur; as one embodiment, hydrogen, a substituted or unsubstituted (C1-C20)alkyl, a substituted or unsubstituted (C6-C25)aryl, or a substituted or unsubstituted (5- to 25-membered)heteroaryl, or may be linked to an adjacent substituent to form a substituted or unsubstituted, mono- or polycyclic, (C5-C25) alicyclic or aromatic ring, or the combination thereof, whose carbon atom(s) may be replaced with at least one heteroatom selected from nitrogen, oxygen, and sulfur; and as another embodiment, hydrogen, a substituted or unsubstituted (C1-C10)alkyl, a substituted or unsubstituted (C6-C18)aryl, or a substituted or unsubstituted (5- to 18-membered)heteroaryl, or may be linked to an adjacent substituent to form a substituted or unsubstituted, mono- or polycyclic, (C5-C18) alicyclic or aromatic ring, or the combination thereof, whose carbon atom(s) may be replaced with at least one heteroatom selected from nitrogen, oxygen, and sulfur. For example, $Ar_1$ and $Ar_2$, each independently, may represent hydrogen, an unsubstituted methyl, an unsubstituted tert-butyl, an unsubstituted phenyl, a fluoreneyl substituted with a phenyl(s), an unsubstituted dibenzofuranyl, an unsubstituted dibenzothiophenyl, or a carbazolyl substituted with a phenyl(s), or may be linked to an adjacent substituent to form a substituted nitrogen-containing 5-membered heteroaryl ring, an unsubstituted benzene ring, a substituted indene ring, an unsubstituted benzofuran ring, an unsubstituted benzothiophene ring, or a benzoindene ring substituted with a phenyl(s); $Ar_3$, $Ar_5$ to $Ar_8$, and $Ar_{12}$ to $Ar_{16}$, each independently, may represent hydrogen; $Ar_4$ may represent hydrogen, or an unsubstituted phenyl; $Ar_9$ may represent hydrogen, or may be linked to an adjacent substituent to form an unsubstituted benzene ring; $Ar_{10}$ may represent hydrogen, or may be linked to an adjacent substituent to form an unsubstituted benzene ring or an unsubstituted fluorene ring; $Ar_{11}$ may represent an unsubstituted phenyl, or an unsubstituted naphthyl; $R_5$ represents an unsubstituted phenyl; $R_6$ may represent an unsubstituted phenyl, or a carbazolyl substituted with a phenyl(s); $R_7$ and $R_{11}$, each independently, may represent an unsubstituted phenyl; $R_8$ to $R_{10}$, $R_{12}$ and $R_{13}$, each independently, may represent an unsubstituted methyl; $Ar_4$ and $R_9$ may be linked to each other to form an unsubstituted indole ring; and $R_5$ and $R_{12}$ may be linked to each other to form an unsubstituted benzene ring.

In formulas 3 to 8, $R_{14}$ to $R_{18}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl.

In formulas 3 to 8, a, b, e, j, m, o and p, each independently, represent an integer of 1 to 4; c, d, f, i and n, each independently, represent an integer of 1 to 3; g, h, k and l, each independently, represent 1 or 2; where if a to p, each independently, are an integer of 2 or more, each of $Ar_1$ to $Ar_{16}$ may be the same or different. As one embodiment, a to p, each independently, represent 1 or 2. As another embodiment, a to h, and k to p, each independently, represent 1, and i and j, each independently, represent 1 or 2.

According to one embodiment of the present disclosure, formula 2 may be represented by the following formula 9:

(9)

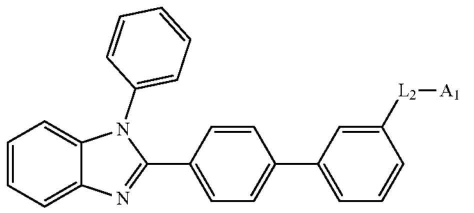

In formula 9, $L_2$ represents a single bond, or a substituted or unsubstituted (C6-C30)arylene; as one embodiment, a single bond, or a substituted or unsubstituted (C6-C25) arylene; as another embodiment, a single bond, or a substituted or unsubstituted (C6-C18)arylene; and for example, a single bond, or an unsubstituted phenylene.

In formula 9, $A_1$ may be represented by any one of the following formulas 10 and 11:

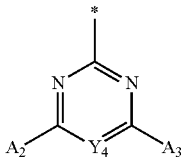
(10)

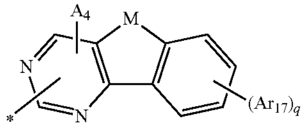
(11)

In formulas 10 and 11,*represents a bonding site with $L_2$ of formula 9.

In formula 10, $Y_4$ represents N or $CR_{19}$.

In formula 11, M represents O or $S_1$ as one embodiment, represents O.

In formulas 10 and 11, $A_2$ to $A_4$, $R_{19}$ and $Ar_{17}$, each independently, represent hydrogen, a substituted or unsubstituted (C1-C30)alkyl, a substituted or unsubstituted (C6-C30)aryl, or a substituted or unsubstituted (3- to 30-membered)heteroaryl, or $R_4$ may be linked to $R_2$ or $R_3$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur; as one embodiment, hydrogen, a substituted or unsubstituted (C6-C25) aryl, or a substituted or unsubstituted (5- to 25-membered) heteroaryl; and another embodiment, hydrogen, a substituted or unsubstituted (C6-C25)aryl. For example, $A_2$ and $A_3$, each independently, may represent hydrogen, an unsubstituted phenyl, an unsubstituted naphthyl, an unsubstituted biphenyl, an unsubstituted dimethylfluorenyl, an unsubstituted diphenylfluorenyl, an unsubstituted phenanthrenyl, or an unsubstituted terphenyl; $R_{19}$ may represent hydrogen; $A_4$ may represent an unsubstituted phenyl, or an unsubstituted naphthyl; and $Ar_{17}$ may represent hydrogen.

In formula 11, q represents an integer of 1 to 4; as one embodiment, represents 1 or 2; and as another embodiment, represents 1.

In formulas 1 to 11, the heteroaryl(ene) contains at least one heteroatom selected from B, N, O, S, Si, and P; and as one embodiment, at least one heteroatom selected from N, O and S.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. The term "(C3-C30)cycloalkyl" is a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered) heterocycloalkyl" is a cycloalkyl having 3 to 7, preferably 5 to 7, ring backbone atoms, and including at least one heteroatom selected from the group consisting of the group consisting of B, N, O, S, Si, and P, and preferably the group consisting of the group consisting of O, S, and N. The above heterocycloalkyl may include tetrahydrofuran, pyrrolidine, thiolan, tetrahydropyran, etc. The term "(C6-C60)aryl(ene)" is a monocyclic or fused ring radical derived from an aromatic hydrocarbon having 6 to 60 ring backbone carbon atoms, in which the number of the ring backbone carbon atoms is preferably 6 to 30, more preferably 6 to 20. The above aryl(ene) may be partially saturated, and may comprise a spiro structure. The above aryl may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 60-membered)heteroaryl(ene)" is an aryl having 3 to 60 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted alkyl, the substituted cycloalkyl, the substituted cycloalkenyl, the substituted heterocycloalkyl, the substituted aryl(ene), the substituted heteroaryl(ene), and the substituted mono- or polycyclic, alicyclic or aromatic ring, or the combination thereof, in $R_1$ to $R_{19}$, $L_1$ to $L_3$, $A_1$ to $A_4$, and $Ar_1$ to $Ar_{17}$ of formulas 1 to 11, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (C6-C30)aryl, a (5- to 60-membered)heteroaryl unsubstituted or substituted with a (C1-C30)alkyl(s) and/or a (C6-C30)aryl(s), a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; as one embodiment, each independently, are at least one selected from the group consisting of a (C1-C20)alkyl, a (5- to 50-membered)heteroaryl unsubstituted or substituted with a (C1-C20)alkyl(s) and/or (C6-C25)aryl(s), a (C6-C28)aryl, and a (C1-C20) alkyl(C6-C25)aryl; and as another embodiment, each independently, are at least one selected from the group consisting of a (C1-C10)alkyl, a (6- to 40-membered)heteroaryl unsubstituted or substituted with a (C1-C10)alkyl(s) and/or (C6-C20)aryl(s), a (C6-C25)aryl, and a (C1-C10)alkyl(C6-C18) aryl. For example, the substituents may be at least one selected from the group consisting of an unsubstituted methyl; an unsubstituted tert-butyl; an unsubstituted phenyl; an unsubstituted naphthyl; an unsubstituted biphenyl; a dimethylfluorenyl; a phenylfluorenyl; a diphenylfluorenyl; an unsubstituted phenanthrenyl; an unsubstituted terphenyl; a triazinyl substituted with a phenyl(s); an indole substituted with a phenyl(s); a benzimidazole substituted with a phenyl(s); a carbazolyl substituted with at least one of methyl, phenyl, phenylfluorenyl, dibenzothiophenyl, carbazolyl substituted with phenyl, and dibenzofuranyl; an unsubstituted dibenzofuranyl; an unsubstituted dibenzothiophenyl; an unsubstituted xanthenyl; a benzocarbazolyl unsubstituted or substituted with a phenyl(s); an unsubstituted benzophenanthrothiophenyl; an unsubstituted dibenzocarbazolyl; a 13-membered heteroaryl substituted with a phenyl(s); a 16-membered heteroaryl substituted with a phenyl(s); a 17-membered heteroaryl substituted with at least one of methyl, phenyl and naphthyl; a 19-membered heteroaryl substituted with a phenyl(s); a 20-membered heteroaryl unsubstituted or substituted with a tert-butyl(s); a 24-membered heteroaryl substituted with a phenyl(s); and an unsubstituted 26-membered heteroaryl, and the heteroaryl may contain at least one heteroatom selected from N, O and S.

The compound represented by formula 1 includes the following compounds, but is not limited thereto.

B-1

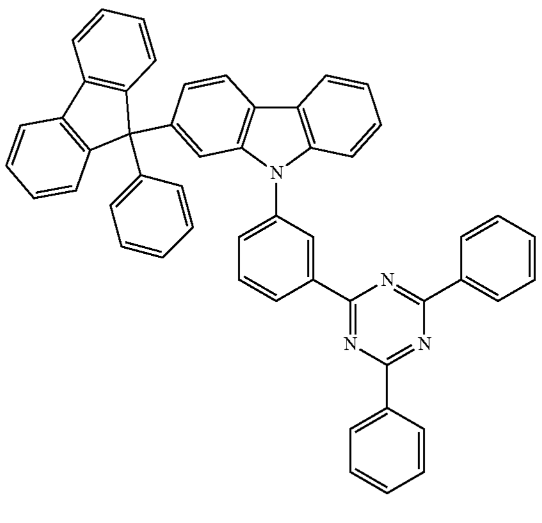

-continued

B-2

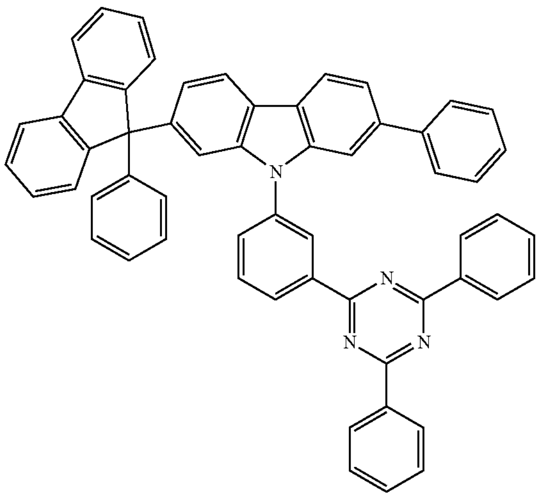

B-3

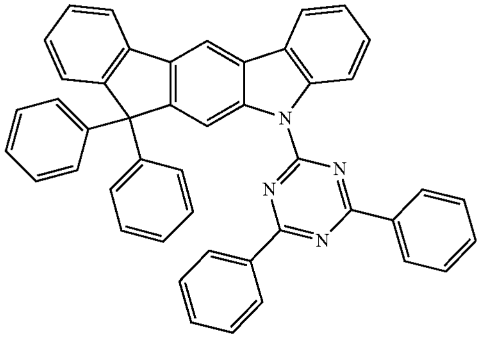

B-4

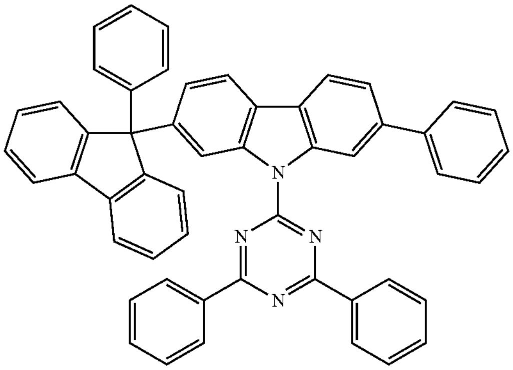

-continued
B-5
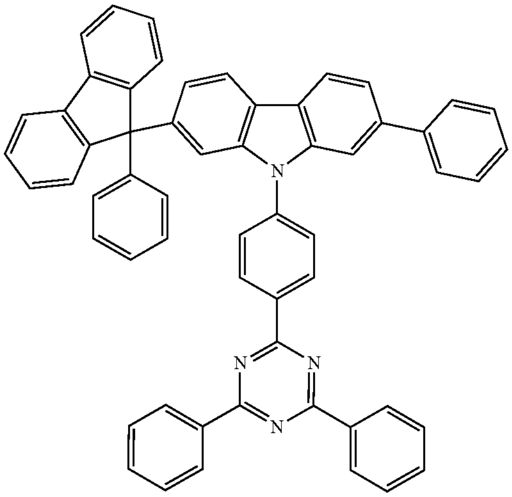
B-6
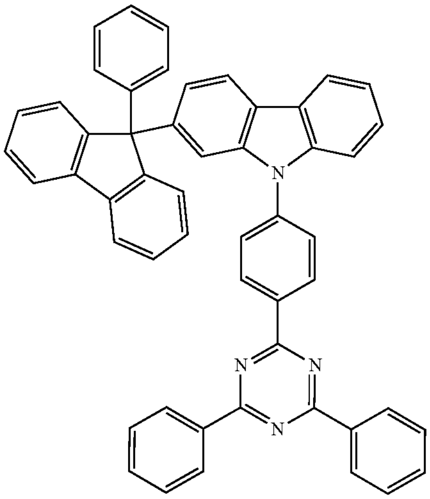
B-7
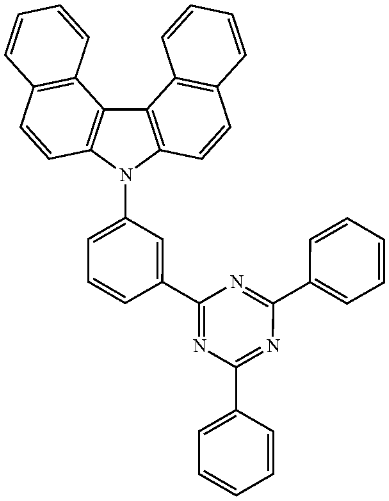
-continued
B-8
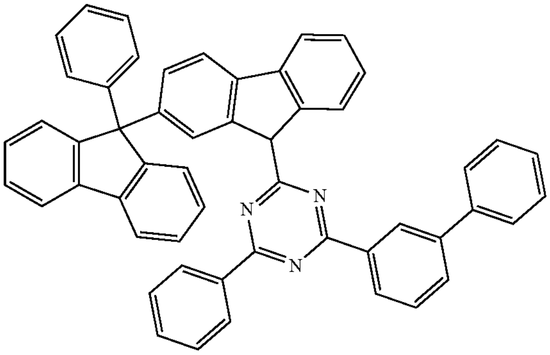
B-9
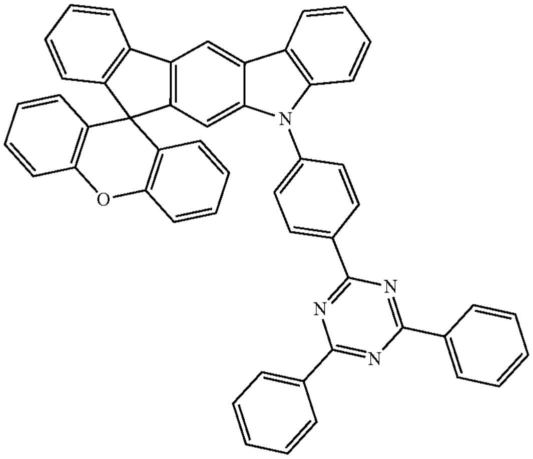
B-10
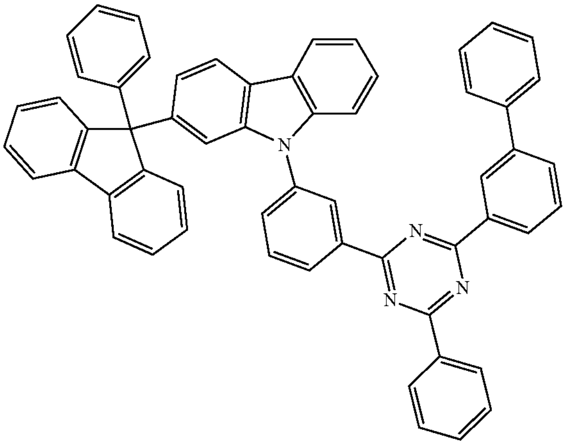

-continued
B-11
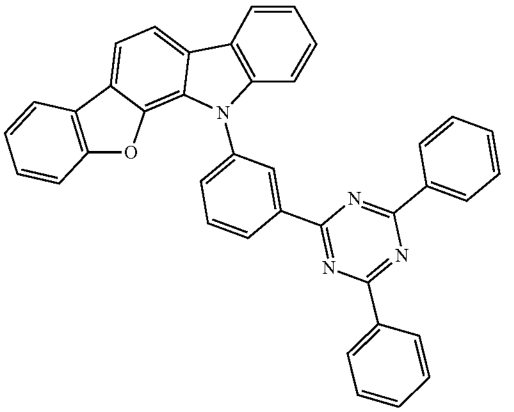
B-12
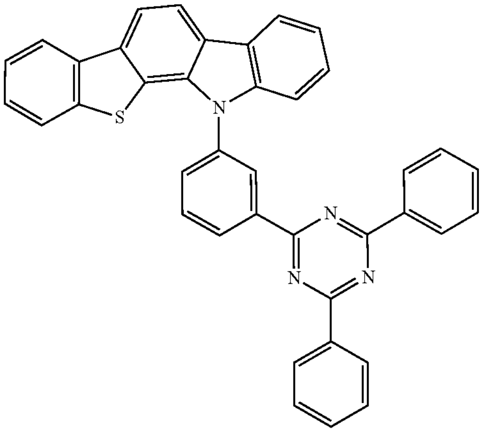
B-13
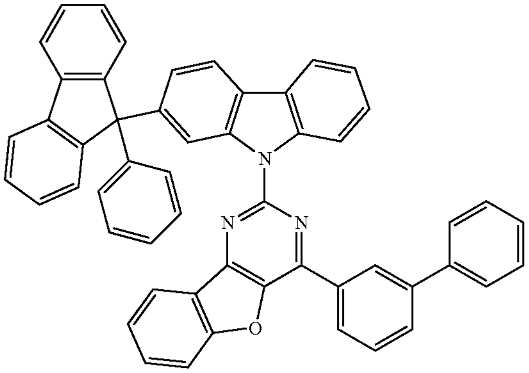
-continued
B-14
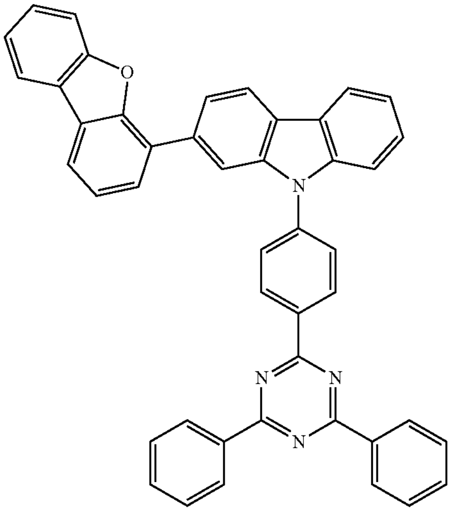
B-15
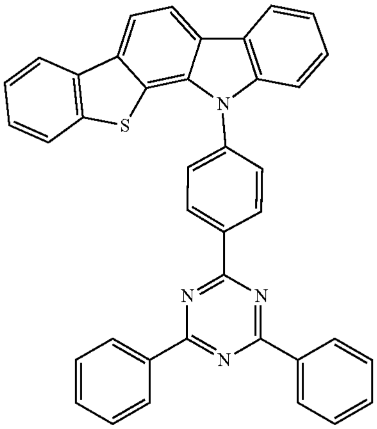
B-16
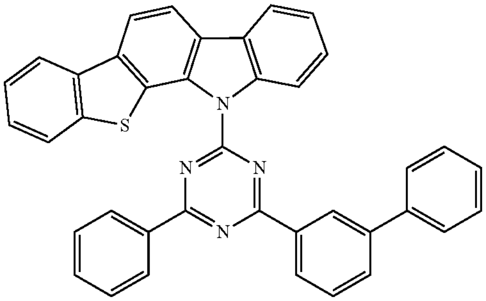
B-17
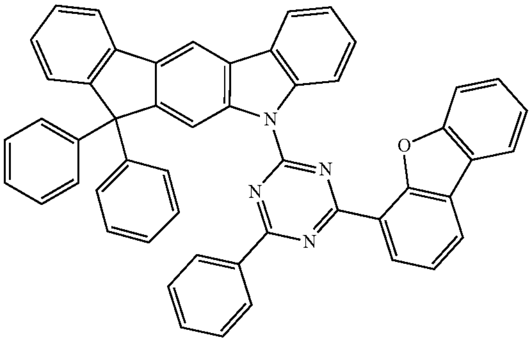

-continued
B-18
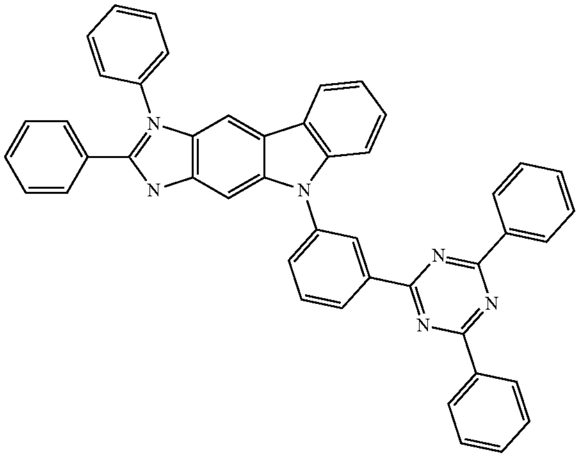
B-19
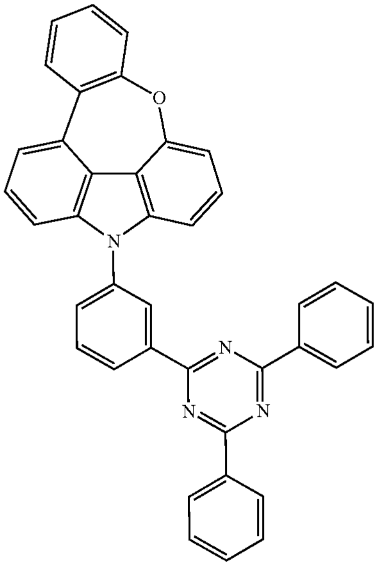
B-20
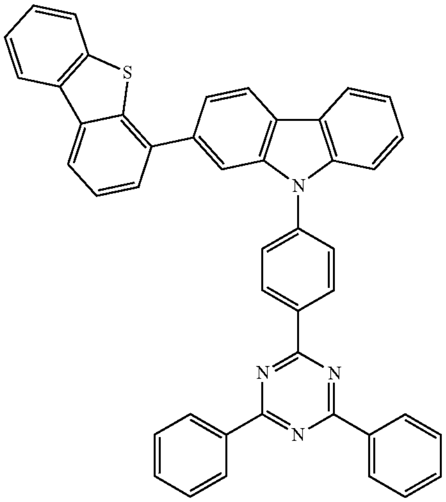
-continued
B-21
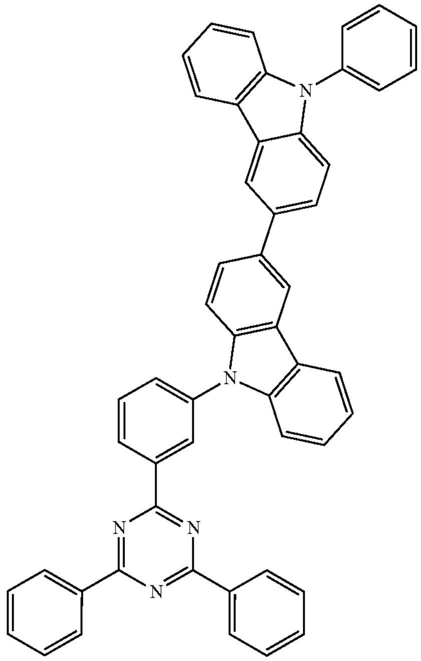
B-22
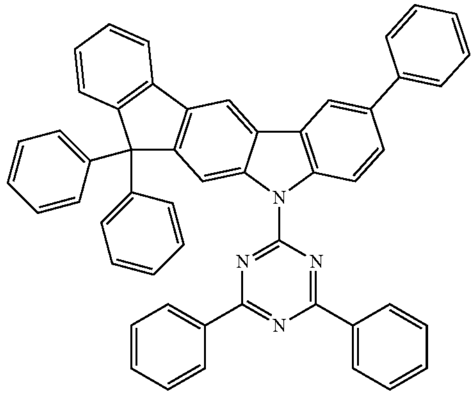
B-23
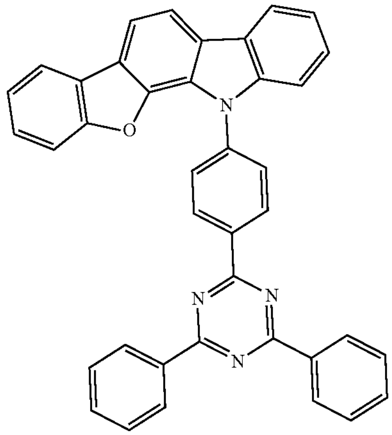

-continued
B-24
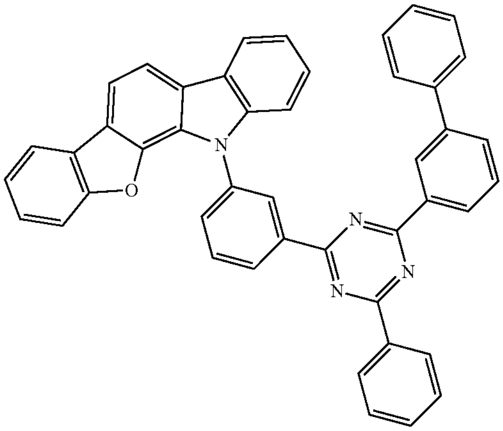
B-25
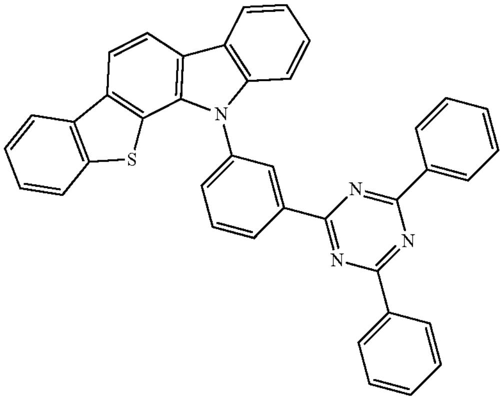
B-26
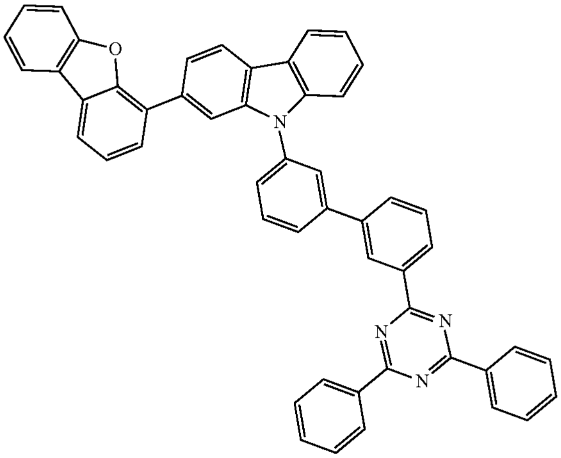
-continued
B-27
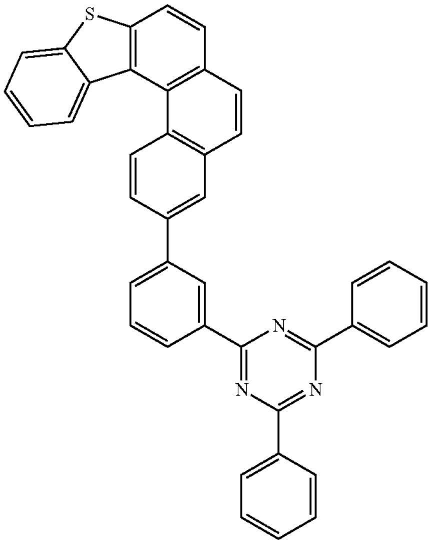
B-28
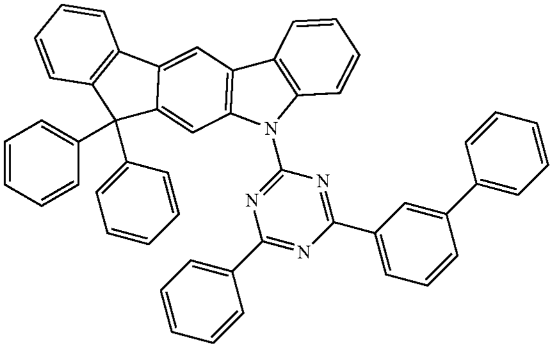
B-29
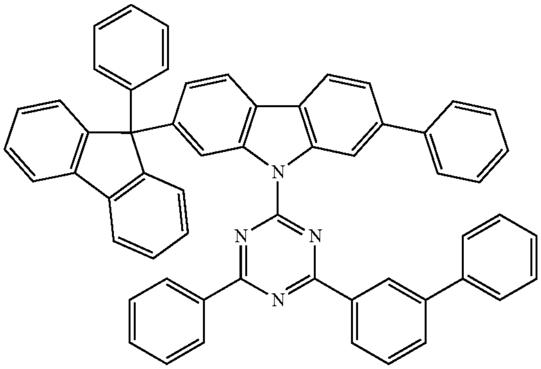

-continued
B-30
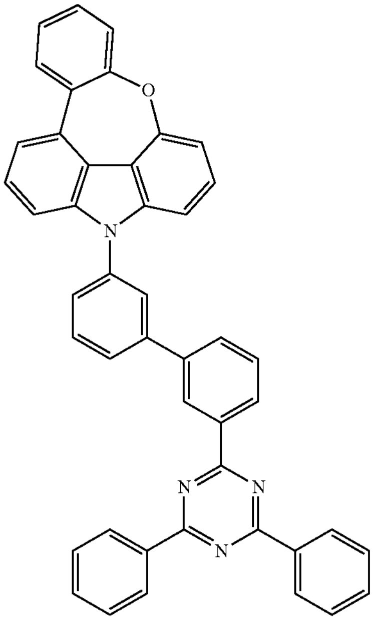
B-31
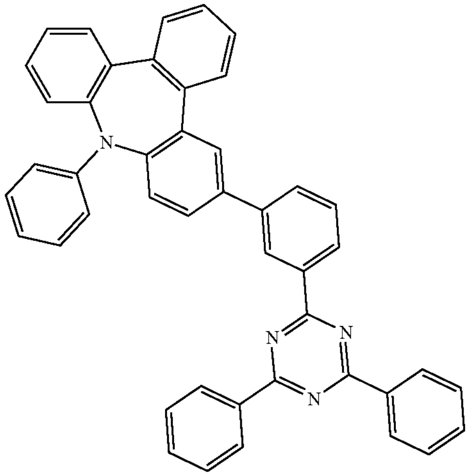
B-32
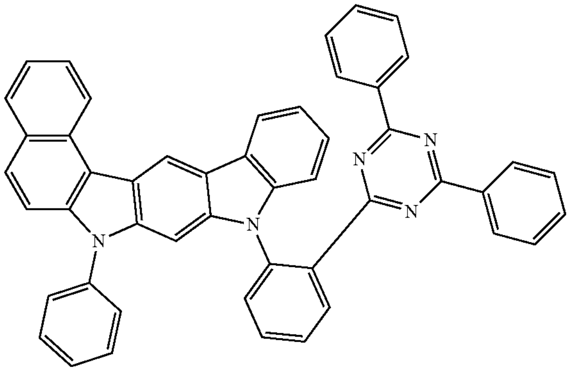
-continued
B-33
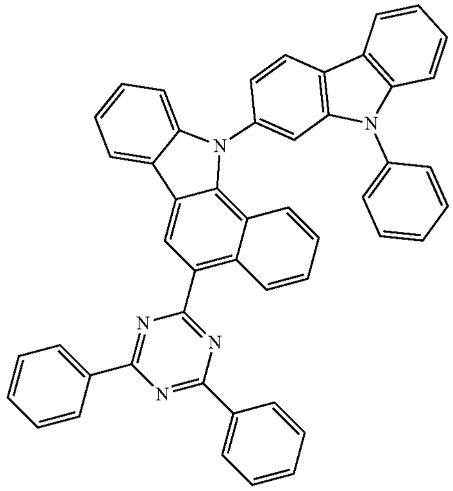
B-34
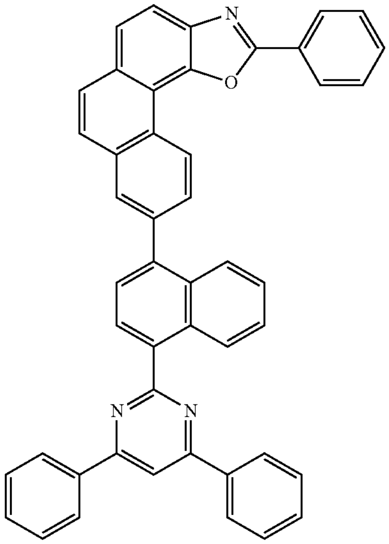
B-35
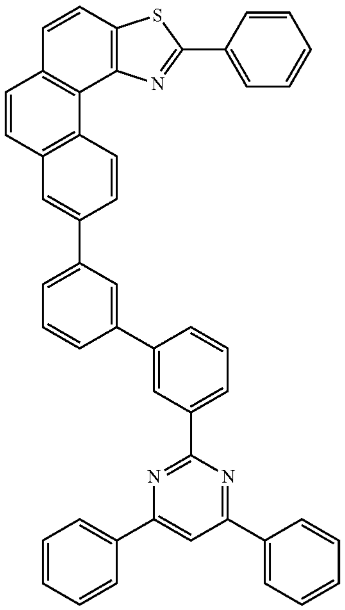

-continued
B-36
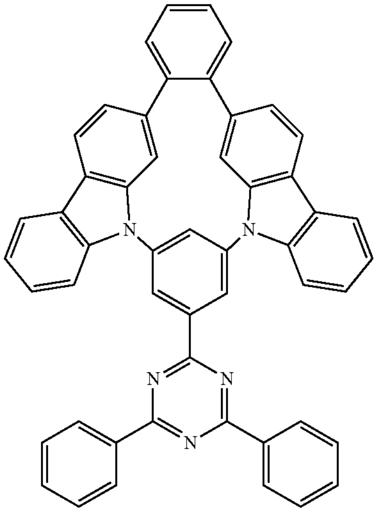
B-37
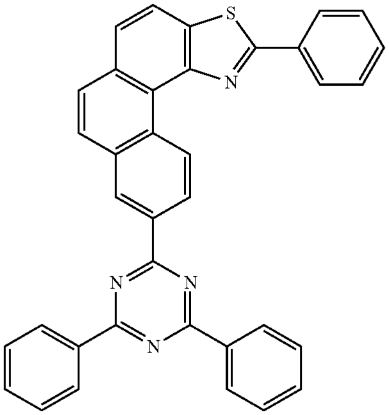
B-38
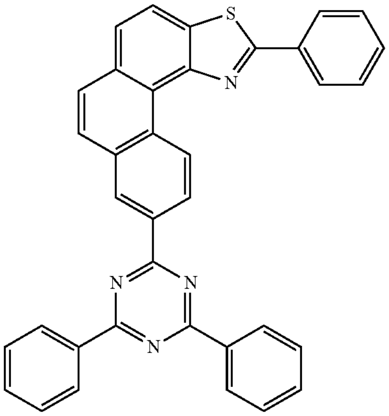
-continued
B-39
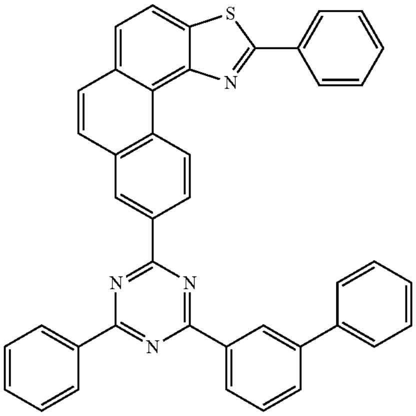
B-40
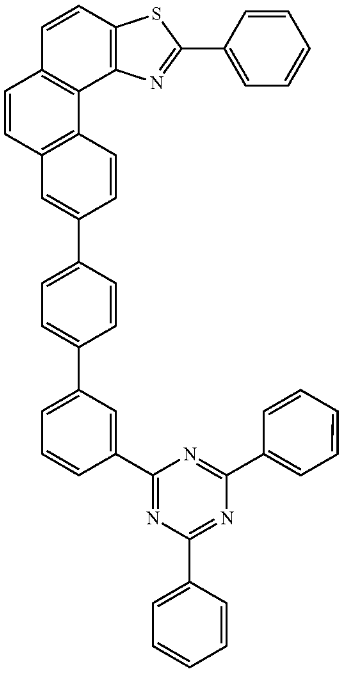
B-41
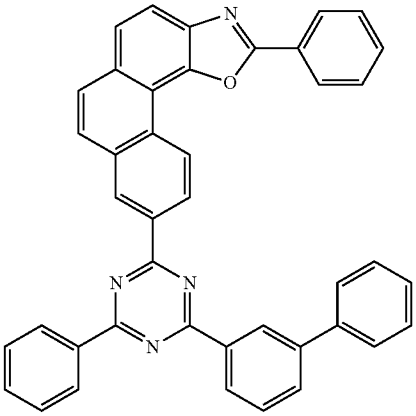

-continued
B-42
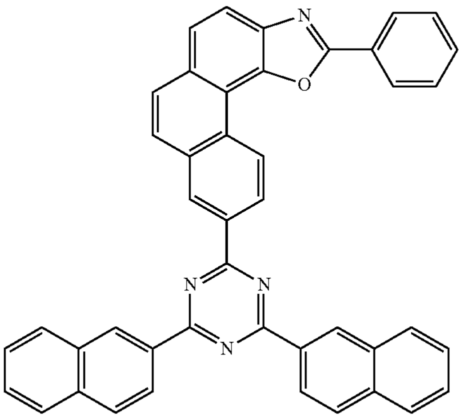
B-43
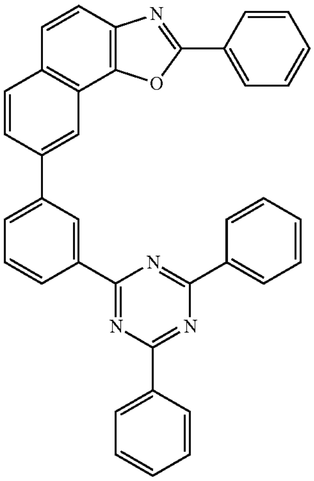
B-44
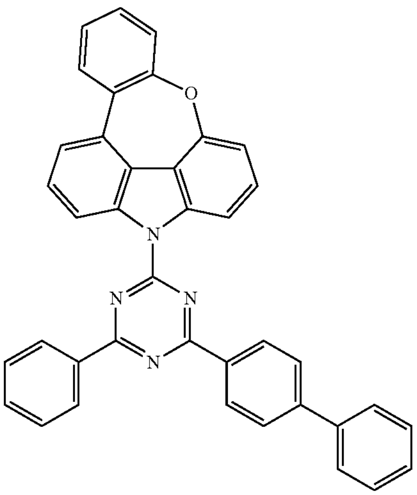
-continued
B-45
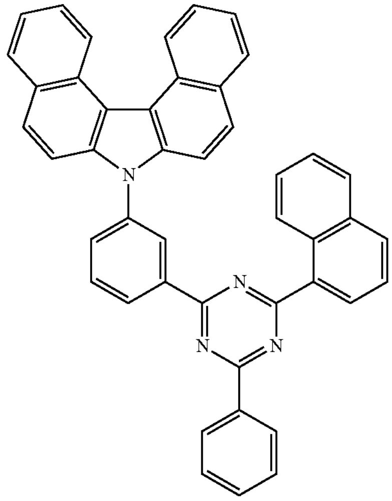
B-46
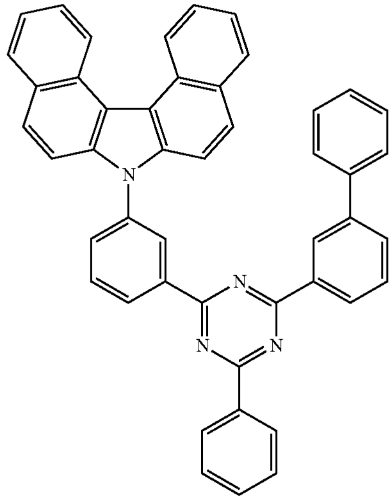
B-47
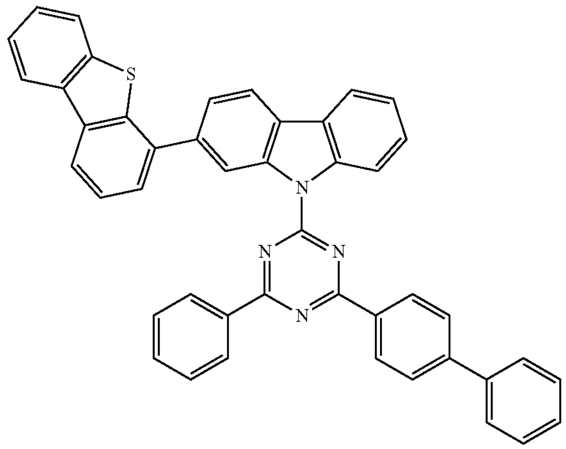

-continued
B-48
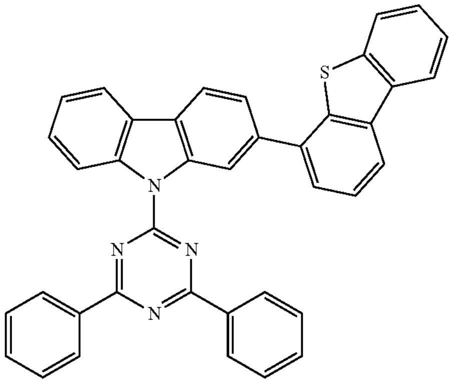
B-49
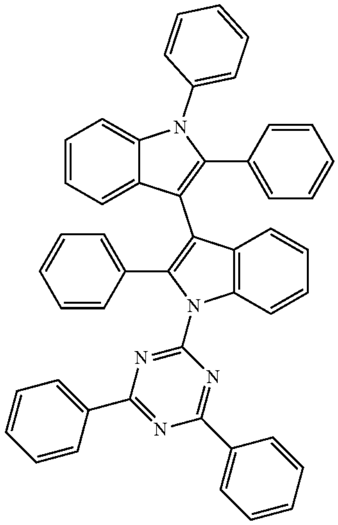
B-50
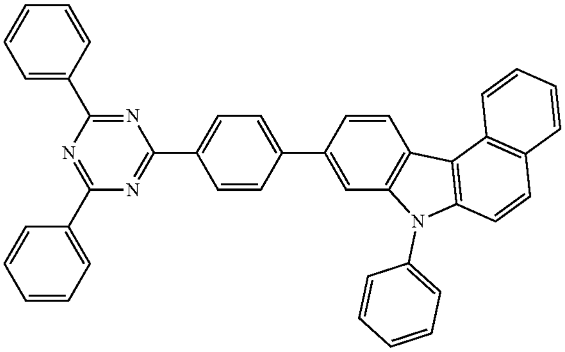
-continued
B-51
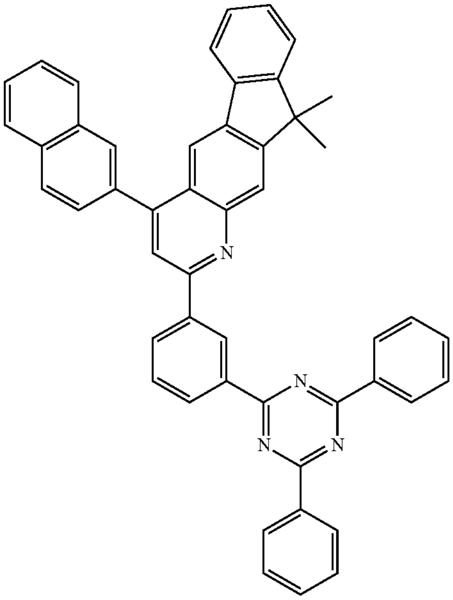
B-52
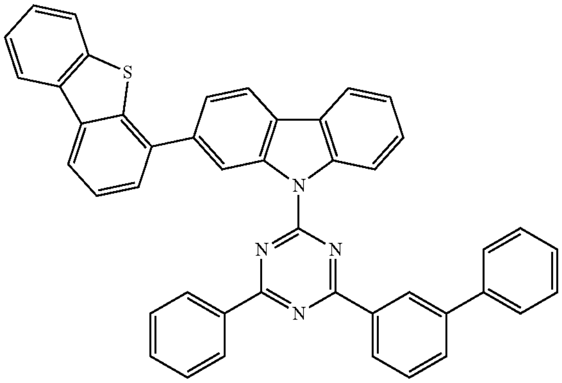
B-53
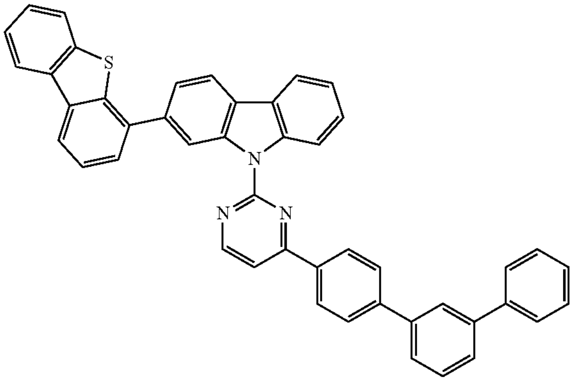

-continued
B-54
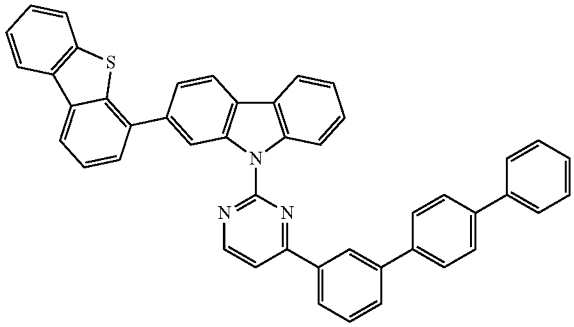
B-55
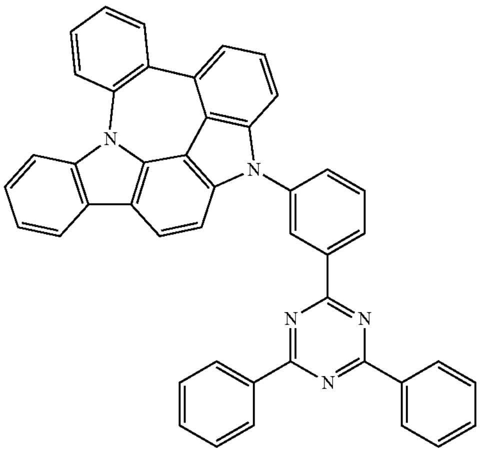
B-56
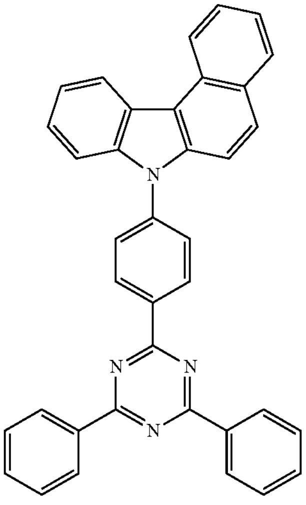
-continued
B-57
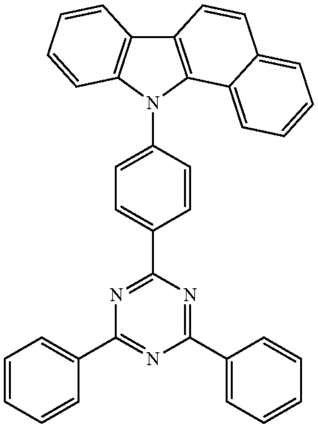
B-58
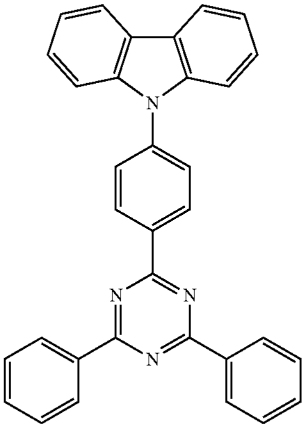
B-59
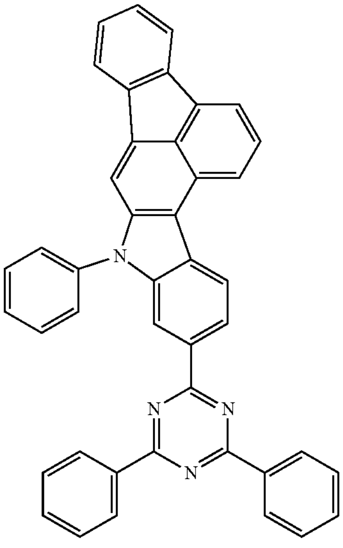

-continued
B-60
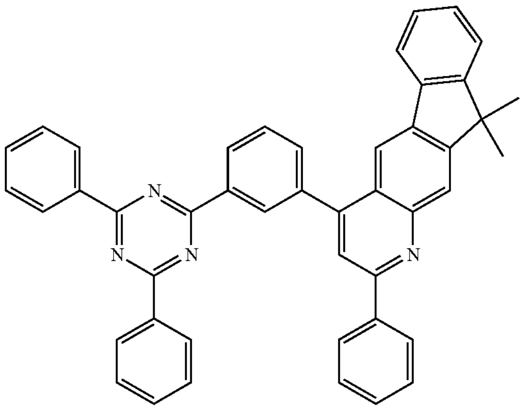
B-61
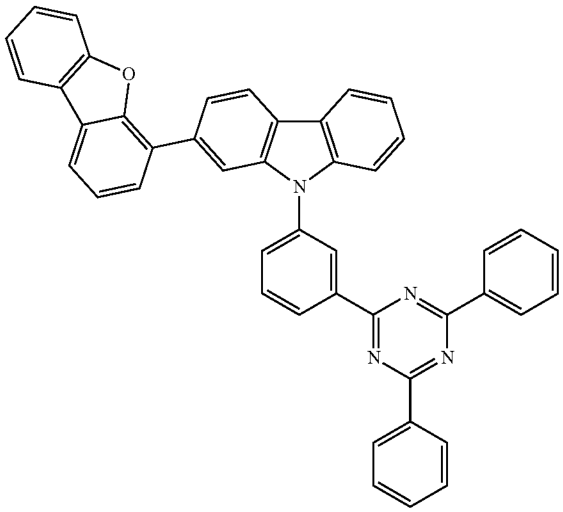
B-62
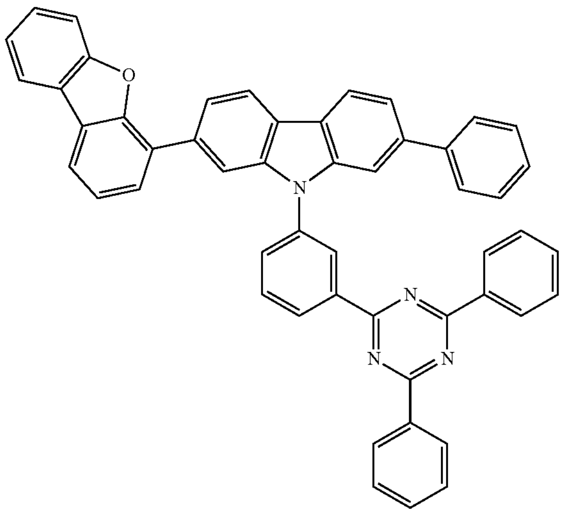
-continued
B-63
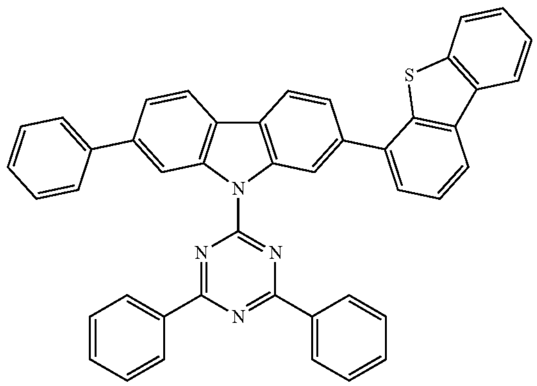
B-64
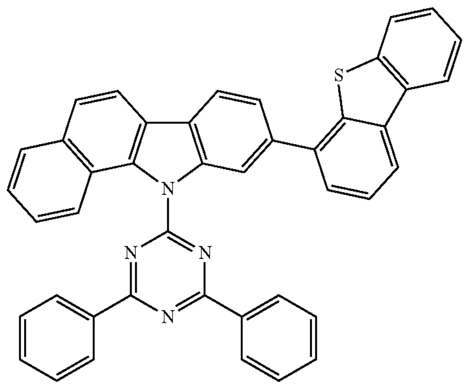
B-65
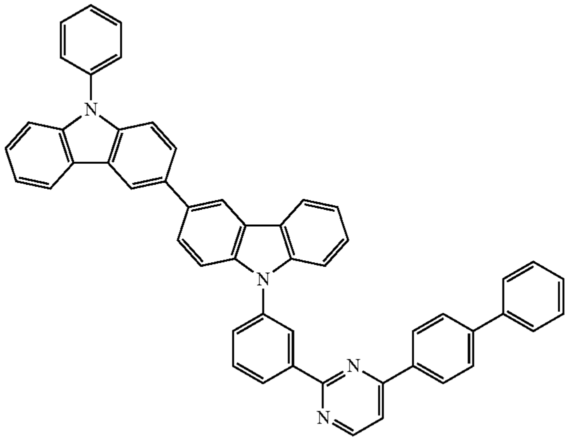

-continued
B-66
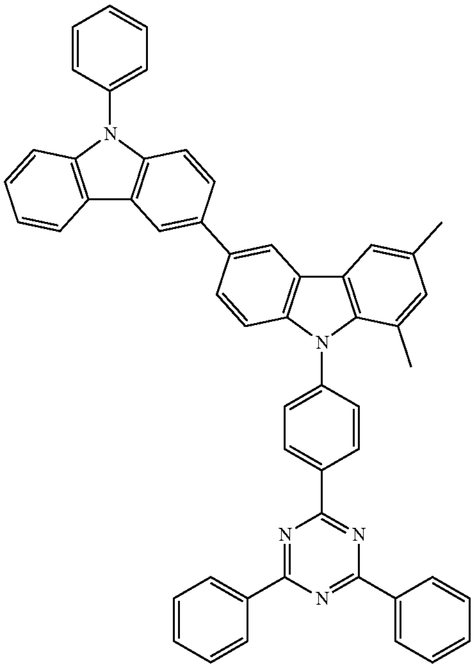
B-67
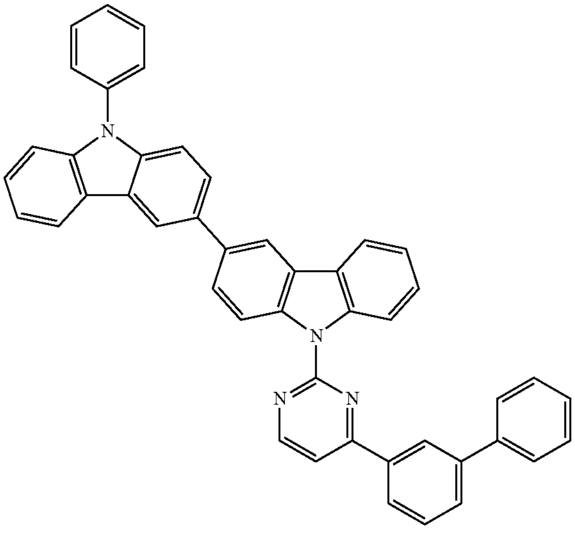
-continued
B-68
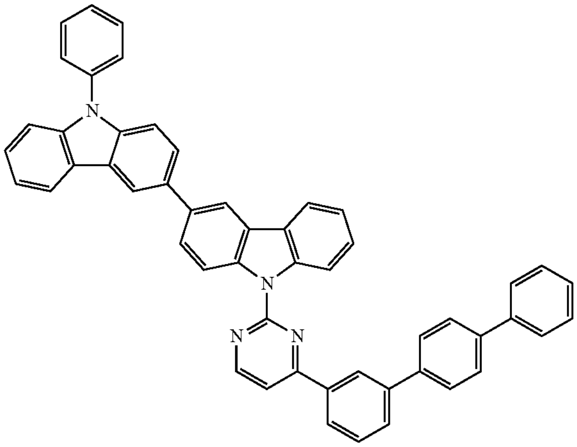
B-69
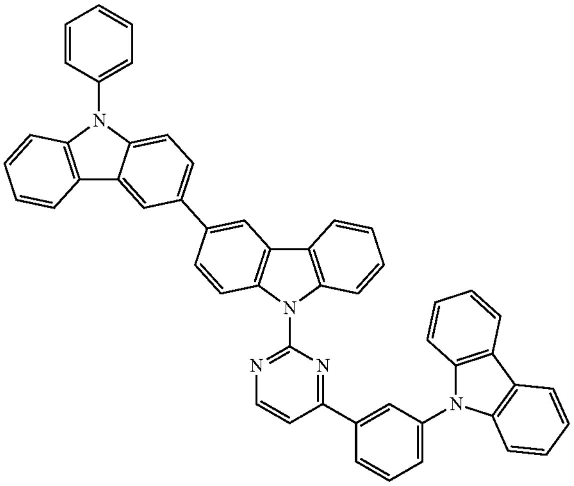
B-70
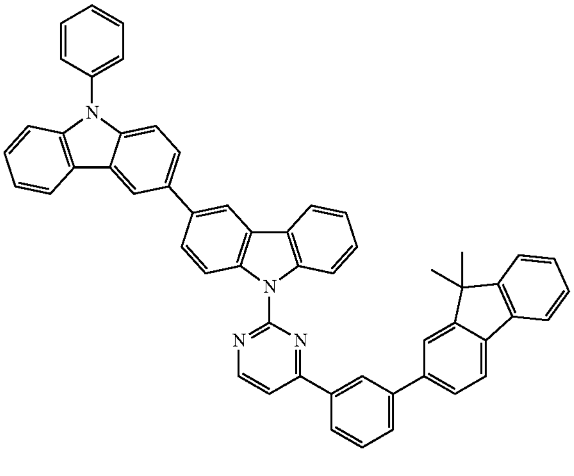

-continued
B-71
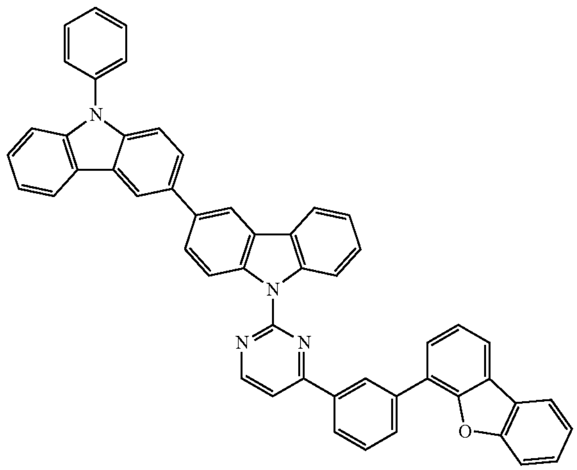
B-72
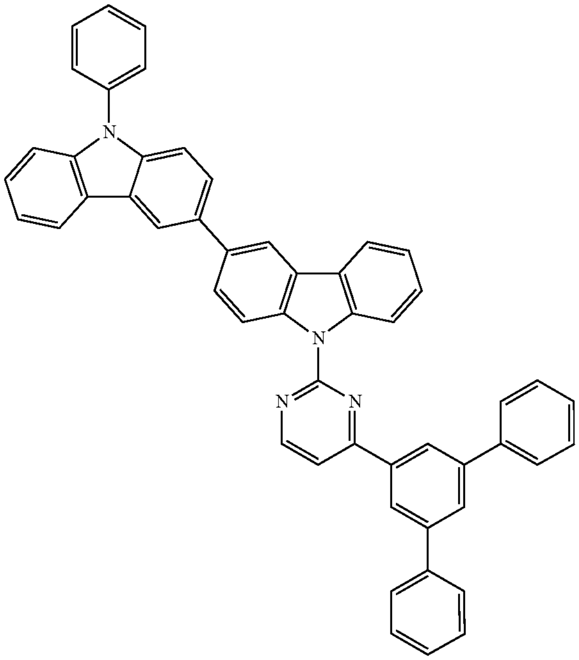
B-73
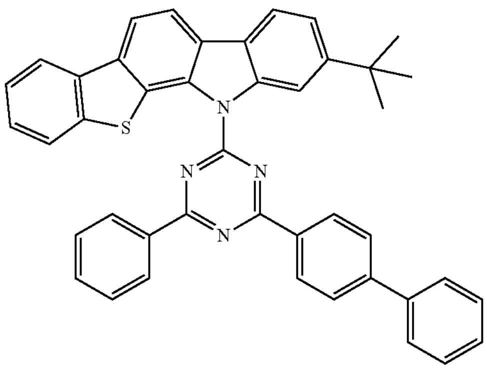
-continued
B-74
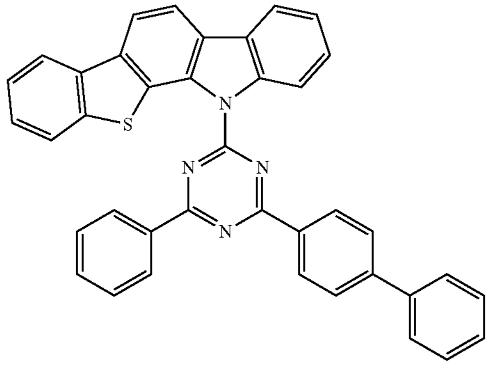
B-75
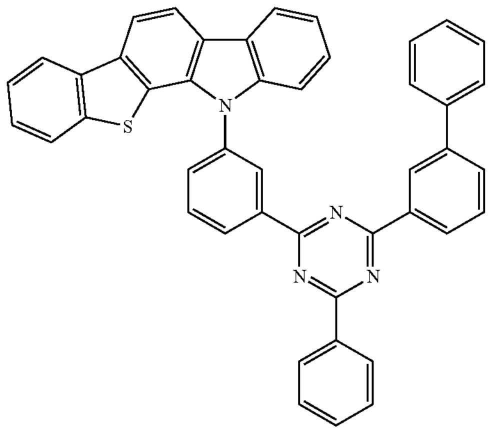
B-76
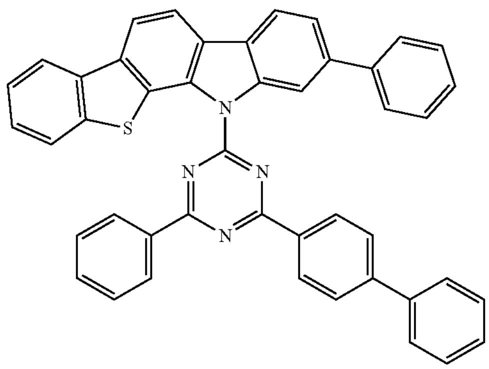

-continued
B-77
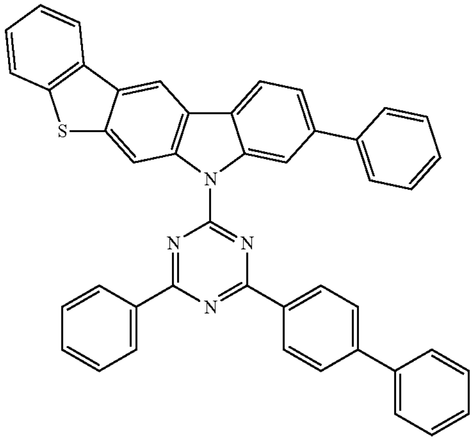
B-78
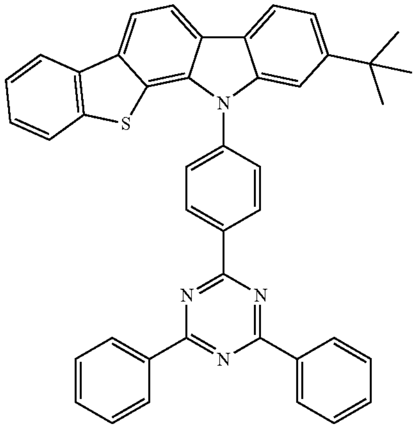
B-79
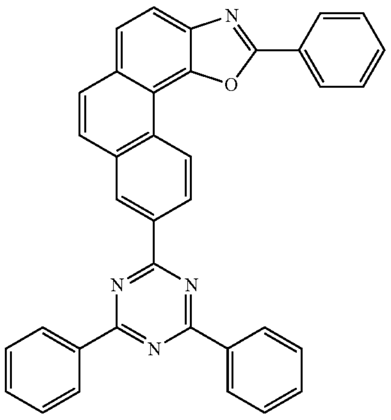
-continued
B-80
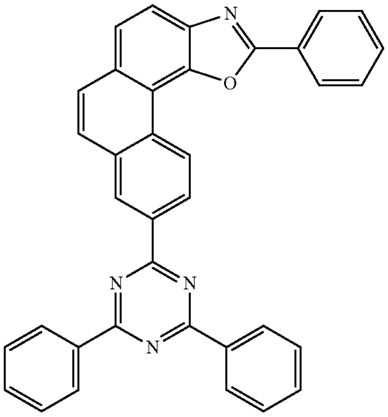
B-81
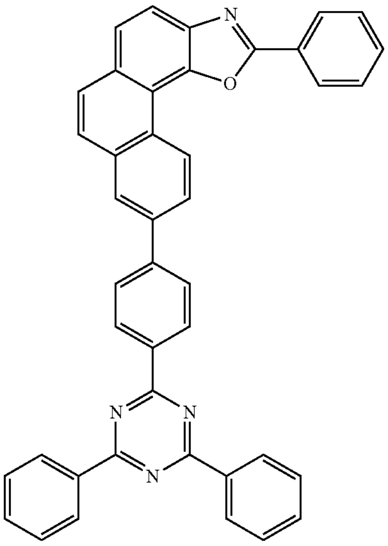
B-82
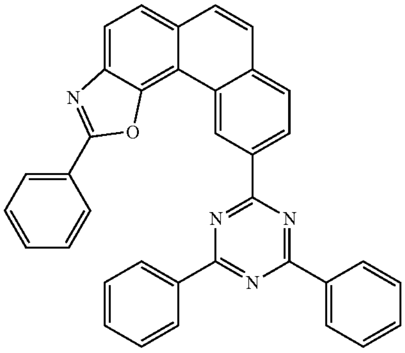

-continued
B-83
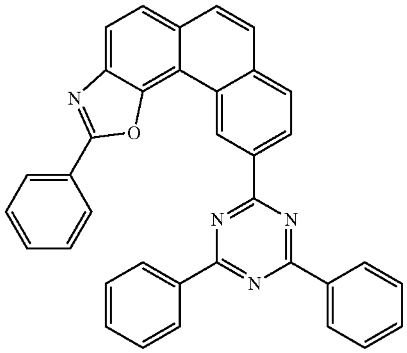
B-84
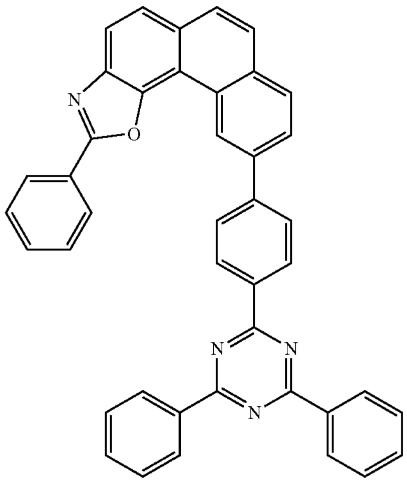
B-85
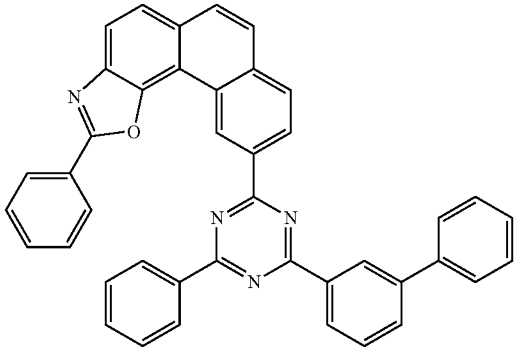
-continued
B-86
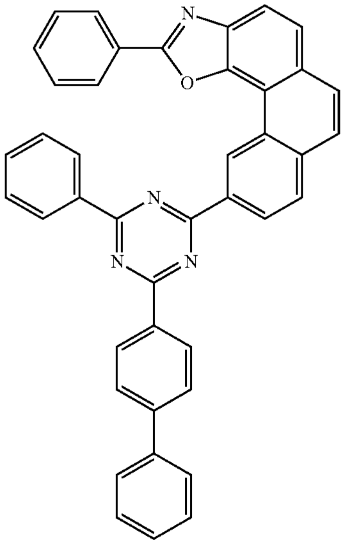
B-87
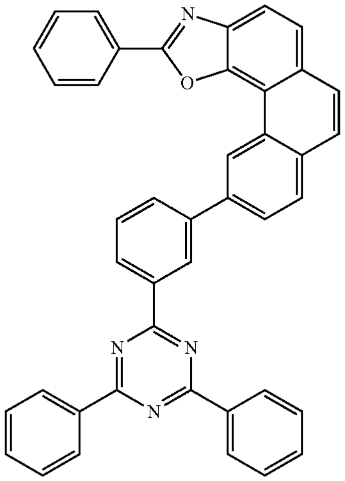
B-88
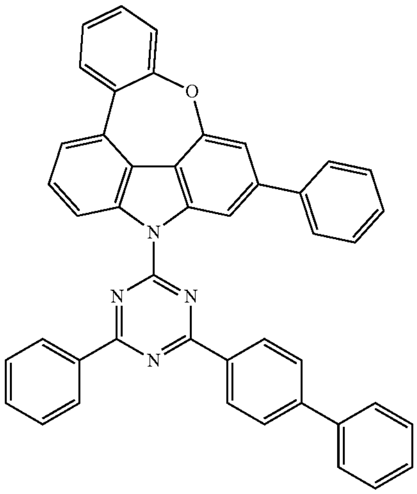

B-89
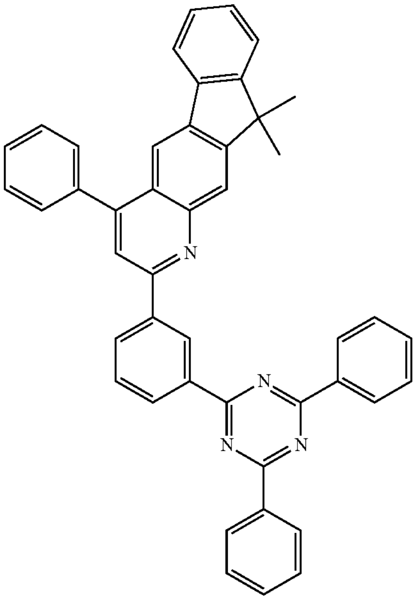
B-90
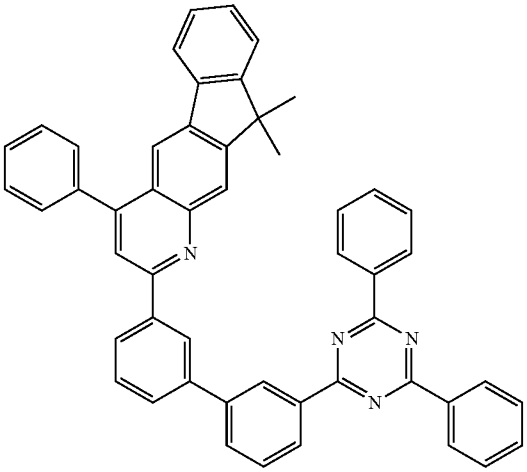
The compound represented by formula 2 includes the following compounds, but is not limited thereto.
C-1
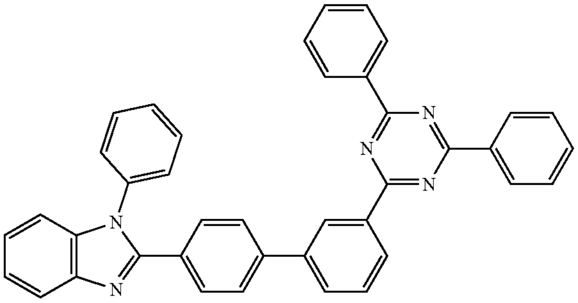
C-2
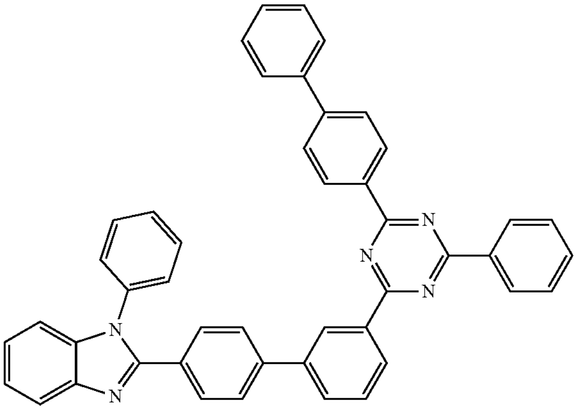
C-3
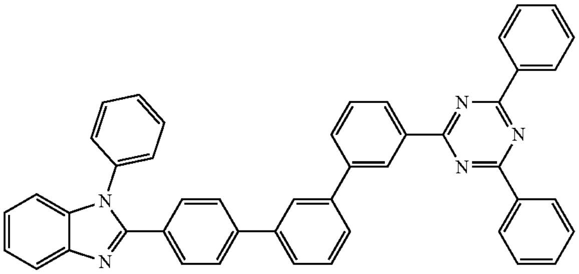
C-4
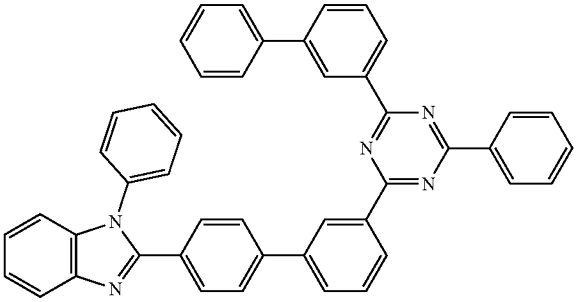
C-5
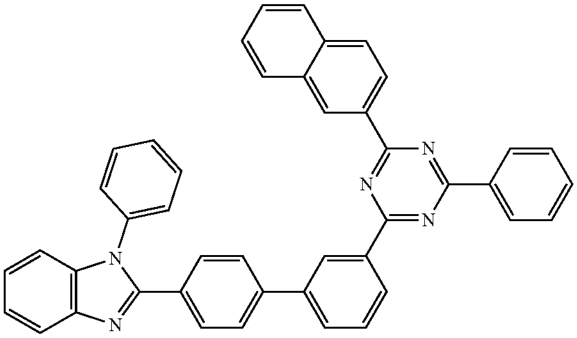

-continued
C-6
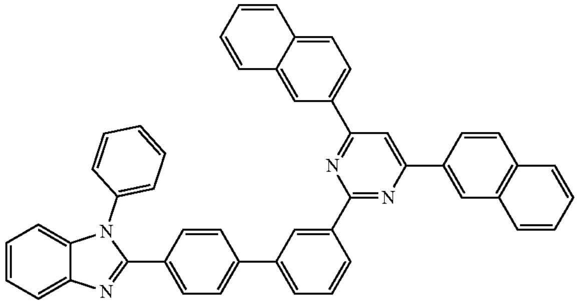
C-7
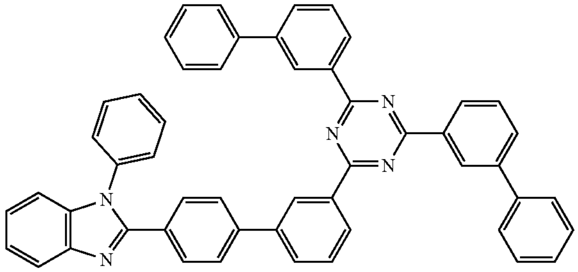
C-8
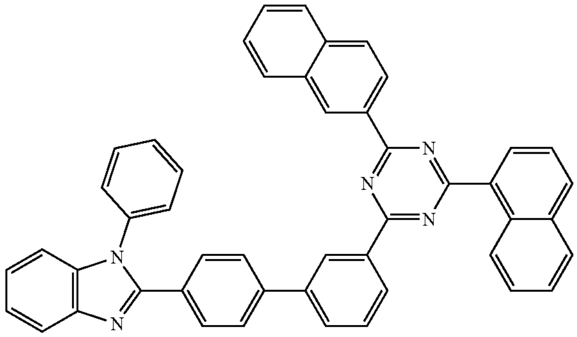
C-9
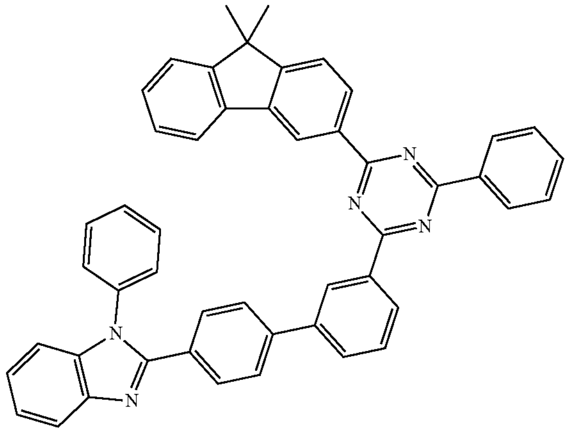
-continued
C-10
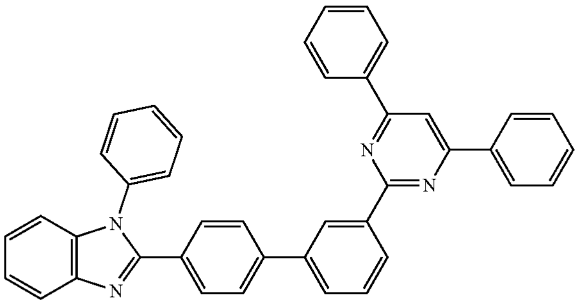
C-11
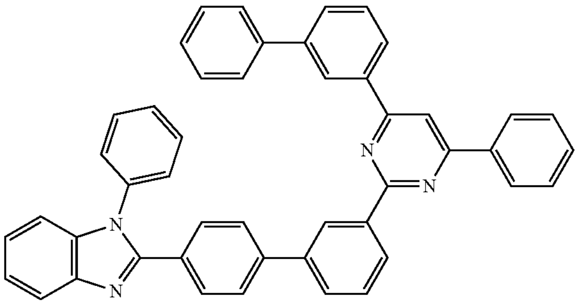
C-12
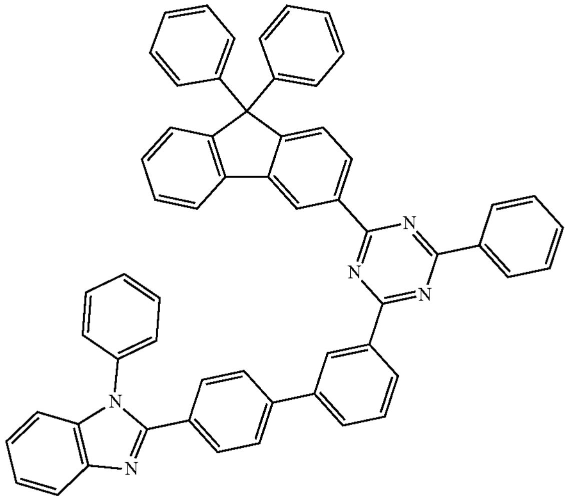
C-13
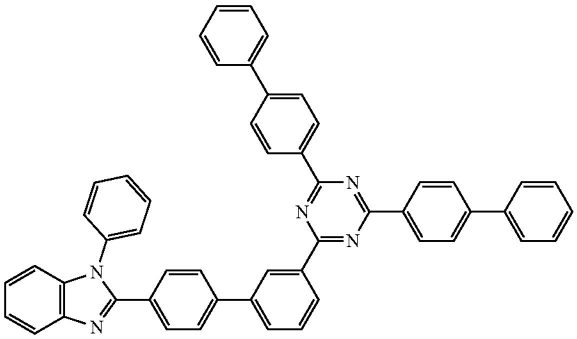

-continued
C-14
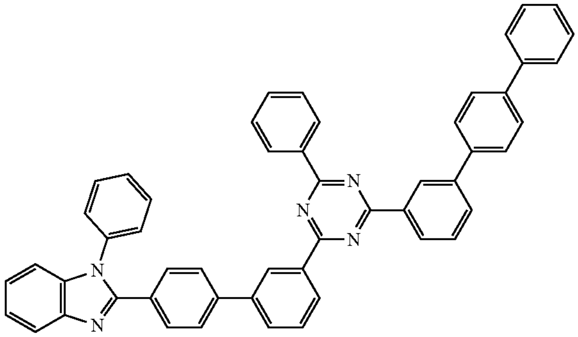
C-15
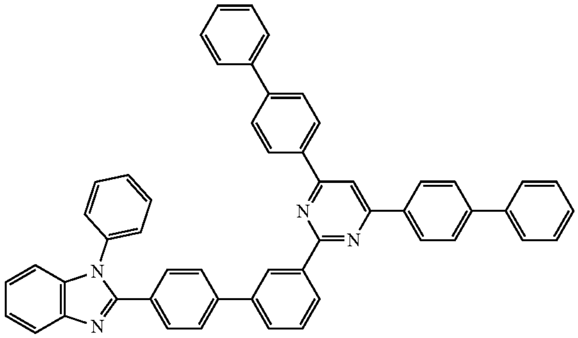
C-16
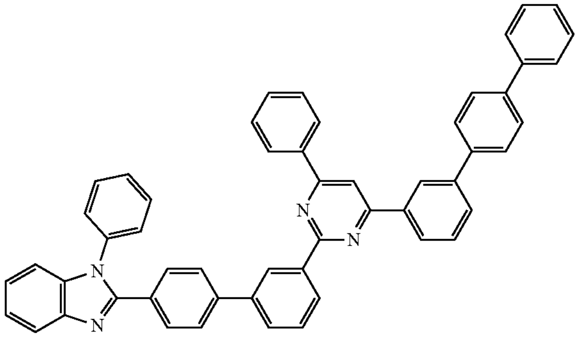
C-17
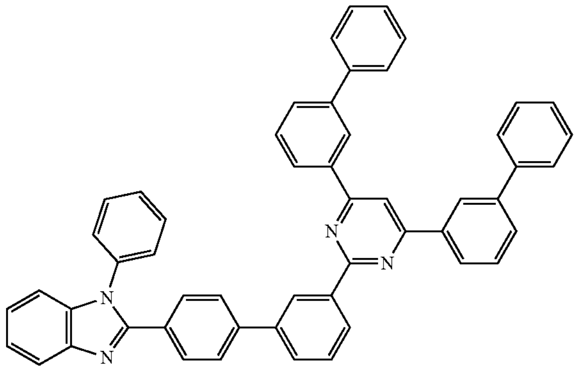
-continued
C-18
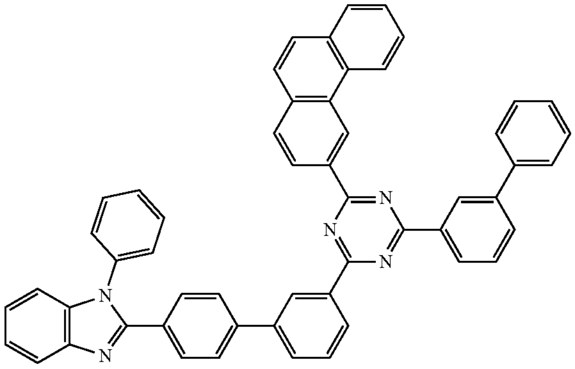
C-19
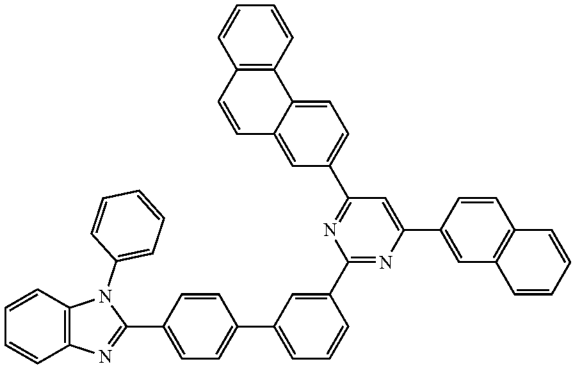
C-20
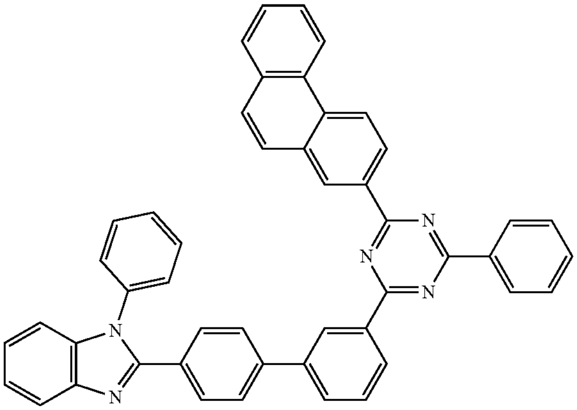
C-21
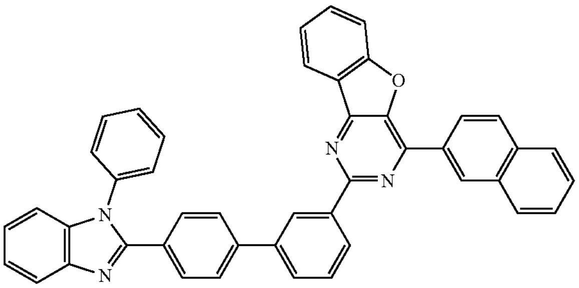

-continued

C-22

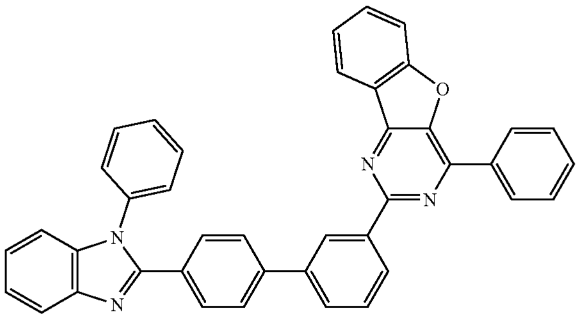

C-23

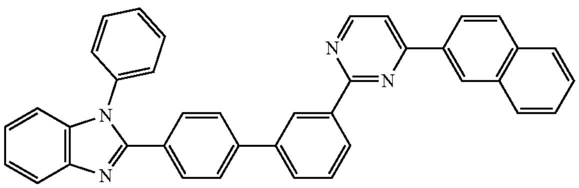

C-24

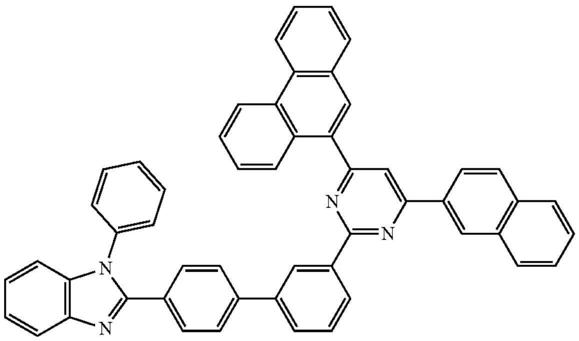

C-25

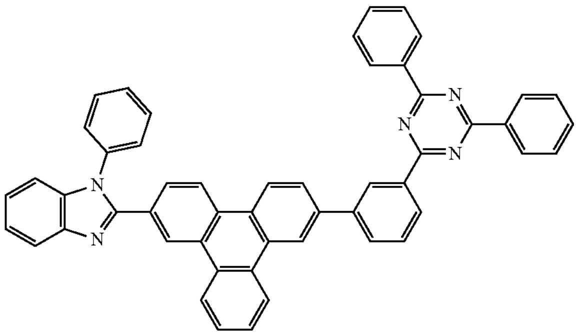

C-26

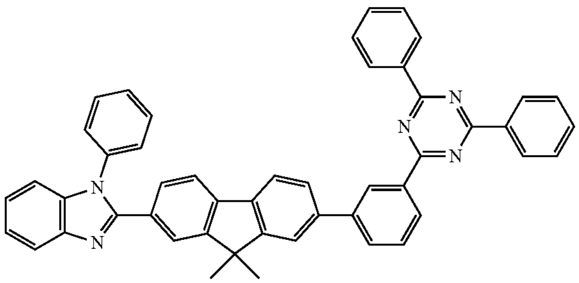

-continued

C-27

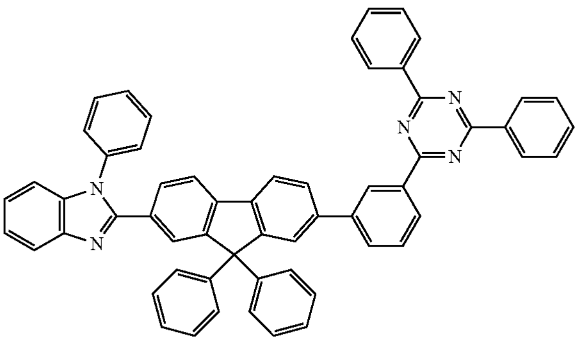

C-28

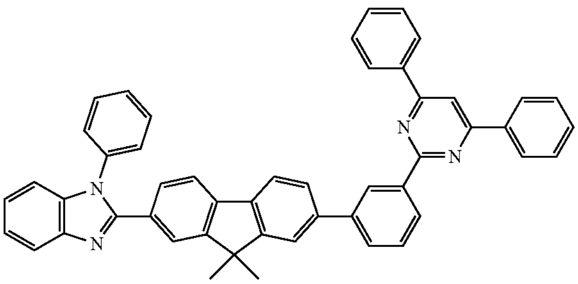

C-29

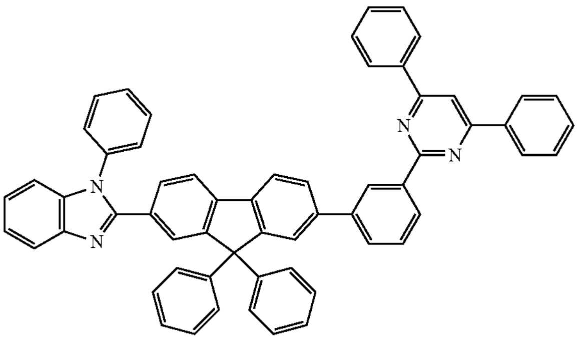

The present disclosure is directed to an organic electroluminescent device comprising a first electrode, a second electrode facing the first electrode, a light-emitting layer between the first electrode and the second electrode, and an electron transport zone and an electron buffer layer between the light-emitting layer and the second electrode, wherein the electron transport zone comprises an electron injection layer and an electron transport layer, the electron buffer layer comprises a compound comprising a nitrogen-containing heteroaryl, and the electron transport layer comprises a substituted heteroaryl compound which is linked with an imidazole via 3,4-biphenyl as a linker. Also, the electron buffer layer may be located between the light-emitting layer and the electron transport zone, or between the electron transport zone and the second electrode.

The electron transport zone in the present disclosure means a zone in which electrons are transported from the second electrode to the light-emitting layer in the device. The electron transport zone may comprise an electron transport compound, a reductive dopant, or the combination thereof. The electron transport compound may be at least one selected from a group consisting of imidazole-based compounds, oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes. The reductive dopant may be selected from alkali metals, alkali metal compounds, alkaline earth metals, rare-earth metals, and halides, oxides, and complexes thereof. The electron transport zone may comprise an electron transport layer, an electron injection layer, or both of them. The electron transport layer and the electron injection layer may be composed of two or more layers, respectively.

FIG. 1 illustrates a schematic sectional view of an organic electroluminescent device according to one embodiment of the present disclosure. Hereinafter, referring to FIG. 1, the structure of an organic electroluminescent device, and a method for preparing it will be described in detail.

FIG. 1 shows an organic electroluminescent device 100 comprising a substrate 101, a first electrode 110 formed on the substrate 101, an organic layer 120 formed on the first electrode 110, and a second electrode 130 formed on the organic layer 120 and facing the first electrode 110.

The organic layer 120 comprises a hole injection layer 122, a hole transport layer 123 formed on the hole injection layer 122, a light-emitting layer 125 formed on the hole transport layer 123, an electron buffer layer 126 formed on the light-emitting layer 125, and an electron transport zone 129 formed on the electron buffer layer 126; and the electron transport zone 129 comprises an electron transport layer 127 formed on the electron buffer layer 126, and an electron injection layer 128 formed on the electron transport layer 127.

The aforementioned description regarding the organic electroluminescent device shown in FIG. 1 is intended to explain one embodiment of the invention, and is not meant in any way to restrict the scope of the invention. The organic electroluminescent device may be constructed in another way. For example, any one optional component such as a hole injection layer may not be comprised in the organic electroluminescent device of FIG. 1, except for a light-emitting layer and an electron buffer layer. In addition, an optional component may be further comprised therein, which includes one or more of an impurity layer such as n-doping layer and p-doping layer. The organic electroluminescent device may be a both side emission type in which a light-emitting layer is placed on each of both sides of the impurity layer. The two light-emitting layers on the impurity layer may emit different colors. The organic electroluminescent device may be a bottom emission type in which a first electrode is a transparent electrode and a second electrode is a reflective electrode. The organic electroluminescent device may be a top emission type in which a first electrode is a reflective electrode and a second electrode is a transparent electrode. The organic electroluminescent device may have an inverted type structure in which a cathode, an electron transport layer, a light-emitting layer, a hole transport layer, a hole injection layer, and an anode are sequentially stacked on a substrate.

In an organic electroluminescent device comprising first and second electrodes, and a light-emitting layer, an electron buffer layer may be inserted between the light-emitting layer and the second electrode to focus on obtaining high efficiency and/or long lifespan due to electron injection controlled by the LUMO energy level of the electron buffer layer.

Figure 2:
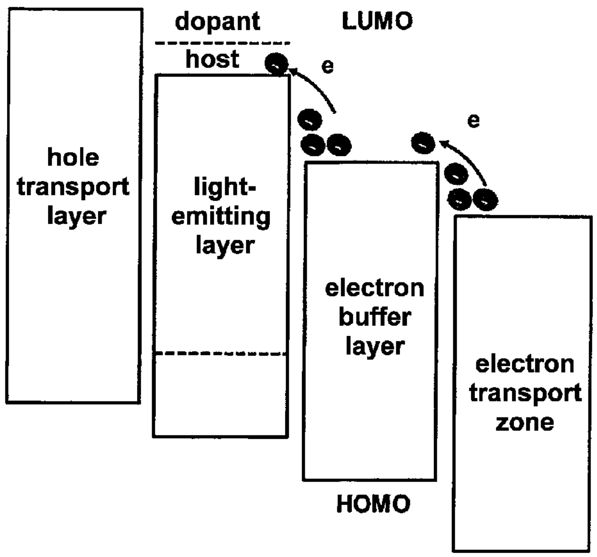
FIG. 2 illustrates an energy gap relationship among the layers of the organic electroluminescent device according to one embodiment of the present disclosure.

FIG. 2 illustrates an energy gap relationship among the layers of the organic electroluminescent device according to one embodiment of the present disclosure.

Originally, LUMO (lowest unoccupied molecular orbital) energy and HOMO (highest occupied molecular orbital) energy levels have negative values. However, for convenience, LUMO energy level (A) and HOMO energy level are expressed in absolute values in the present disclosure. In addition, the values of the LUMO energy level are compared based on absolute values.

In FIG. 2, a hole transport layer 123, a light-emitting layer 125, an electron buffer layer 126, and an electron transport zone 129 are sequentially stacked. Electrons (e−) injected from a cathode are transported to a light-emitting layer 125 through an electron transport zone 129 and an electron buffer layer 126.

The LUMO energy level of the electron buffer layer 126 has a medium value of the LUMO energy level of the host compound and the dopant compound of the light-emitting layer 125 and the LUMO energy level of the electron transport layer 127. Specifically, the LUMO energy levels of the layers have a relationship of the electron transport layer>electron buffer layer>light-emitting layer. As in FIG. 2, a LUMO energy gap of 0.5 eV or more occurs between the light-emitting layer and the electron transport layer. However, by inserting an electron buffer layer, electrons can be actively transported.

The LUMO energy levels can be easily measured by known various methods. Generally, LUMO energy levels are measured by cyclic voltammetry or ultraviolet photoelectron spectroscopy (UPS). Therefore, a person skilled in the art can easily comprehend the electron buffer layer, the host material, and electron transport zone that satisfy the equational relationship of the LUMO energy levels of the present disclosure, and practice the present disclosure. HOMO energy levels can be easily measured by the same method of measuring LUMO energy levels.

According to one embodiment of the organic electroluminescent device of the present disclosure, the LUMO energy level of the host compound (Ah) is higher than that of the dopant compound (Ad).

According to one embodiment of the organic electroluminescent device of the present disclosure, the LUMO energy level of the electron transport layer (Ae) is higher than that of the electron buffer layer (Ab). In some cases, the LUMO energy level of the electron transport layer (Ae) may be lower than that of the electron buffer layer (Ab).

According to one embodiment of the organic electroluminescent device of the present disclosure, the LUMO energy level of the electron transport layer (Ae) and that of the host compound (Ah) satisfy the following equation.

$$Ae \leq Ah + 0.5\ \text{eV}$$

For appropriate efficiency and long lifespan, preferably, the LUMO energy level of the electron transport layer (Ae) and that of the electron buffer layer (Ab) satisfy the following equation.

$$Ae \leq Ab \pm 0.2\ \text{eV}$$

The values measured by density functional theory (DFT) are used for LUMO energy levels in the present disclosure. The results according to the relationship of the LUMO energy levels of the electron transport layer (Ae), the LUMO energy levels of electron buffer layer (Ab), and the LUMO energy levels of the light-emitting layer (Ah) are for explaining the rough tendency of the device in accordance with the overall LUMO energy groups, and so results other than the above may appear according to the inherent property of the specific derivatives, and the stability of the materials.

The electron buffer layer may be comprised in organic electroluminescent devices emitting every color including blue, red, and green. Preferably, it may be comprised in an organic electroluminescent device emitting blue light (i.e. the main peak wavelength is from 430 to 470 nm, preferably, in the 450's nm).

Meanwhile, the organic electroluminescent device according to the present disclosure may comprise the well-known host and dopant compounds in the light-emitting layer. The host compound may be a phosphorescent or fluorescent host compound, and the dopant compound may be a phosphorescent or fluorescent dopant compound.

An anthracene derivative, an aluminum complex, a rubrene derivative, an arylamine derivative, or the like, preferably an anthracene derivative, may be used as the fluorescent host material.

The fluorescent host material includes the following compounds, but is not limited thereto.

BH-1

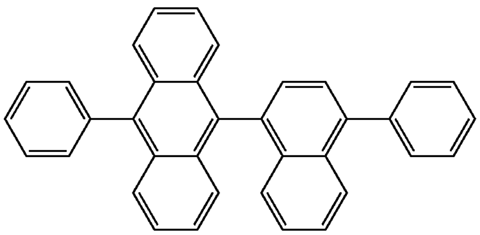

BH-2

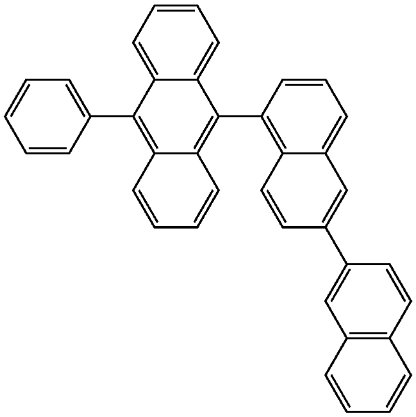

BH-3

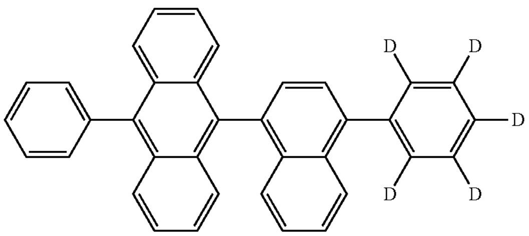

BH-4

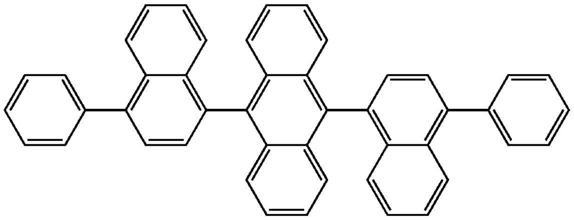

-continued

BH-5

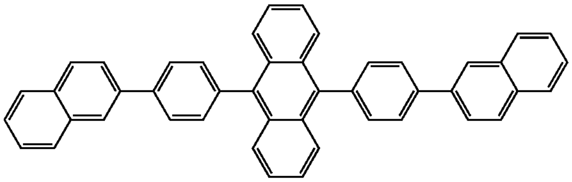

BH-6

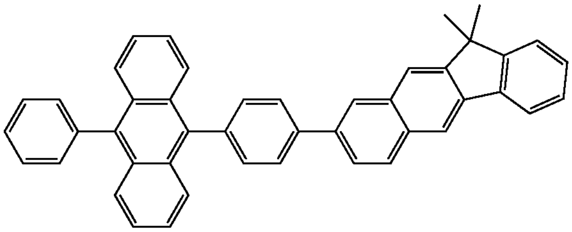

BH-7

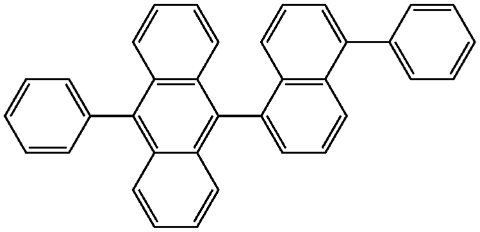

BH-8

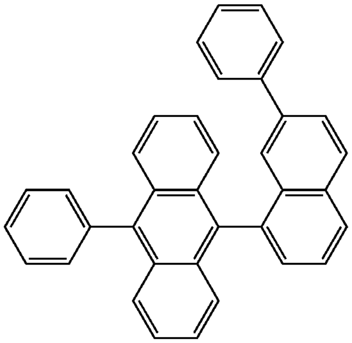

BH-9

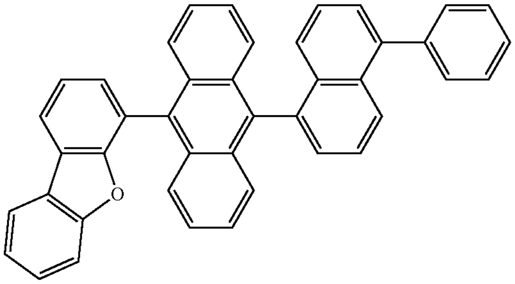

BH-10
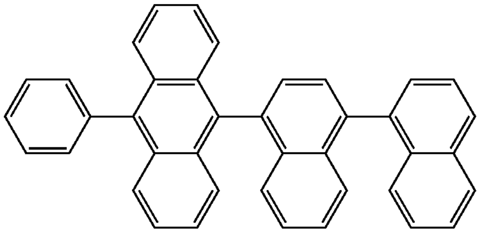
BH-11
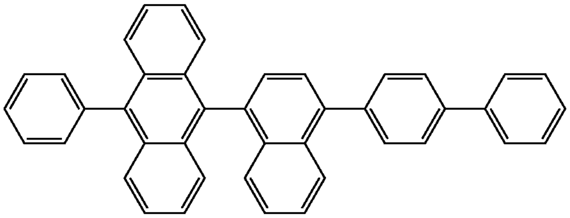
BH-12
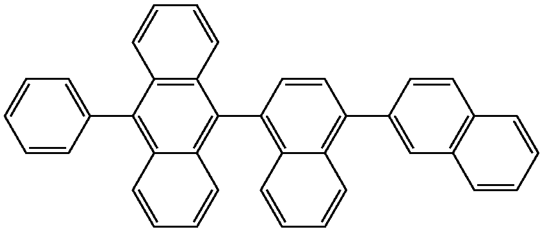
BH-13
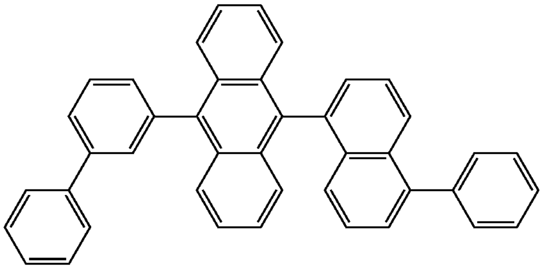
BH-14
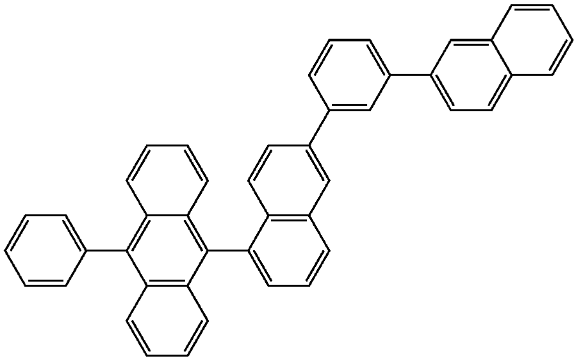
BH-15
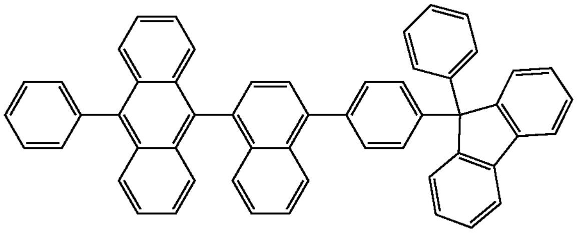
BH-16
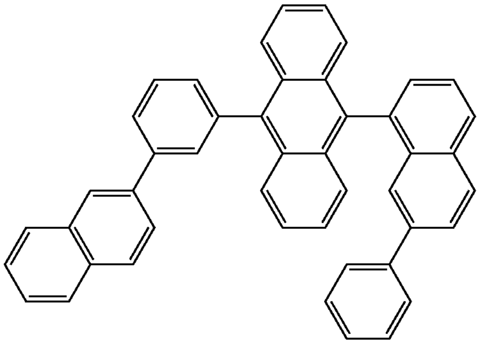
BH-17
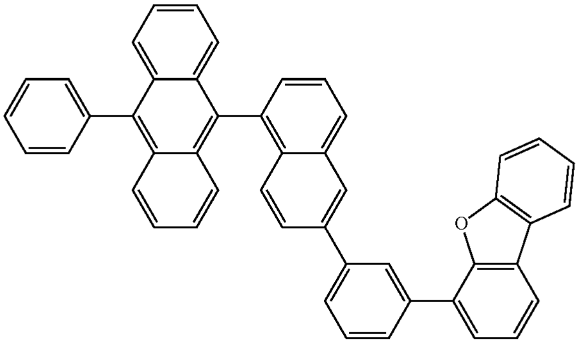
BH-18
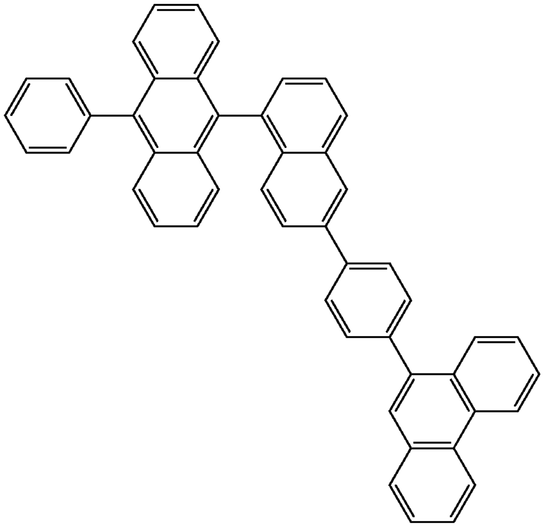

-continued

BH-19

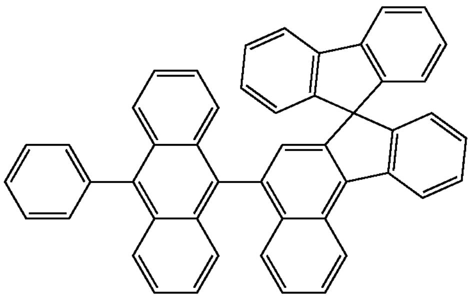

BH-20

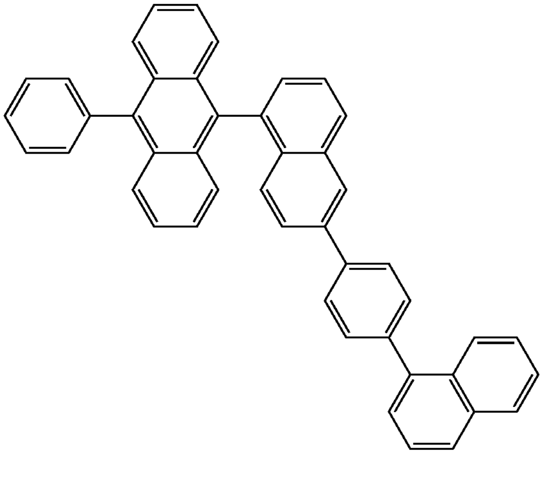

BH-21

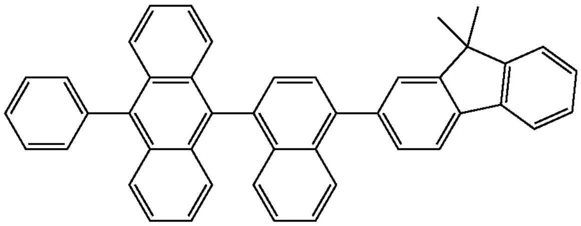

BH-22

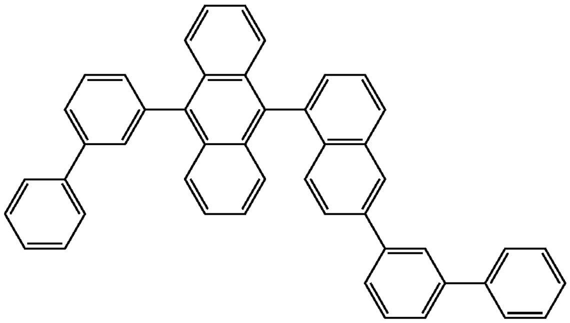

-continued

BH-23

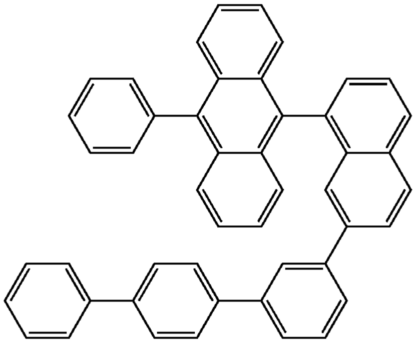

BH-24

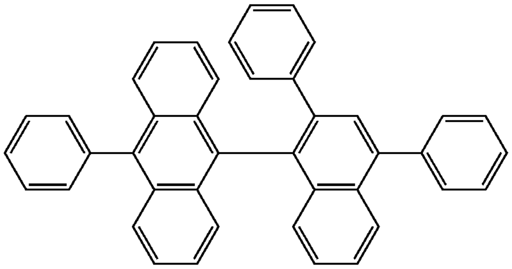

BH-25

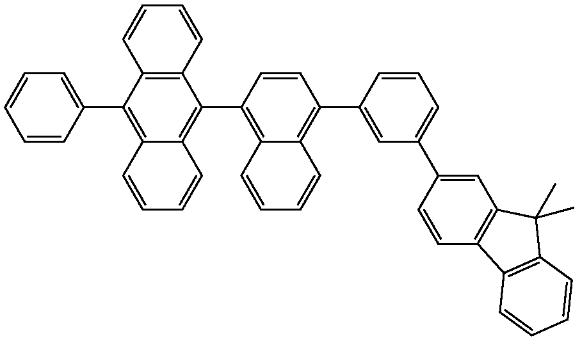

A pyrene-based derivative, an aminofluorene-based derivative, an aminoanthracene-based derivative, an aminochrysene-based derivative, or the like, preferably a pyrene-based derivative may be used as the fluorescent dopant material.

The fluorescent dopant material includes the following compounds, but is not limited thereto.

BD-1

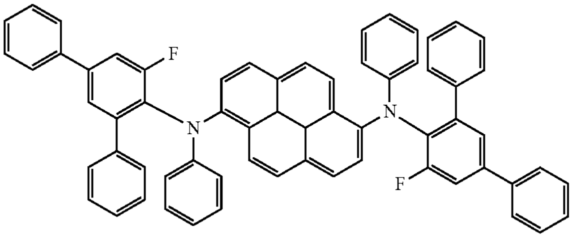

-continued
BD-2
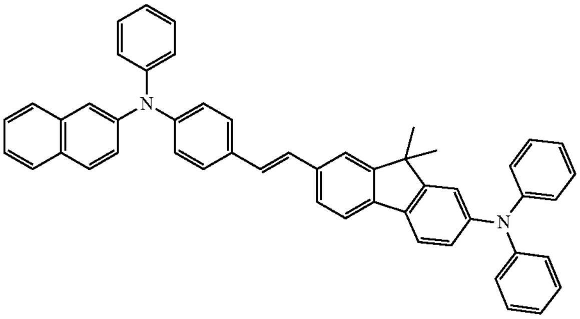
BD-3
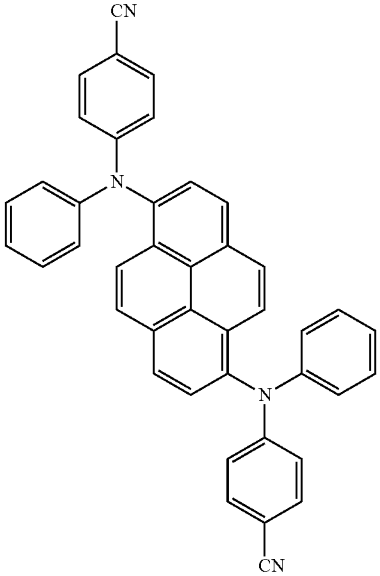
BD-4
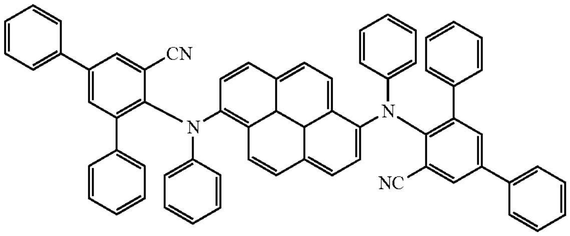
BD-5
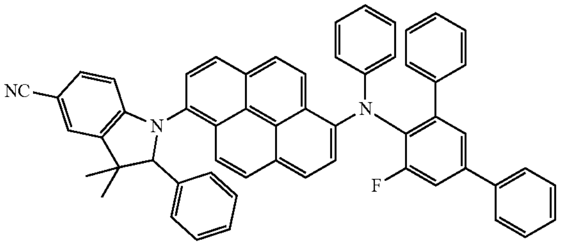
-continued
BD-6
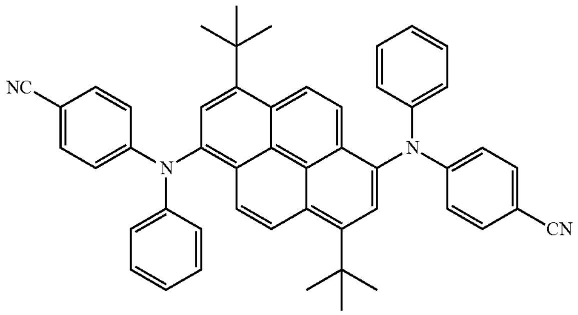
BD-7
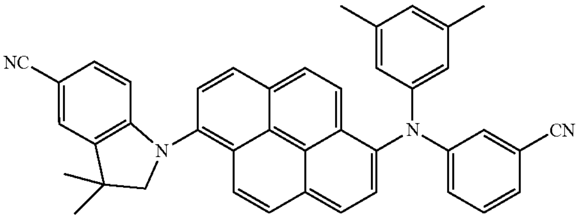
BD-8
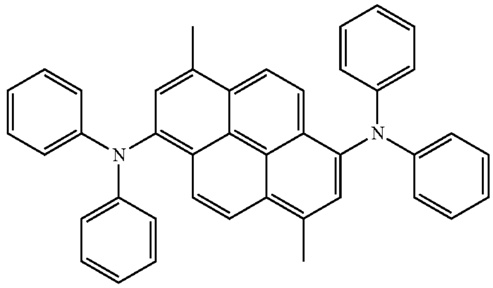
BD-9
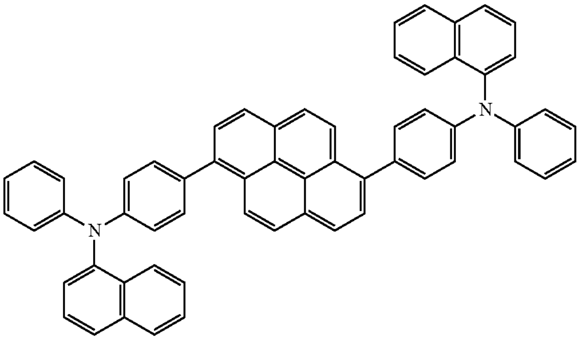
BD-10
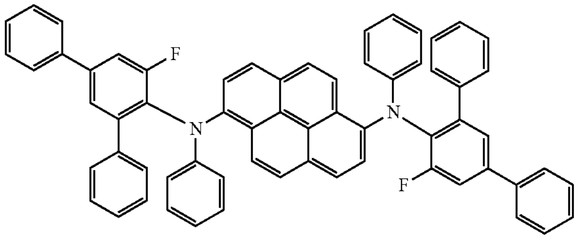

-continued

BD-11

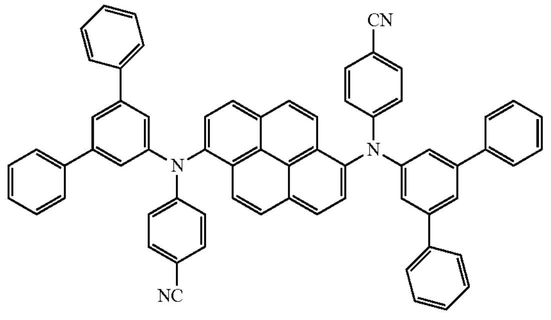

BD-12

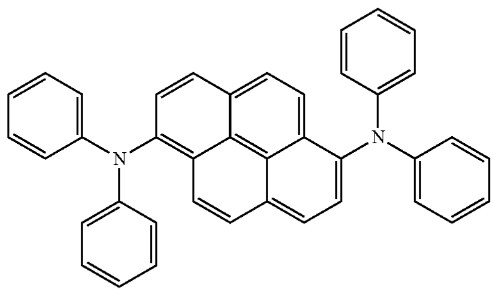

BD-13

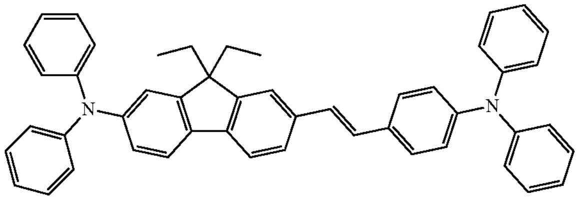

BD-14

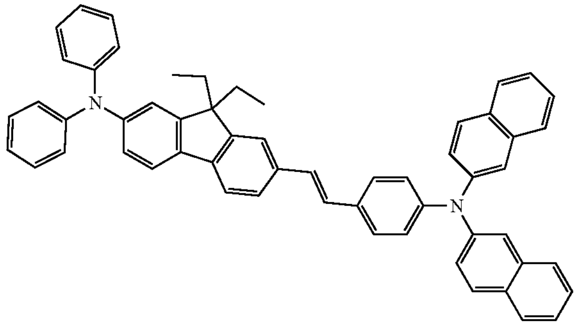

-continued

BD-15

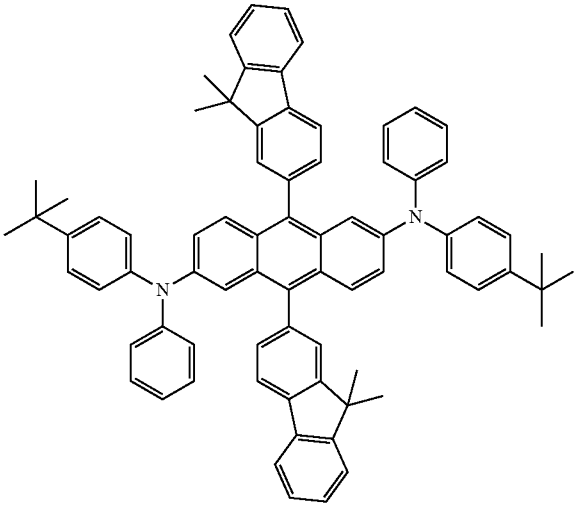

When the light-emitting layer 125 comprises a host and a dopant, the dopant may be doped in an amount of less than about 25 wt %, and preferably less than about 17 wt %, based on the total amount of the dopant and host of the light-emitting layer. The thickness of the light-emitting layer 125 may be in the range of from about 5 nm to about 100 nm, preferably, in the range of from about 10 nm to about 60 nm. The light-emitting layer 125 is a layer that emits light, and may be a single layer or two or more layers. When the light-emitting layer 125 is composed of two or more layers, each of the layers may be prepared to emit color different from one another. For example, the device may emit white light by preparing three light-emitting layers 125 which emit blue, red, and green colors, respectively. The light-emitting layer 125 may be formed on the hole transport layer 123 by using known various methods such as vacuum deposition, wet film-forming methods, laser induced thermal imaging, etc.

Also, by using the organic electroluminescent device of the present disclosure, a display system, for example, a display system for smart phones, tablets, notebooks, PCs, TVs, or cars; or a lighting system, for example, an outdoor or indoor lighting system, can be produced.

The organic electroluminescent compound represented by formulas 1 and 2 according to the present disclosure may be produced by a synthetic method known to a person skilled in the art, and, for example, referring to the following method, but is not limited thereto.

A method for synthesizing compound B-1 of formula 1 and its derivatives are disclosed in Korean Patent Application Laid-Open No. 2015-0124886 (published on Nov. 6, 2015). A method for synthesizing compound B-3 or compound B-28 of formula 1 and its derivatives are disclosed in Korean Patent Application Laid-Open No. 2015-0128590 (published on Nov. 18, 2015). A method for synthesizing compound B-9 of formula 1 and its derivatives are disclosed in Korean Patent Application Laid-Open No. 2016-0018406 (published on Feb. 17, 2016). A method for synthesizing compound B-15 of formula 1 and its derivatives are disclosed in Korean Patent Application Laid-Open No. 2016-0010333 (published on Jan. 27, 2016).

Meanwhile, compound B-19 of formula 1 and its derivatives may be synthesized by the following reaction scheme 1, but is not limited thereto.

[Reaction Scheme 1]
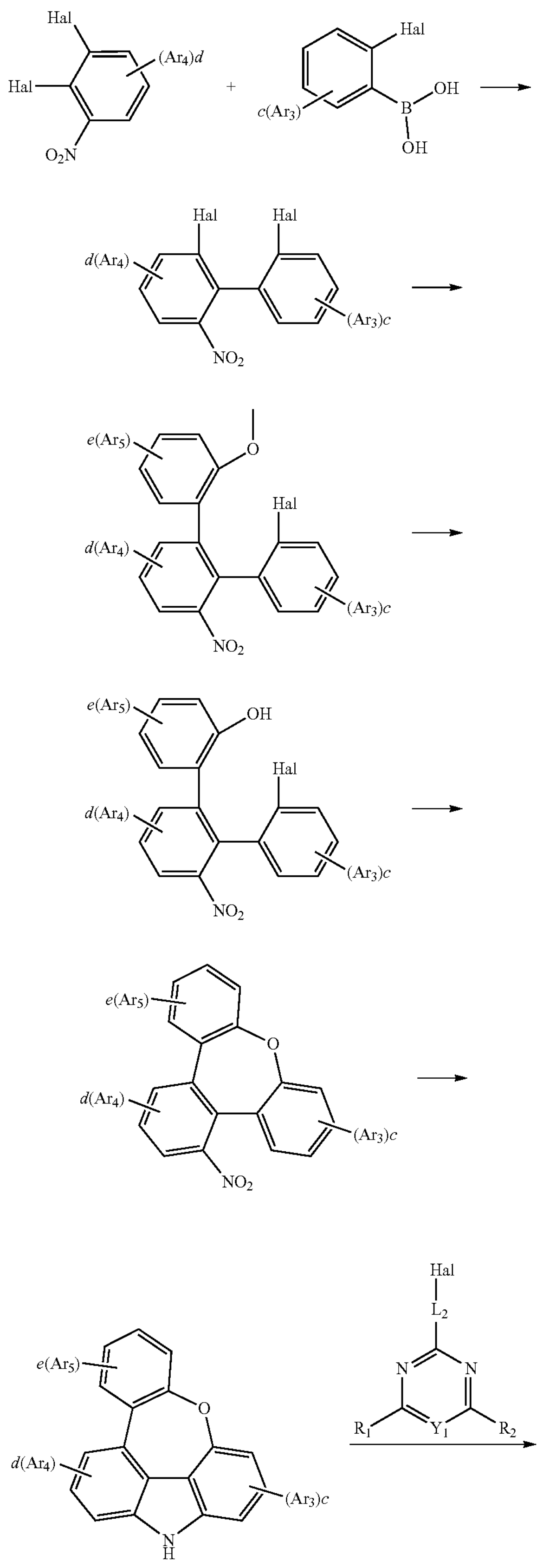
-continued
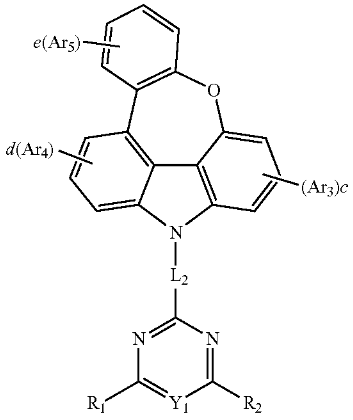
In addition, compound B-49 of formula 1 and its derivatives may be synthesized by the following Synthesis Example 1.
Synthesis Example 1
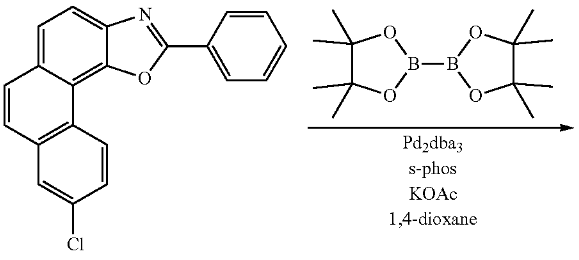
F
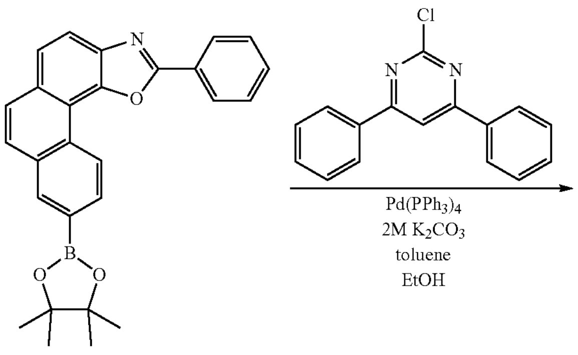
4-1

-continued

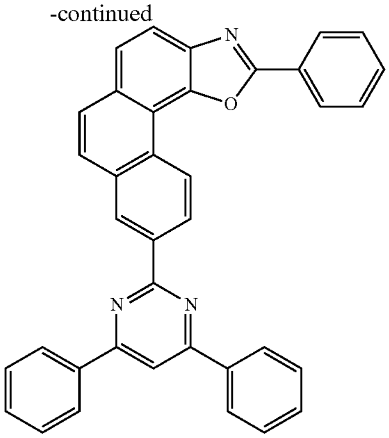

B-79

1) Preparation of Compound 4-1

After adding 7.2 g of compound F (21.8 mmol), 6.6 g of bis(pinacolato)diboran (26.2 mmol), 1.0 g of tris(dibenzylideneacetone)dipalladium (1.1 mmol), 0.89 g of 2-dicyclohexylphosphino-2',6'-dimethoxybiphenyl (s-phos) (2.2 mmol), 6.4 g of potassium acetate (65 mmol) and 150 mL of 1,4-dioxane into a reaction vessel, the mixture was stirred at 140° C. for 3 hours. After completion of the reaction, the reaction product was cooled to room temperature and extracted with ethyl acetate (EA). The extracted organic layer was dried with magnesium sulfate and the solvent was removed therefrom with a rotary evaporator. The remaining product was purified by column chromatography to obtain 5.2 g of compound 4-1 (57%).

2) Preparation of Compound B-79

After adding 5.2 g of compound 4-1 (12.3 mmol), 3.3 g of 2-chloro-4,6-diphenylpyrimidine (CAS: 2915-16-4, 12.3 mmol), 0.71 g of tetrakis(triphenylphosphine)palladium (0.62 mmol), 4.2 g of potassium carbonate (30 mmol), 60 mL of toluene, 20 mL of ethanol and 20 mL of distilled water into a reaction vessel, the mixture was stirred at 120° C. for 4 hours. After completion of the reaction, the mixture was added dropwise to methanol, and then the resultant solid was filtered. The obtained solid was purified by column chromatography and recrystallization to obtain 5.3 g of compound B-79 (82%).

In addition, compound C-1 of formula 2 and its derivatives may be synthesized by the following Synthesis Example 2.

Synthesis Example 2

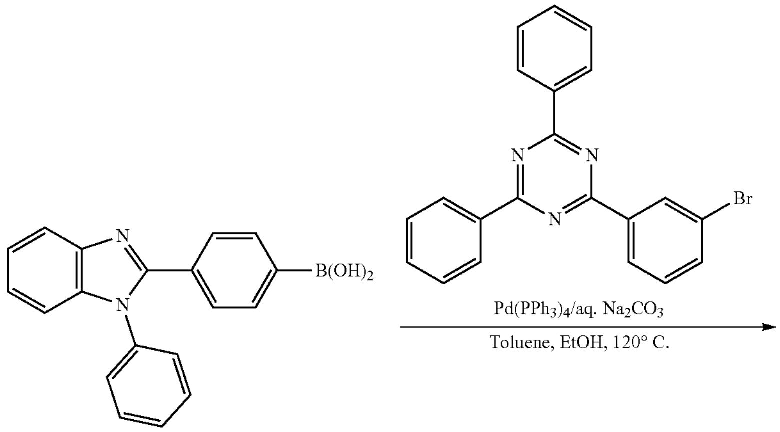

A

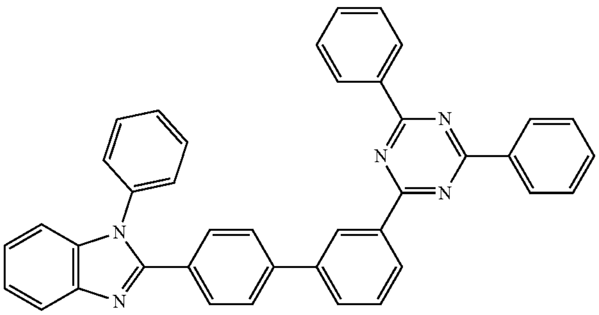

C-1

1) Preparation of Compound C-1

After adding 5.4 g of compound A (17.00 mmol), 6 g of 2-(3-bromophenyl)-4,6-diphenyl-1,3,5-triazine (15.45 mmol), 0.6 g of tetrakis(triphenylphosphine)palladium (0.46 mmol), 4.1 g of sodium carbonate (38.63 mmol), 78 mL of toluene, and 19 mL of ethanol into a reaction vessel, 19 mL of distilled water was then added. The mixture was stirred at 120° C. for 6 hours. After completion of the reaction, the reaction product was washed with distilled water and extracted with ethyl acetate. The extracted organic layer was dried with magnesium sulfate and the solvent was removed therefrom with a rotary evaporator. The remaining product was purified by column chromatography to obtain 5.5 g of compound C-1 (yield: 62%).

| | MW | UV | PL | M.P. |
|---|---|---|---|---|
| C-1 | 577.68 | 356 nm | 389 nm | 282° C. |

Hereinafter, the luminescent properties of the organic light-emitting diode (OLED) device comprising the compound according to the present disclosure in the electron transport layer and the electron buffer layer, and the OLED device comprising compounds not according to the present disclosure in the electron transport layer or the electron buffer layer will be explained in detail. However, the following examples merely illustrate the characteristics of the OLED device according to the present invention for a detailed understanding of the present disclosure, but the present disclosure is not limited by the following examples.

Comparative Example 1: Producing a Blue Light-Emitting OLED Device not According to the Present Disclosure An OLED device not according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. The ITO substrate was mounted on a substrate holder of a vacuum vapor deposition apparatus. Compound HI-1 was introduced into a cell of the vacuum vapor deposition apparatus, and then the pressure in the chamber of the apparatus was then controlled to $10^{-7}$ torr. Thereafter, an electric current was applied to the cell to evaporate the above-introduced material, thereby forming a first hole injection layer having a thickness of 60 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 20 nm on the second hole injection layer. Compound HT-2 was then introduced into another cell of the vacuum vapor deposition apparatus and was evaporated by applying an electric current to the cell, thereby forming a second hole transport layer having a thickness of 5 nm on the first hole transport layer. After forming the hole injection layers and the hole transport layers, a light-emitting layer was formed thereon as follows: Compound BH-1 was introduced into one cell of the vacuum vapor depositing apparatus as a host, and compound BD-1 was introduced into another cell as a dopant. The two materials were evaporated at a different rate and the dopant was deposited in a doping amount of 2 wt % based on the total amount of the host and dopant to form a light-emitting layer having a thickness of 20 nm on the second hole transport layer. Compound ETL-1 as an electron transport material was then introduced into one cell of the vacuum vapor deposition apparatus and evaporated to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED device was produced. All the materials used for producing the OLED device were purified by vacuum sublimation at $10^{-6}$ torr.

Figure 3:
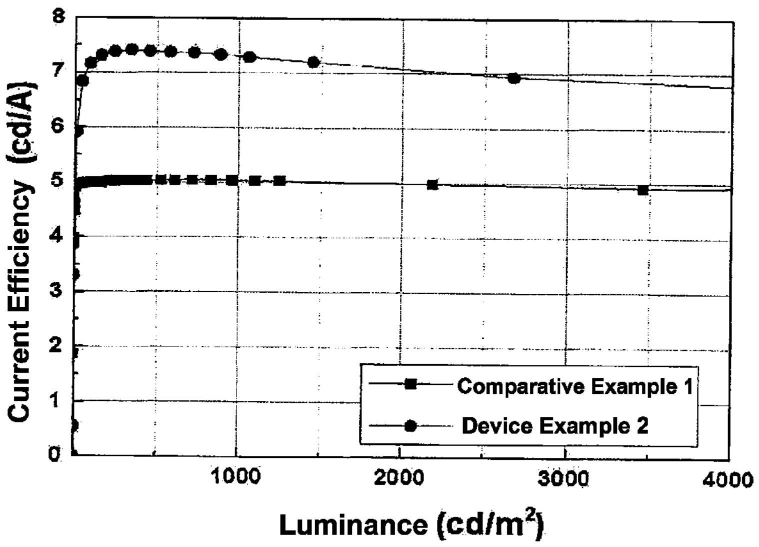
FIG. 3 is a graph illustrating a current efficiency versus a luminance of organic electroluminescent devices according to the present disclosure and not according to the present disclosure.

The driving voltage, luminous efficiency, CIE color coordinates, and the time taken to be reduced from 100% to 50% of the luminance (lifespan; T50) based on a luminance of 1,000 nits of the produced OLED device are provided in Table 1 below. In Table 1, the electron buffer material and the electron transport material refer to the compound comprised in the electron buffer layer and the electron transport layer, respectively. In addition, a current efficiency versus a luminance of the organic electroluminescent device of Comparative Example 1 is illustrated in FIG. 3 as a graph.

Comparative Example 2: Producing a Blue Light-Emitting OLED Device not According to the Present Disclosure An OLED device was produced in the same manner as in Comparative Example 1, except for using compound ETL-2 as an electron transport material. The evaluation results of the OLED device of Comparative Example 2 were provided in Table 1 below.

Comparative Examples 3 and 4: Producing a Blue Light-Emitting OLED Device not According to the Present Disclosure OLED devices were produced in the same manner as in Comparative Example 1, except that the thickness of the electron transport layer was reduced to 30 nm, the electron buffer layer was inserted between the light-emitting layer and the electron transport layer, and the electron buffer material and the electron transport material were used as described in Table 1 below. Specifically, in Comparative Example 3, compound ETL-1 as an electron buffer material was deposited on the light-emitting layer to form an electron buffer layer having a thickness of 5 nm, and then compound ETL-2 as an electron transport material was deposited on the electron buffer layer to form an electron transport layer having a thickness of 30 nm. In Comparative Example 4, compound B-21 as an electron buffer material was deposited on the light-emitting layer to form an electron buffer layer having a thickness of 5 nm, and then compound ETL-3 and compound ETL-1 were evaporated at the same rate and doped in a weight ratio of 60:40 to form an electron transport layer having a thickness of 30 nm on the electron buffer layer. The evaluation results of the OLED device of Comparative Examples 3 and 4 were provided in Table 1 below.

Device Examples 1 to 3: Producing a Blue Light-Emitting OLED Device According to the Present Disclosure OLED devices were produced in the same manner as in Comparative Example 4, except that compound C-3 and compound EIL-1 were introduced into one cell and another cell of the vacuum vapor depositing apparatus, respectively, as an electron transport material as shown in Table 1 below, evaporated at the same rate, and doped in a weight ratio of 60:40 to form an electron transport layer having a thickness of 30 nm; and an electron buffer material was used as shown in Table 1 below. The evaluation results of the OLED device of Device Examples 1 to 3 are provided in Table 1 below. In addition, a current efficiency versus a luminance of the organic electroluminescent device of Device Example 2 is illustrated in FIG. 3 as a graph.

TABLE 1

| | Electron Buffer Material | Electron Transport Material | Driving Voltage (V) | Luminous Efficiency (cd/A) | Color Coordinate (x) | Color Coordinate (y) | Lifespan (T50, hr) |
|---|---|---|---|---|---|---|---|
| Comparative Example 1 | — | ETL-1 | 5.8 | 5.0 | 0.140 | 0.095 | 14.6 |
| Comparative Example 2 | — | ETL-2 | 4.6 | 4.3 | 0.144 | 0.105 | 213.8 |
| Comparative Example 3 | ETL-1 | ETL-2 | 5.2 | 4.2 | 0.141 | 0.097 | 36.5 |
| Comparative Example 4 | B-21 | ETL-3:EIL-1 (6:4) | 3.9 | 5.9 | 0.140 | 0.099 | 315.5 |
| Device Example 1 | B-21 | | 4.1 | 6.0 | 0.139 | 0.097 | 399.7 |
| Device Example 2 | B-2 | C-3:EIL-1 (6:4) | 3.9 | 7.2 | 0.139 | 0.098 | 294.8 |
| Device Example 3 | B-28 | | 3.9 | 6.9 | 0.139 | 0.097 | 331.5 |

Comparative Examples 5 to 10: Producing a Blue Light-Emitting OLED Device not According to the Present Disclosure Comparative Examples 5 and 6 were produced in the same manner as in Comparative Example 1, Comparative Example 7 was produced in the same manner as in Comparative Example 3, and Comparative Examples 8 to 10 were produced in the same manner as in Comparative Example 4, except that compound BH-2 instead of compound BH-1 was comprised as the host; and the electron buffer material and the electron transport material were used as shown in Table 2 below. The driving voltage, luminous efficiency, CIE color coordinates, and the time taken to be reduced from 100% to 70% of the luminance (lifespan; T70) based on a luminance of 1,000 nits of the produced OLED device are provided in Table 2 below.

Device Examples 4 to 6: Producing a Blue Light-Emitting OLED Device According to the Present Disclosure OLED devices were produced in the same manner as in Comparative Examples 8 to 10, except that compound C-1 and compound EIL-1 were introduced into one cell and another cell of the vacuum vapor depositing apparatus, respectively, as an electron transport material as shown in Table 2 below, evaporated at the same rate, and doped in a weight ratio of 60:40 to form an electron transport layer having a thickness of 30 nm. The evaluation results of the OLED device of Device Examples 4 to 6 are provided in Table 2 below.

TABLE 2

| | Electron Buffer Material | Electron Transport Material | Driving Voltage (V) | Luminous Efficiency (cd/A) | Color Coordinate (x) | Color Coordinate (y) | Lifespan (T70, hr) |
|---|---|---|---|---|---|---|---|
| Comparative Example 5 | — | ETL-1 | 6.4 | 4.7 | 0.140 | 0.089 | 1.45 |
| Comparative Example 6 | — | ETL-2 | 5.2 | 4.0 | 0.146 | 0.105 | 67.2 |
| Comparative Example 7 | ETL-1 | ETL-2 | 5.8 | 4.0 | 0.141 | 0.091 | 6.5 |
| Comparative Example 8 | C-1 | | 4.4 | 5.9 | 0.139 | 0.090 | 290.7 |
| Comparative Example 9 | B-2 | (ETL-3:EIL-1) (5:5) | 4.3 | 6.6 | 0.139 | 0.090 | 211.2 |
| Comparative Example 10 | B-28 | | 4.4 | 6.3 | 0.139 | 0.091 | 250.7 |
| Device Example 4 | C-1 | | 4.4 | 6.0 | 0.139 | 0.087 | 336.0 |
| Device Example 5 | B-2 | (C-1:EIL-1) (6:4) | 4.2 | 6.6 | 0.139 | 0.087 | 273.5 |
| Device Example 6 | B-28 | | 4.3 | 6.2 | 0.139 | 0.087 | 334.4 |

From Tables 1 and 2 above, it can be seen that the OLED devices of Device Examples 1 to 6 provide lower driving voltage, higher efficiency, and/or longer lifespan compared to the Comparative Examples, by appropriately combining the compounds comprised in the electron buffer layer and the electron transport layer of the present disclosure. In particular, the OLED device according to the present disclosure may be useful for flexible displays, lightings and vehicle displays which require long lifespan.

Characteristic Analysis

In order to predict the electron mobility characteristic of the 3,4-biphenyl linker according to the present disclosure, the reorganization energy value (A) of the Marcus Theory was confirmed by the calculation of DFT (Density Functional Theory). Electron mobility enhancement may be one of the conditions to provide a good electron transport layer. In particular, for the smooth electron transport in an organic electroluminescent device, collision or interference between neighboring molecules must be small and charge transfer speed must be increased. This charge transfer model is well described in Marcus Theory. According to the following equation 1, the speed of moving the carrier may be quantified by the reorganization energy value (λ). The reorganization energy value (λ) may be classified to the energy required to insert one electron as λ−, and the energy required to insert one hole as λ+. This reorganization energy is directly related to the carrier mobility, which can be determined by DFT calculation. In the present disclosure, the reorganization energy value (λ−) for the electron is calculated due to the importance of the characterization of the electron mobility. That is, the smaller the energy value λ− is the more easily eliminating the electrons. The Marcus Theory can be expressed by Equation 1 below.

$$K_{h/e}=\left(\frac{\pi}{\lambda_{h/e}kT}\right)^{1/2}\times\frac{V_{h/e}^{2}}{\hbar}\times\exp\left(-\frac{\lambda_{h/e}}{4kT}\right) \quad \text{[Equation 1]}$$

Wherein, $K_{h/e}$ is a charge transfer rate, T is an absolute temperature, k and h are the Boltzmann constant and the Planck constant, respectively, $A_{h/e}$ is a reorganization energy, and V is an electron coupling matrix element (see J. Phys. Chem. A, Vol. 114, No. 10, 2010 3657).

TABLE 3

| Electron Transport Material | λ− |
|---|---|
| C-1 | 0.225 |
| C-2 | 0.237 |
| C-3 | 0.222 |
| C-4 | 0.247 |
| ETL-4 | 0.474 |
| ETL-5 | 0.441 |
| ETL-6 | 0.475 |

According to Table 3 above, a substituted heteroaryl compound which is linked with an imidazole via 3,4-biphenyl as a linker in the electron transport layer (compounds C-1 to C-4) have a low energy value of λ−, which is the energy required to insert an electron, as 0.2's, and it enables injecting electrons efficiently. Thus, excellent results could be obtained as an electron transport layer. While, when the linker position of biphenyl is in the 4,4-position (compound ETL-4) rather than the 3,4-position (compound C-1), the corresponding energy value is 0.225 to 0.474, which result in the increase of the energy value λ− as about two times.

In order to compare and verify the above characteristics, the luminescent characteristics of the OLED devices comprising compound C-2 having the low energy value of λ− and compound ELT-4 having the high energy value of λ− were compared. The OLED device was produced in the same manner as in Comparative Example 1, except that compound ETL (compound C-2 or compound ETL-4) and compound EIL-1 in a weight ratio of 50:50 were deposited on the light-emitting layer to a thickness of 35 nm. As a result, when compound C-2 was comprised, the efficiency was 6.0 cd/A at a driving voltage of 3.9 V, and 1000 nits of blue light-emission was observed. On the contrast, when compound ETL-4 was comprised, the efficiency was 4.4 cd/A at a driving voltage of 4.5 V, and 1000 nits of blue light-emission was observed. From this result, it was confirmed that the materials having the 3,4-biphenyl linker had a low reorganization energy value, which enables providing an OLED device having a low driving voltage and a relatively high efficiency based on faster mobility characteristic.

TABLE 4

| Compounds used in Comparative Examples and Device Examples | |
|---|---|
| Hole Injection Layer/ Hole Transport Layer | 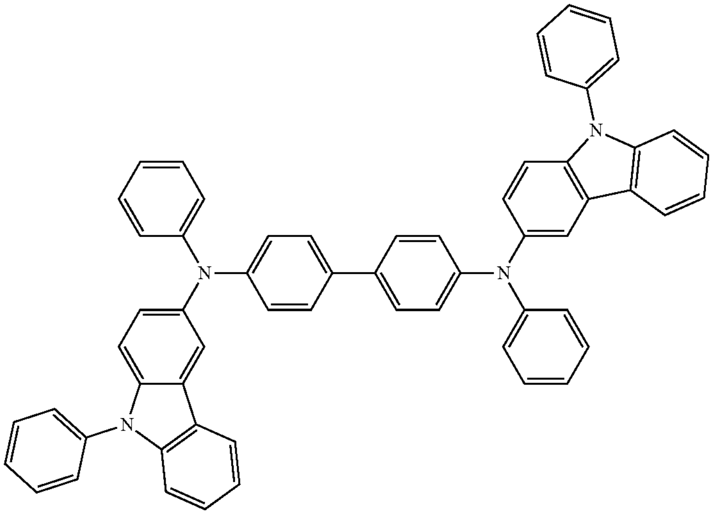 HI-1 |

TABLE 4-continued
| Compounds used in Comparative Examples and Device Examples |
| --- |
| 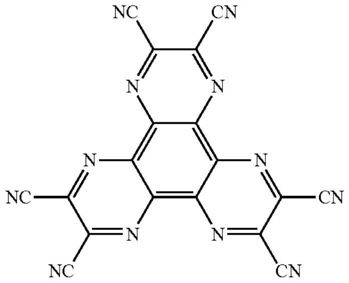<br>HI-2 |
| 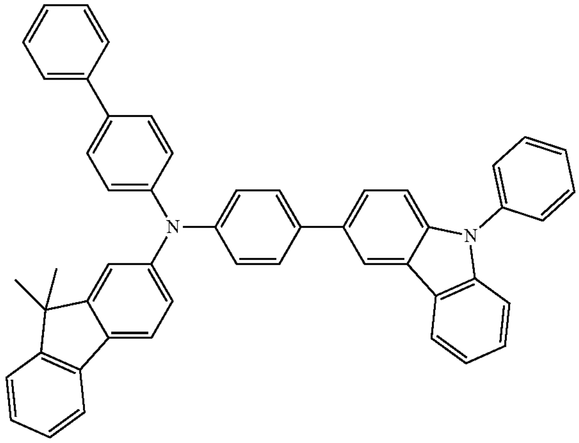<br>HT-1 |
| 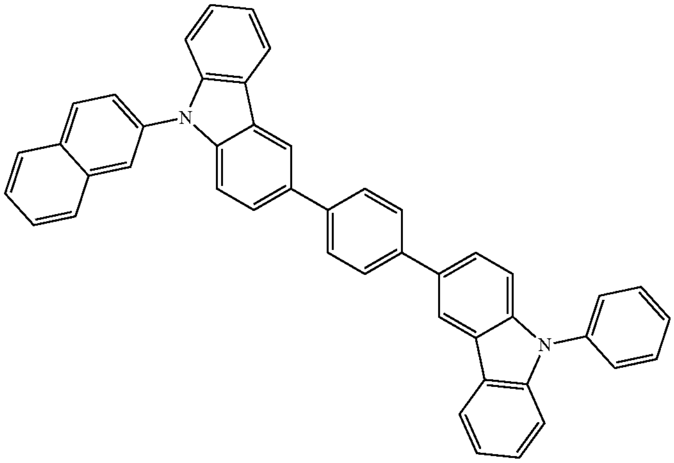<br>HT-2 |

TABLE 4-continued
| Compounds used in Comparative Examples and Device Examples | |
|---|---|
| Light-Emitting Layer | 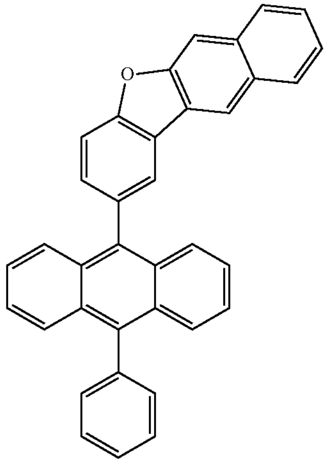 BH-1 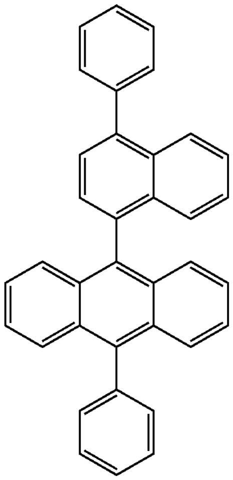 BH-2 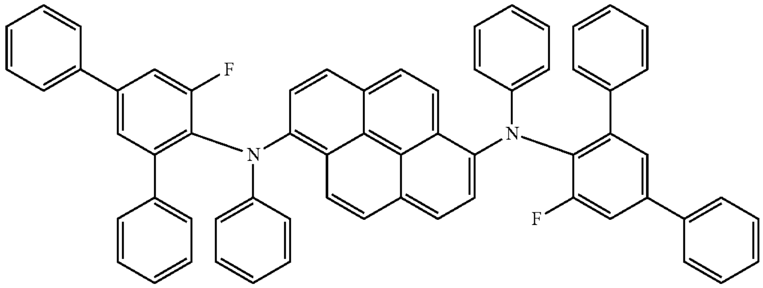 BD-1 |
| Electron Buffer Layer/ Electron Transport Layer/ Electron Injection Layer | 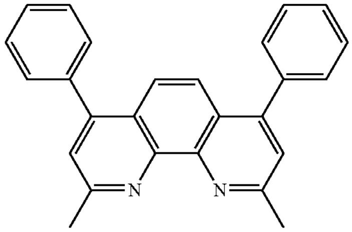 ETL-1 |

TABLE 4-continued
| Compounds used in Comparative Examples and Device Examples |
| --- |
| 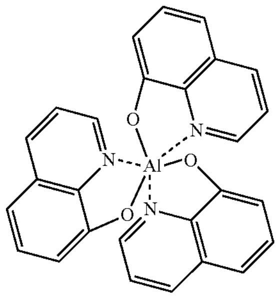<br>RTL-2 |
| 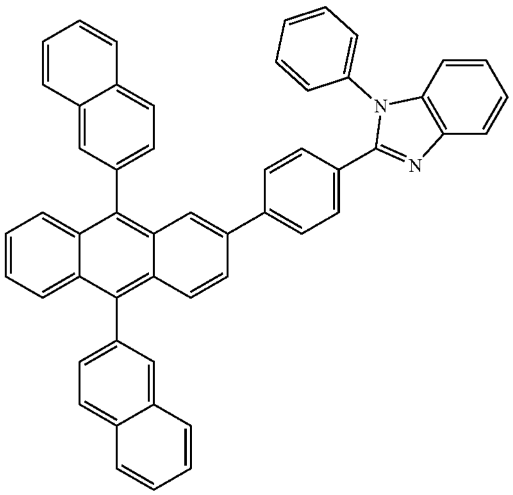<br>ETL-3 |
| 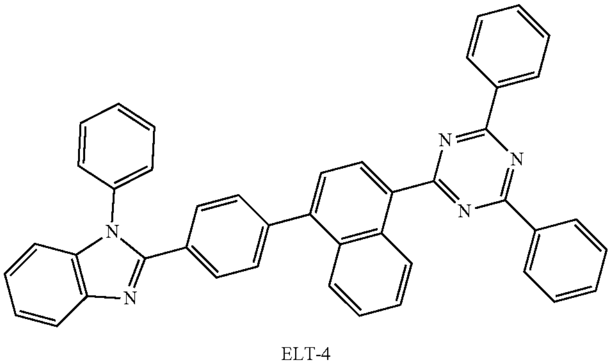 [SMILES: c1ccc(-c2nc(-c3ccccc3)nc(-c3ccc(-c4ccc(-c5nc6ccccc6n5-c5ccccc5)cc4)c4ccccc34)n2)cc1]<br>ELT-4 |

TABLE 4-continued
| Compounds used in Comparative Examples and Device Examples |
| --- |
| 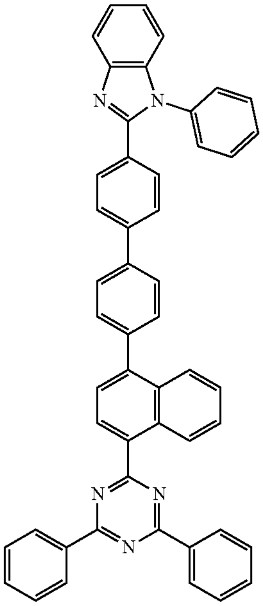<br>ELT-5 |
| 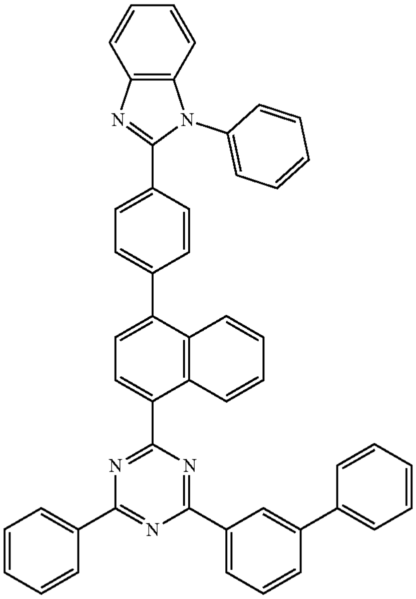<br>ELT-6 |
| 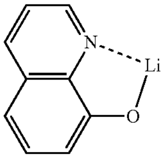<br>EIL-1 |

| Reference Numbers | |
|---|---|
| 100: organic electroluminescent device | 101: substrate |
| 110: first electrode | 120: organic layer |
| 122: hole injection layer | 123: hole transport layer |
| 125: light-emitting layer | 126: electron buffer layer |
| 127: electron transport layer | 128: electron injection layer |
| 129: electron transport zone | 130: second electrode |

The invention claimed is:

1. An organic electroluminescent device comprising a first electrode, a second electrode facing the first electrode, a light-emitting layer between the first electrode and the second electrode, and an electron transport layer and an electron buffer layer between the light-emitting layer and the second electrode, wherein the electron buffer layer comprises at least one of the compound represented by the following formula 1 and the compound represented by the following formula 2, and the electron transport layer comprises a compound represented by the following formula 2:

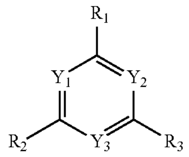
(1)

wherein $Y_1$ to $Y_3$, each independently, represent N or $CR_4$, with a proviso that at least two of $Y_1$ to $Y_3$ represent N, and $R_1$ to $R_4$, each independently, represent hydrogen, a halogen, a substituted or unsubstituted (C1-C30)alkyl, a substituted or unsubstituted (C6-C60)aryl, or a substituted or unsubstituted (3- to 60-membered)heteroaryl, or $R_4$ may be linked to one of $R_1$ to $R_3$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, wherein $R_1$ to $R_3$ not linked with $R_4$ have the above definition, with a proviso that all of $R_1$ to $R_3$ are not hydrogen;

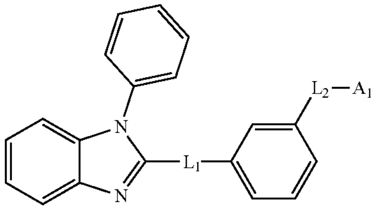
(2)

wherein $L_1$ represents a substituted or unsubstituted (C6-C30) arylene, $L_2$ represents a single bond, or a substituted or unsubstituted (C6-C30)arylene, $A_1$ represents a substituted or unsubstituted (3- to 30-membered)heteroaryl, and the heteroaryl contains at least one heteroatom selected from B, N, O, S, Si, and P.

2. The organic electroluminescent device according to claim 1, wherein formula 1 is represented by any one of the following formulas 3 to 5:

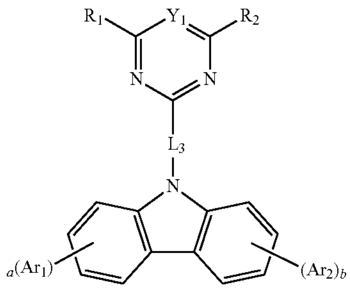
(3)

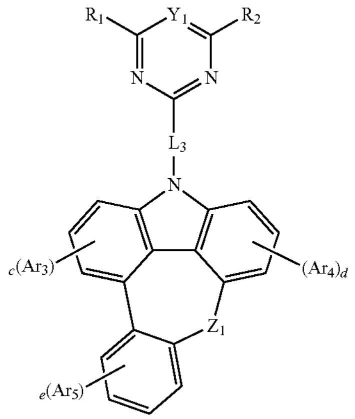
(4)

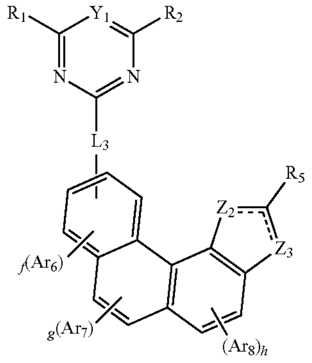
(5)

wherein $Y_1$ represents N or $CR_4$, $R_1$, $R_2$ and $R_4$, each independently, represent hydrogen, a halogen, a substituted or unsubstituted (C1-C30)alkyl, a substituted or unsubstituted (C6-C30)aryl, or a substituted or unsubstituted (3- to 30-membered)heteroaryl, or $R_4$ may be linked to $R_1$ or $R_2$ to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, wherein $R_1$ and $R_2$ not linked with $R_4$ have the above definition, $L_3$ represents a single bond, a substituted or unsubstituted (C6-C30)arylene, or a substituted or unsubstituted (3- to 30-membered)heteroarylene, $Z_1$ represents O, S, $NR_7$ or $CR_8C_9$, any one of $Z_2$ and $Z_3$ represents =N— or =$CR_{10}$—, the other of $Z_2$ and $Z_3$ represents O, S, $NR_{11}CR_{12}R_{13}$, $Ar_1$ to $Ar_8$, $R_5$, and $R_7$ to $R_{13}$, each independently, represent hydrogen, deuterium, a halogen, a cyano, a carboxyl, a nitro, a hydroxyl, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C3-C30)cycloalkenyl, —$NR_{14}R_{15}$ or $SiR_{16}R_{17}R_{18}$, or may be linked to an adjacent substituent to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur, $R_{14}$ to $R_{15}$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered) heteroaryl, a, b, and e, each independently, represent an integer of 1 to 4; c, d and f, each independently, represent an integer of 1 to 3; g and h, each independently, represent 1 or 2; where if a to h, each independently, are an integer of 2 or more, each of $Ar_1$ to $Ar_8$ may be the same or different, and the heteroaryl(ene) contains at least one heteroatom selected from B, N, O, S, Si, and P.

3. The organic electroluminescent device according to claim 1, wherein formula 2 is represented by the following formula 9:

(9)

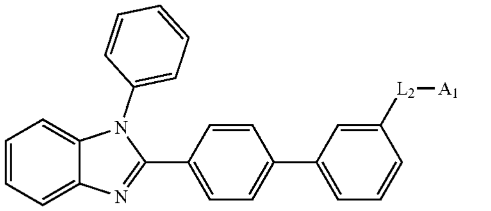

wherein $L_2$ represents a single bond, or a substituted or unsubstituted (C6-C30)arylene, and $A_1$ represents any one of the following formula 10 or 11:

(10)

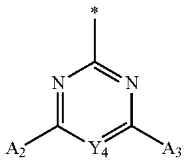

(11)

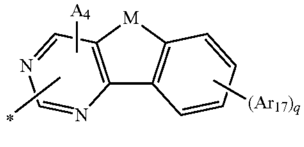

wherein

*represents a bonding site with $L_2$ of formula 9, $Y_4$ represents N or $CR_{19}$, M represents O or S, $A_2$ to $A_4$, $R_{19}$ and $Ar_{17}$, each independently, represent hydrogen, a substituted or unsubstituted (C1-C30)alkyl, a substituted or unsubstituted (C6-C30)aryl, or a substituted or unsubstituted (3- to 30-membered)heteroaryl, q represents an integer of 1 to 4, and the heteroaryl contains at least one heteroatom selected from B, N, O, S, Si, and P.

4. The organic electroluminescent device according to claim 1, wherein the substituents of the substituted alkyl, the substituted aryl(ene), the substituted heteroaryl, and the substituted mono- or polycyclic, alicyclic or aromatic ring, or the combination thereof, in $R_1$ to $R_4$, $L_1$, $L_2$ and $A_1$, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (C6-C30)aryl, a (5- to 30-membered)heteroaryl unsubstituted or substituted with a (C1-C30)alkyl or a (C6-C30)aryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

5. The organic electroluminescent device according to claim 1, wherein the compound represented by formula 1 is selected from the group consisting of:

B-1

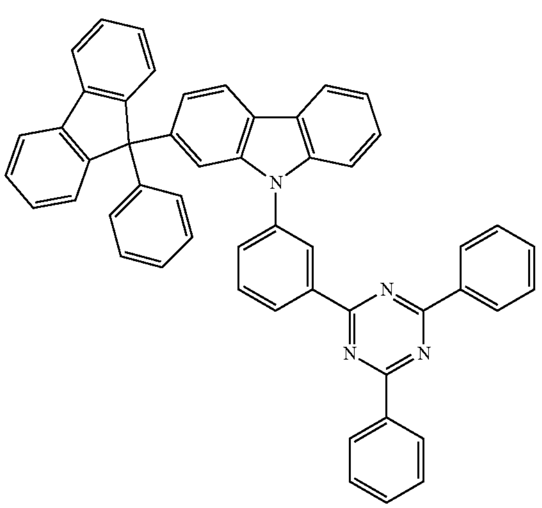

-continued
B-2
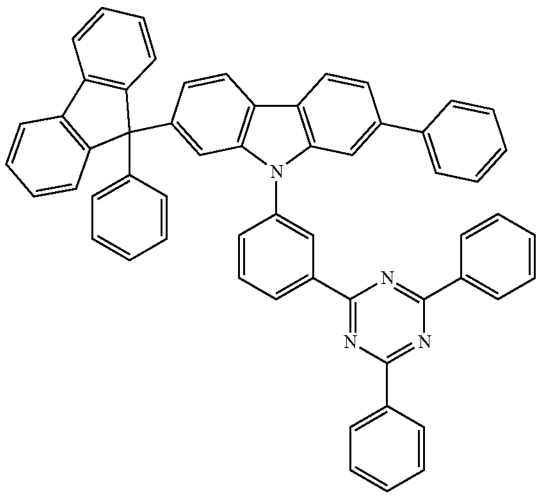
B-3
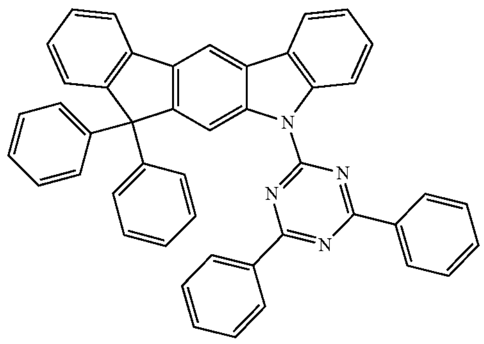
B-4
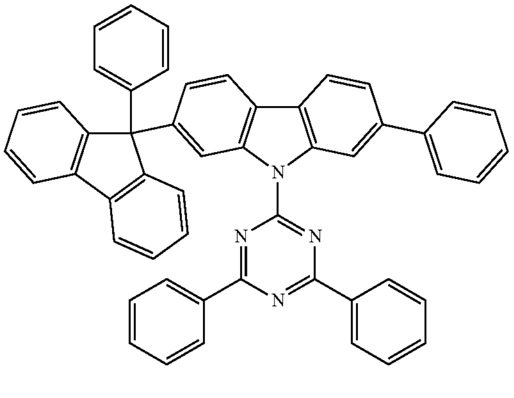
-continued
B-5
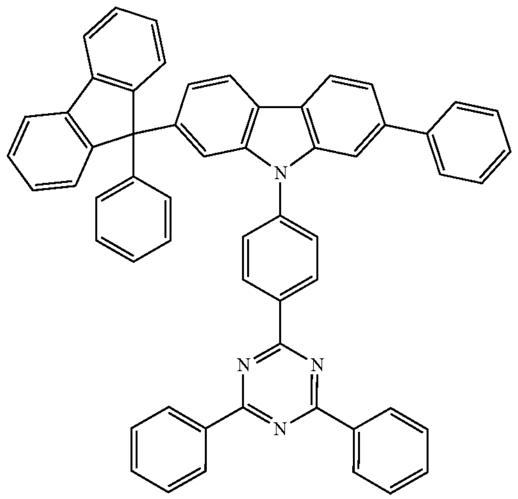
B-6
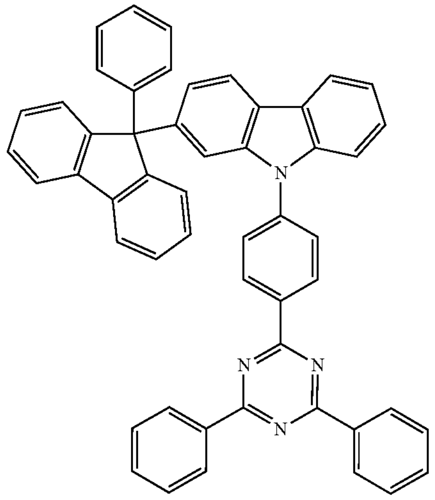
B-7
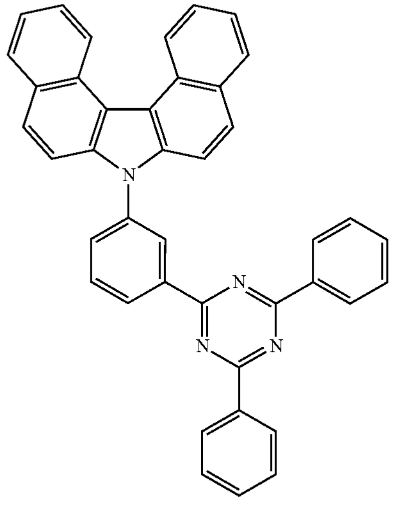

-continued
B-8
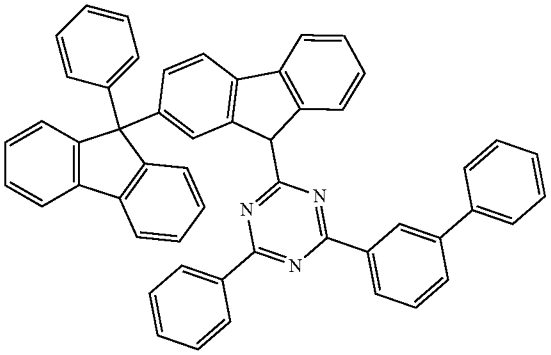
B-9
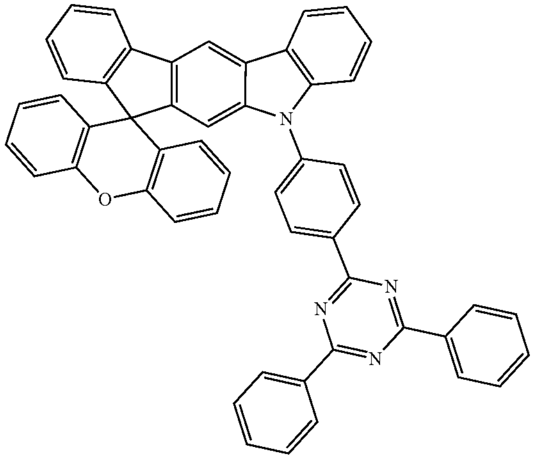
B-10
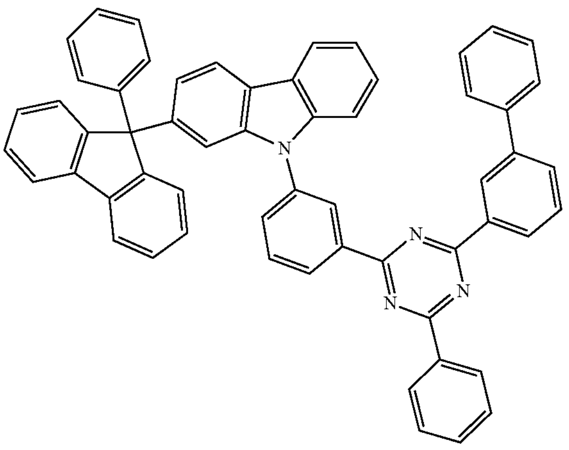
-continued
B-11
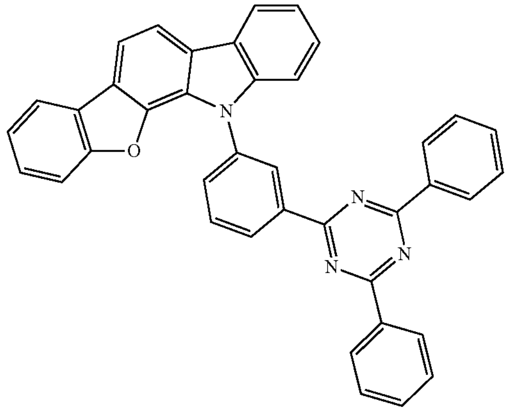
B-12
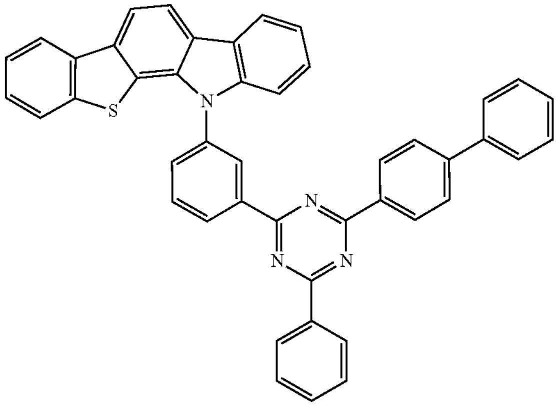
B-13
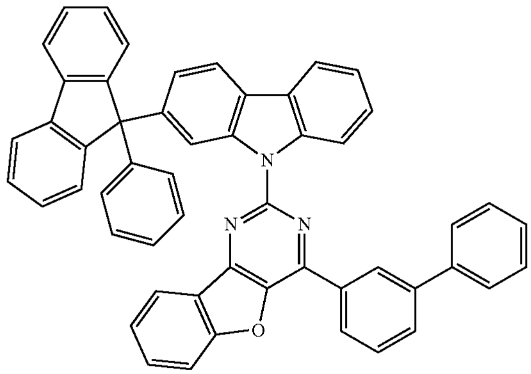

-continued
B-14
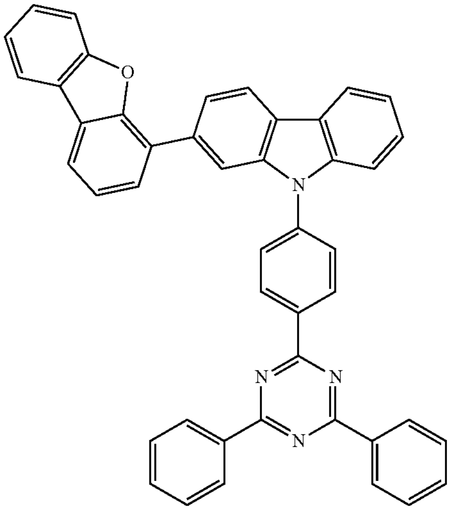
B-15
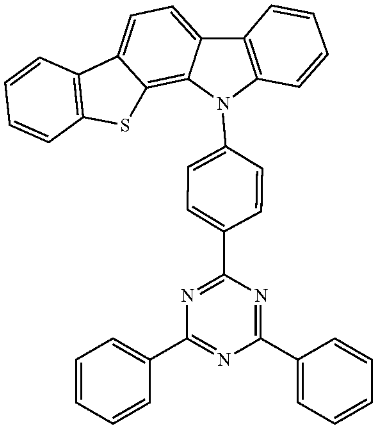
B-16
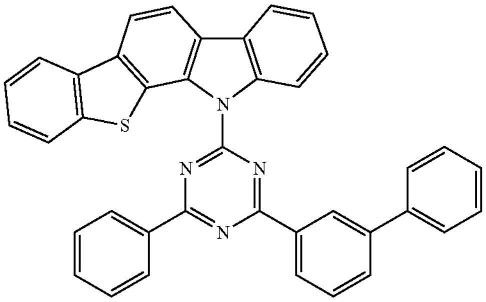
B-17
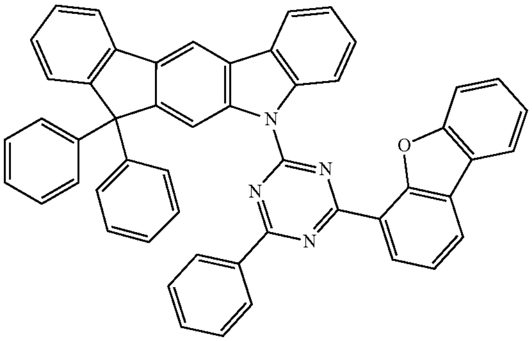
-continued
B-18
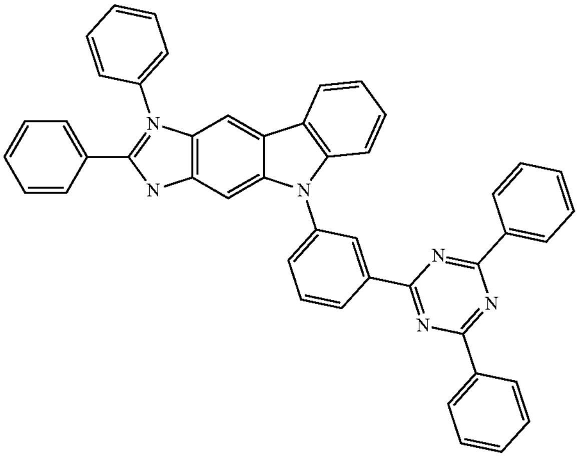
B-19
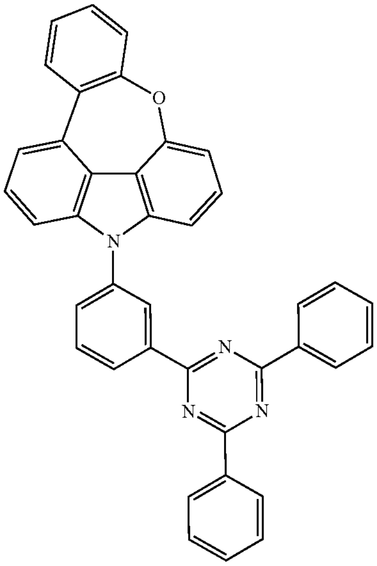
B-20
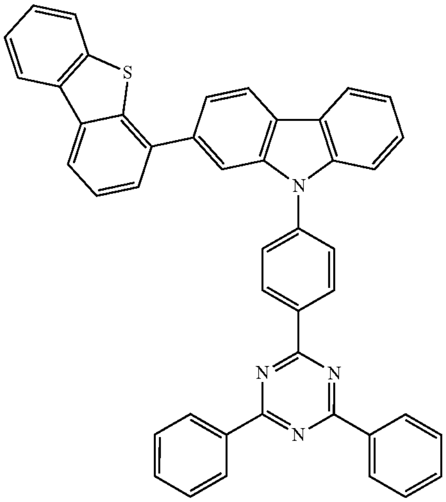

-continued
B-21
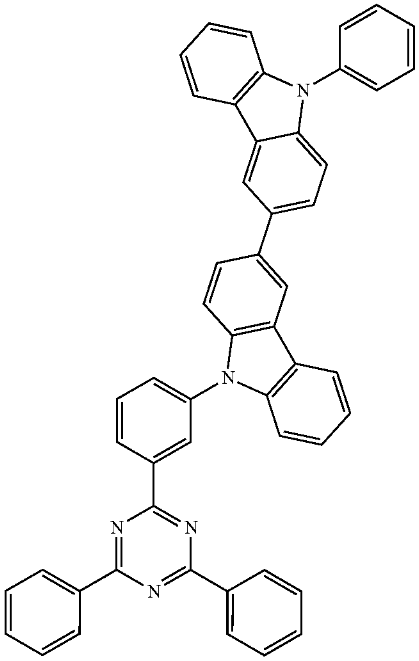
B-22
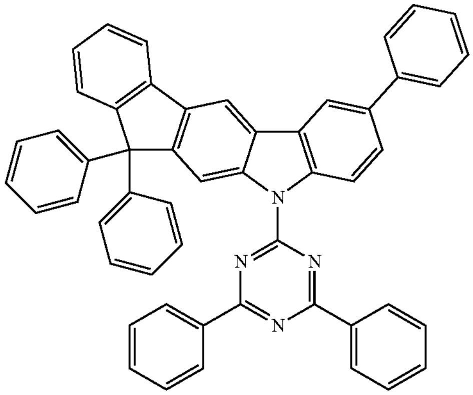
B-23
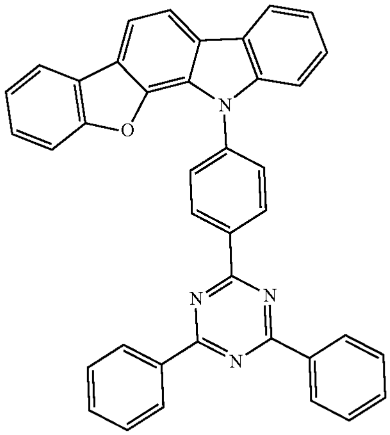
-continued
B-24
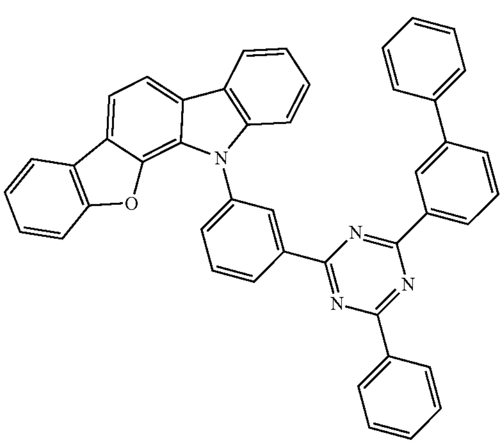
B-25
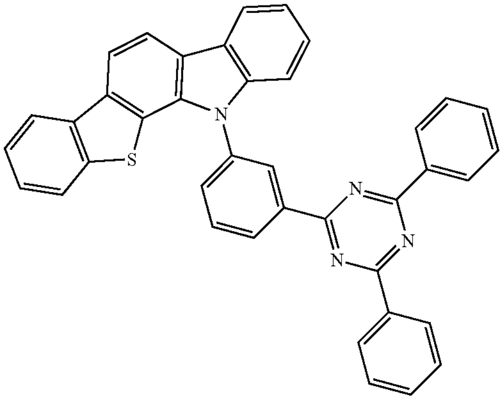
B-26
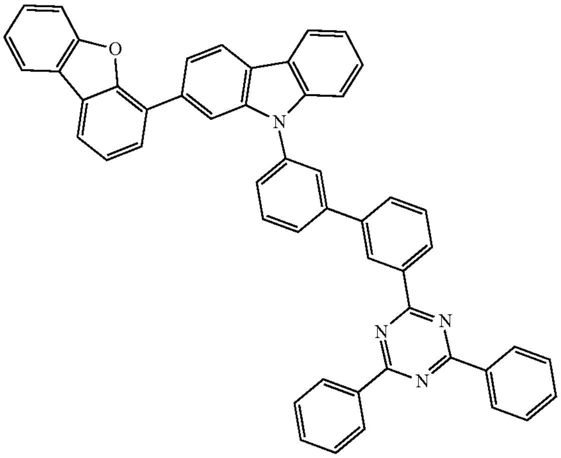

-continued
B-27
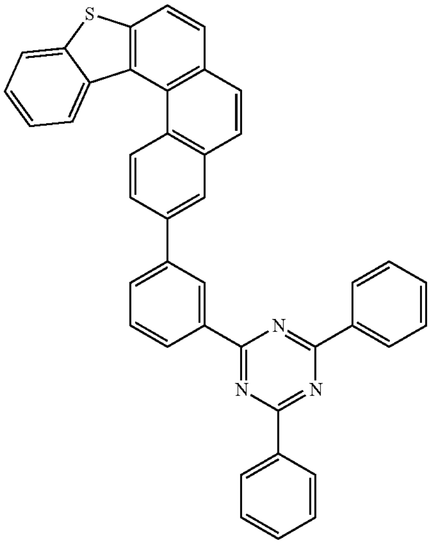
B-28
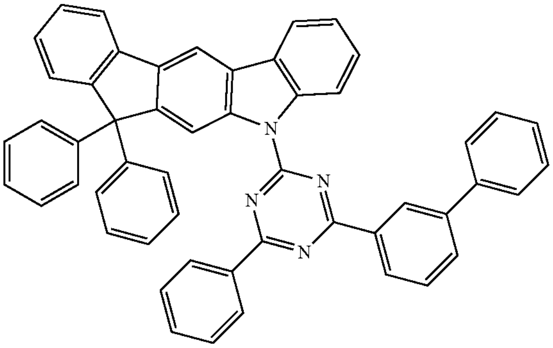
B-29
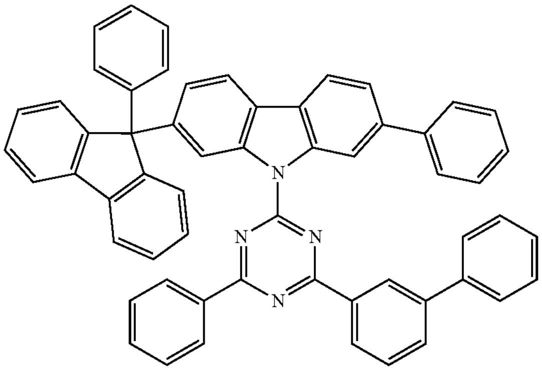
-continued
B-30
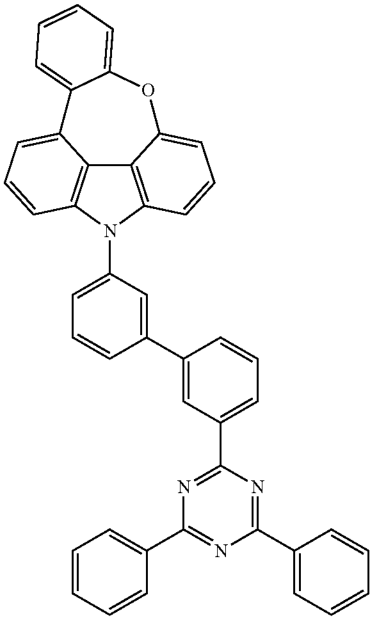
B-31
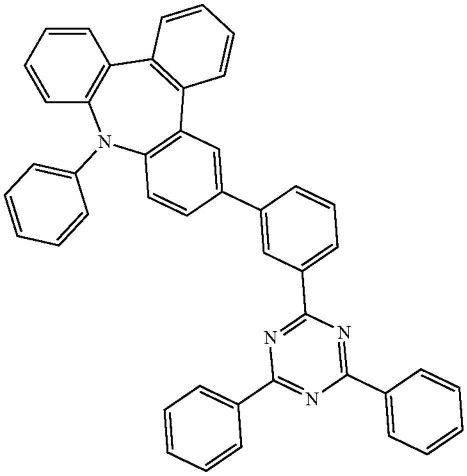
B-32
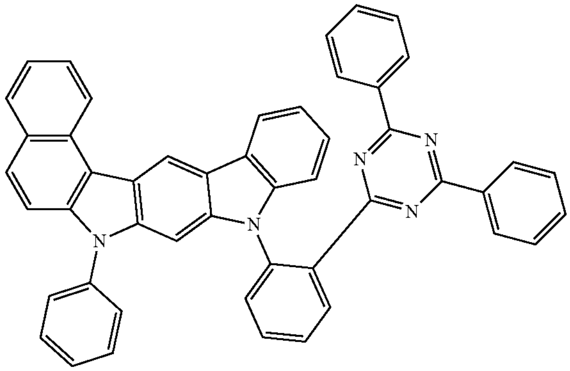

-continued
B-33
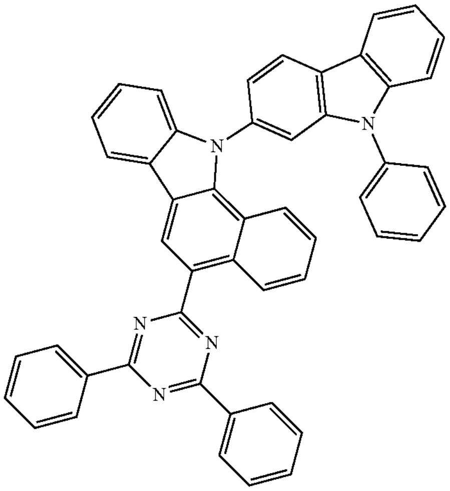
B-34
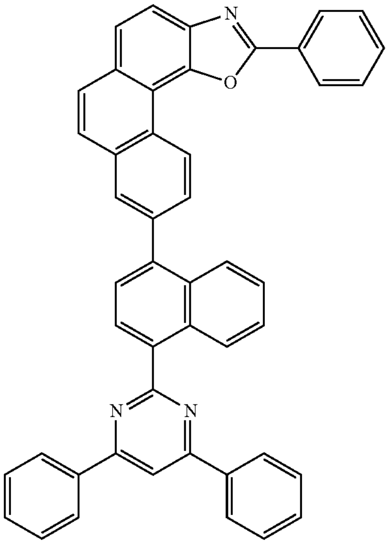
B-35
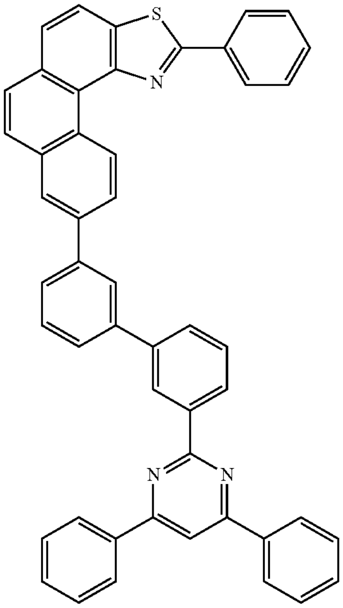
-continued
B-36
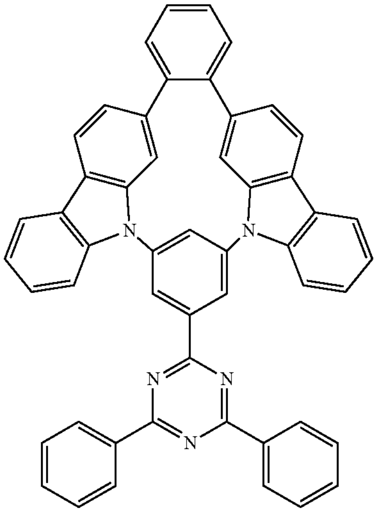
B-37
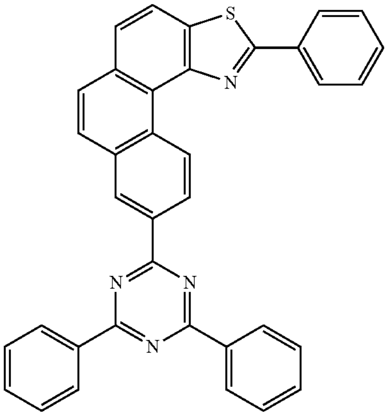
B-38
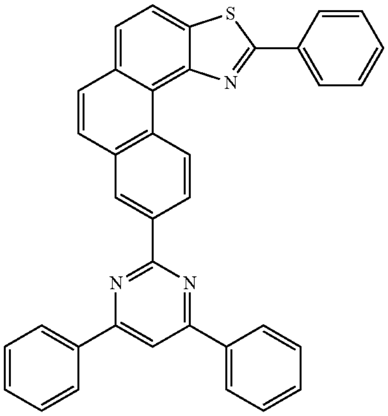

-continued
B-39
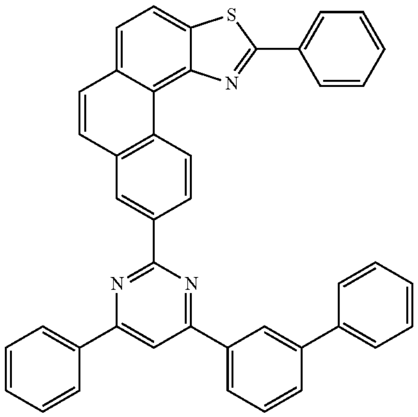
B-40
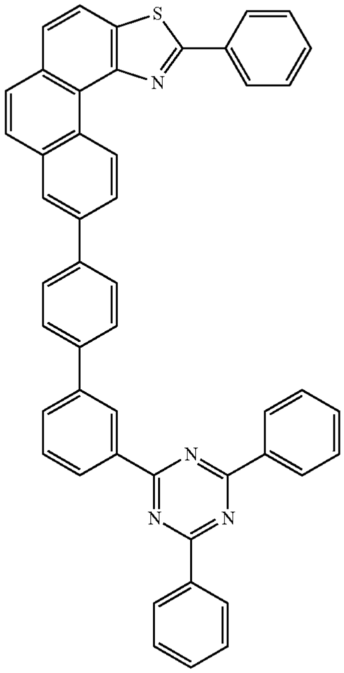
B-41
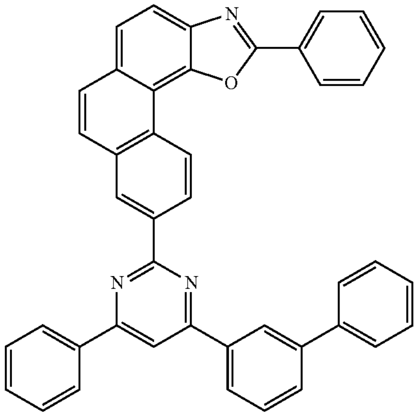
-continued
B-42
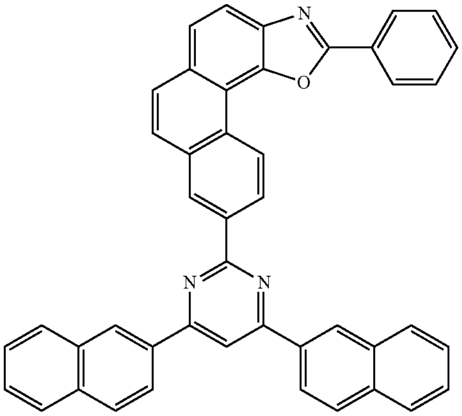
B-43
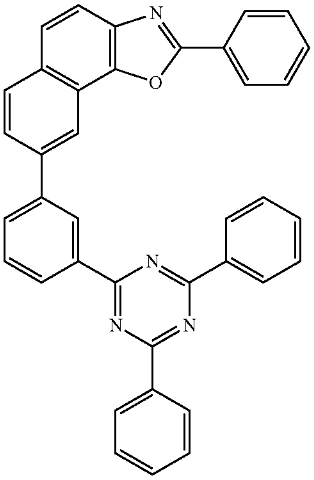
B-44
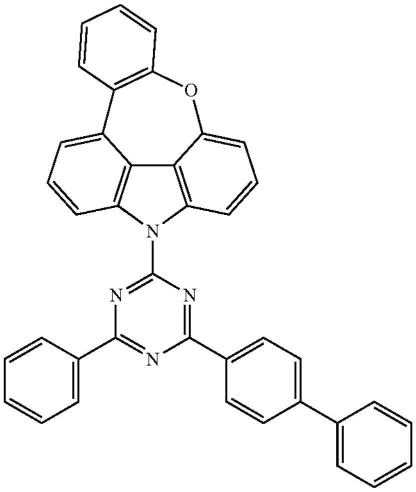

-continued
B-45
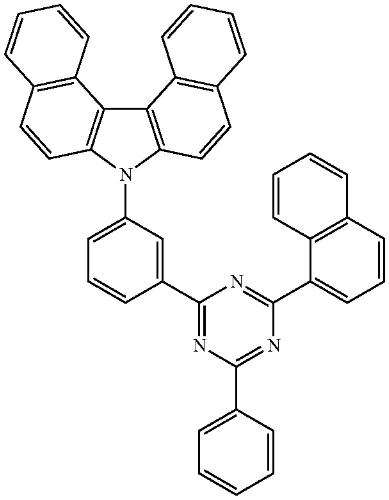
B-46
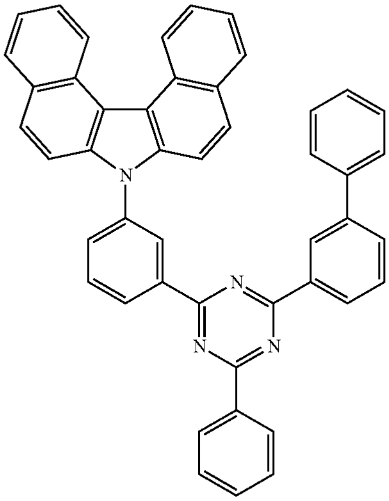
B-47
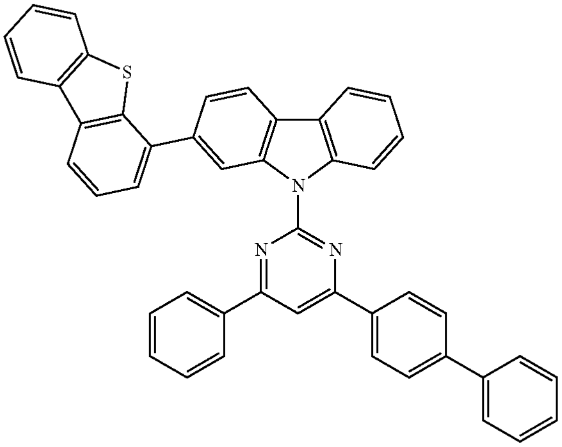
-continued
B-48
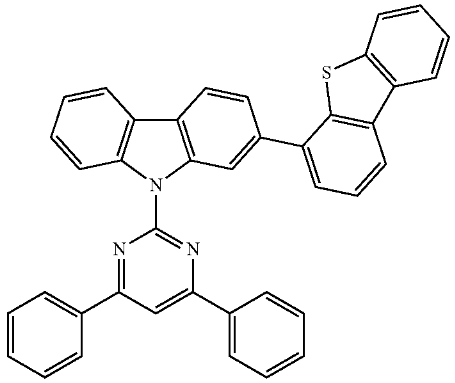
B-49
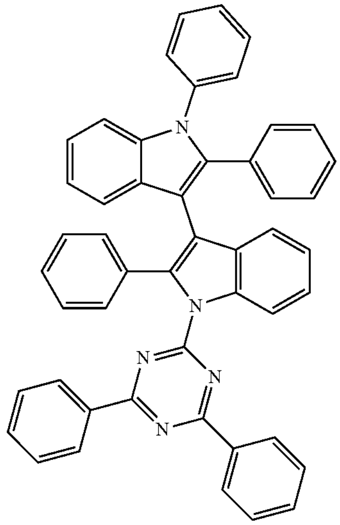
B-50
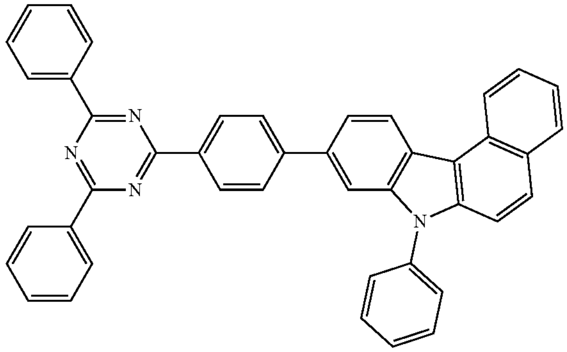

-continued
B-51
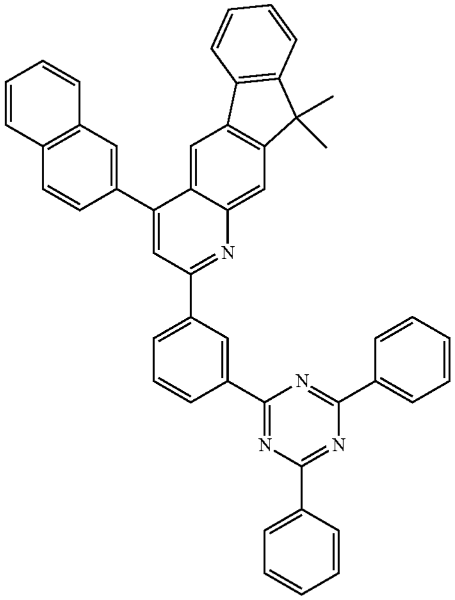
B-52
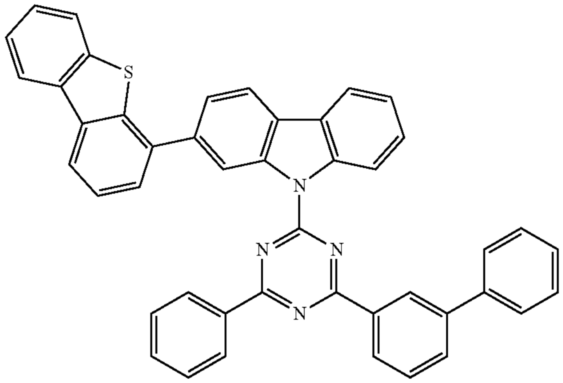
B-53
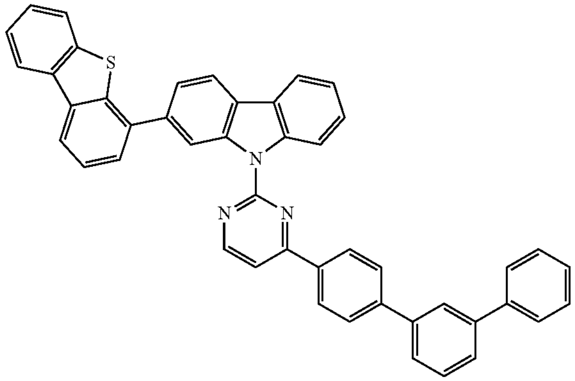
-continued
B-54
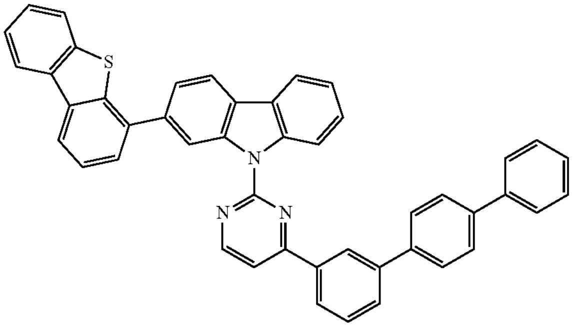
B-55
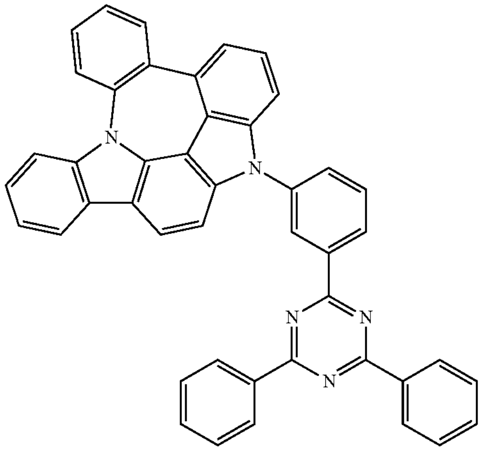
B-56
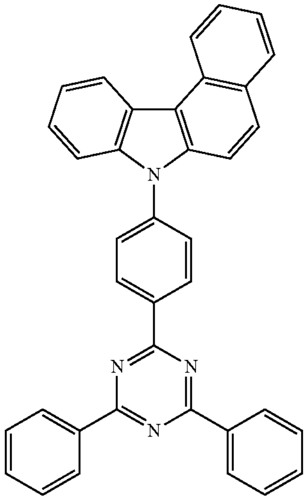

-continued
B-57
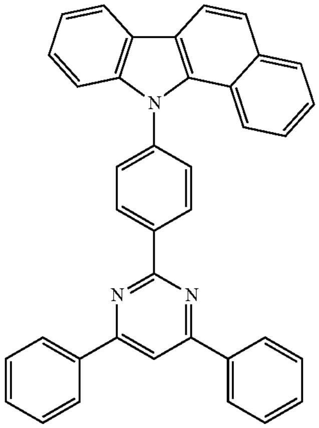
B-58
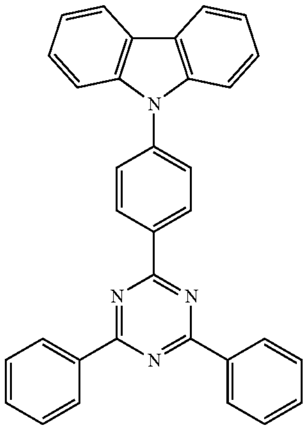
B-59
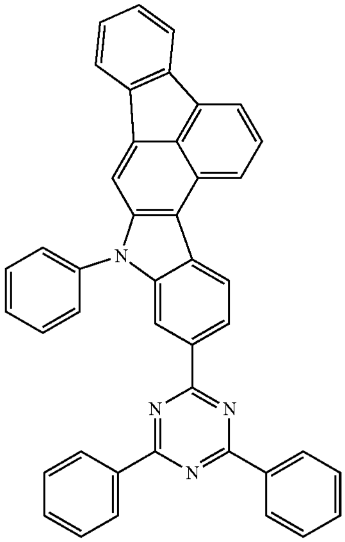
-continued
B-60
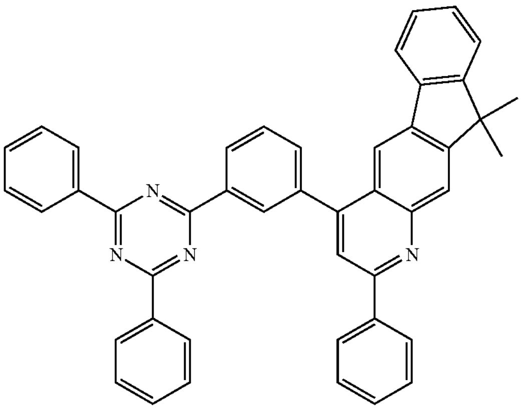
B-61
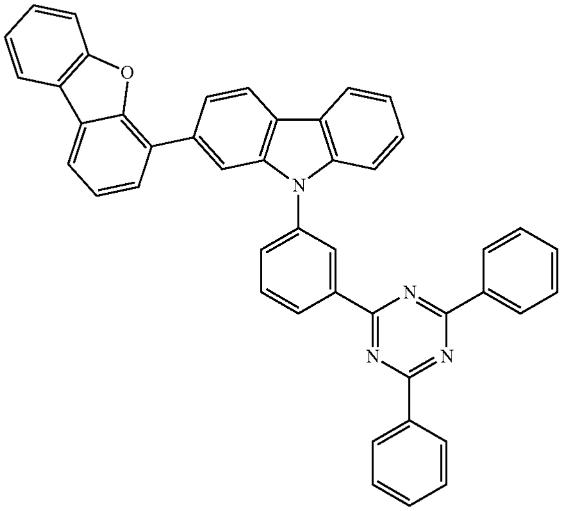
B-62
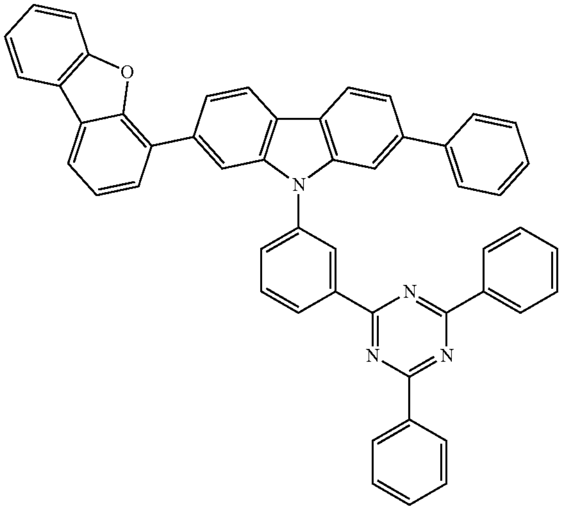

-continued
B-63
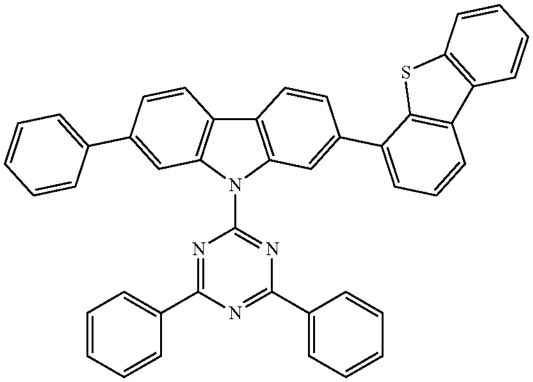
B-64
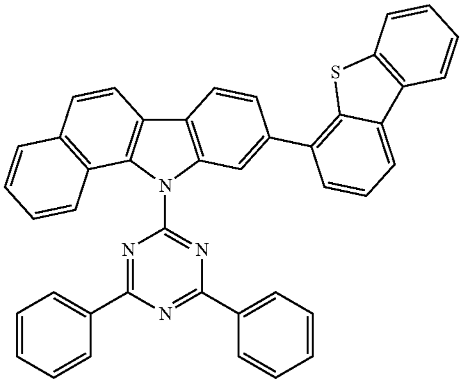
B-65
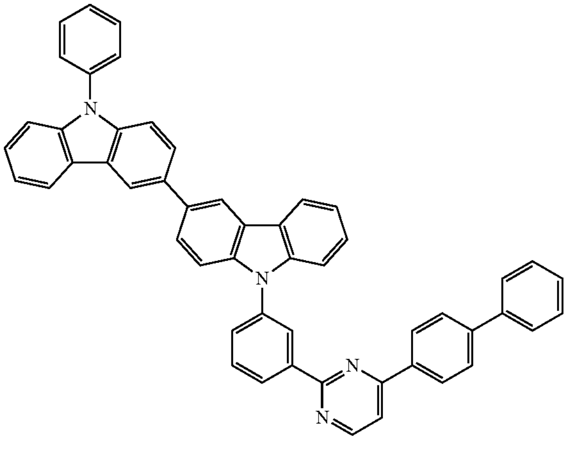
-continued
B-66
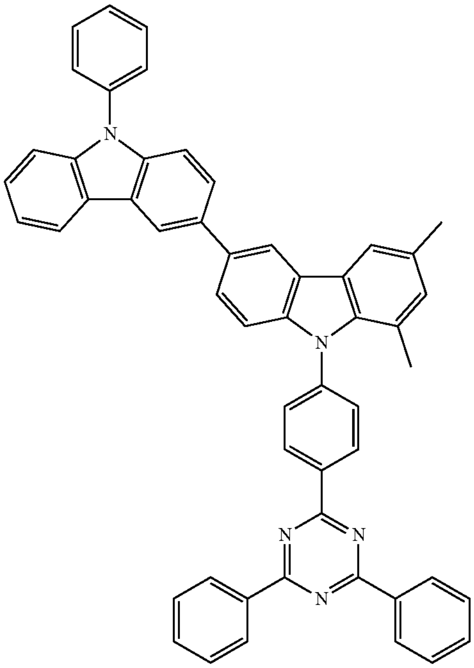
B-67
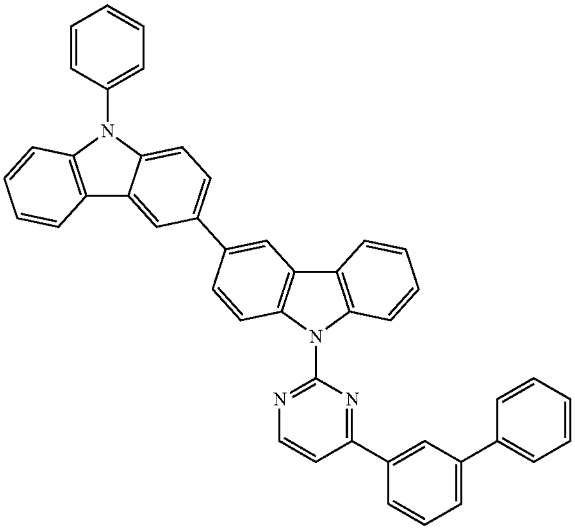

B-68
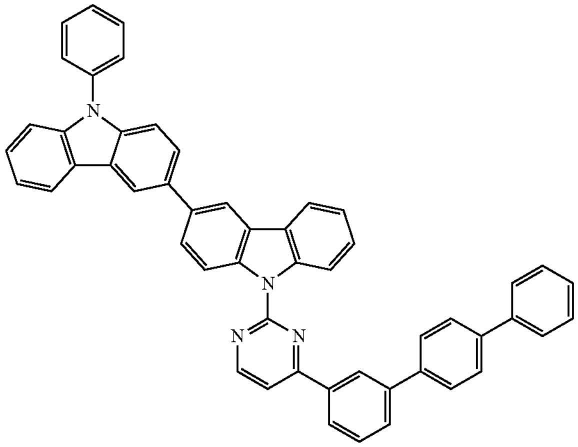
B-69
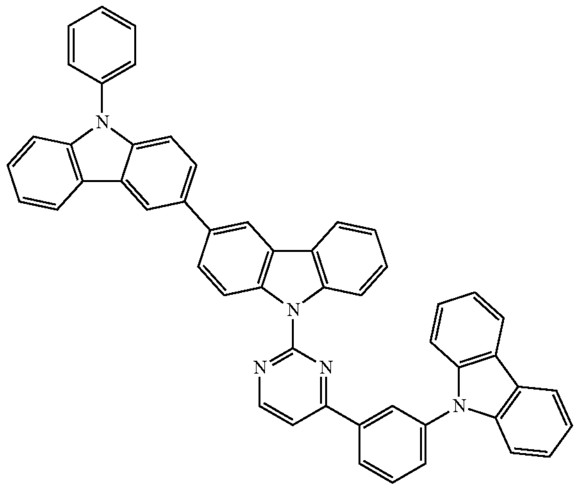
B-70
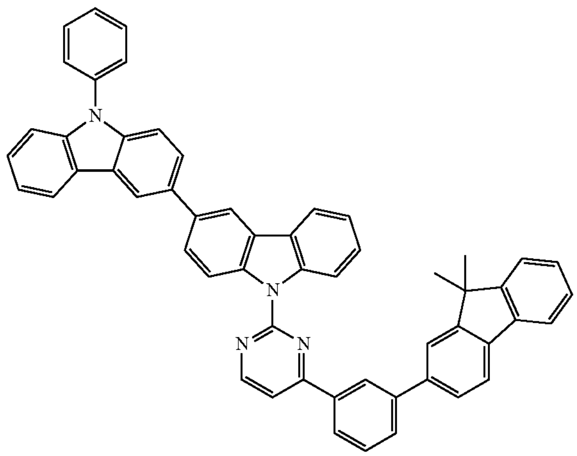
B-71
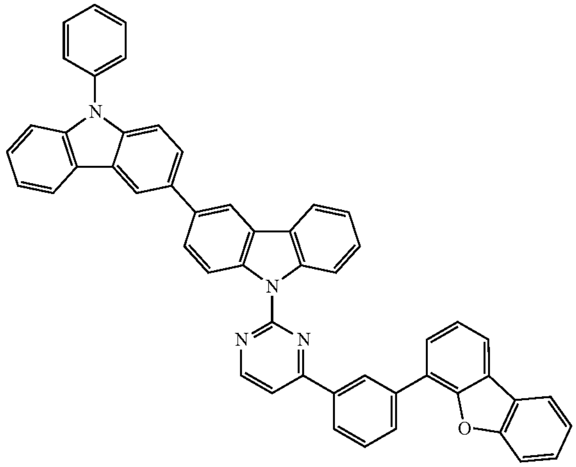
B-72
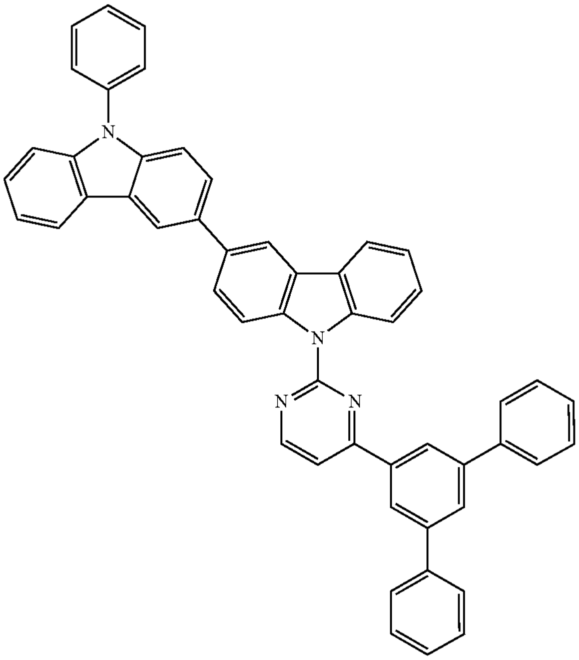
B-73
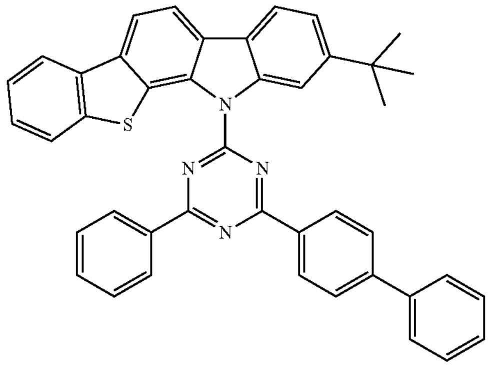

-continued
B-74
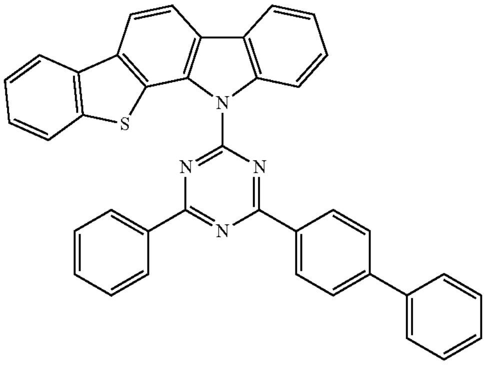
B-75
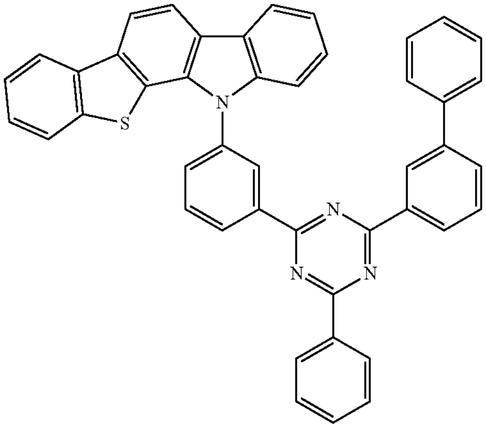
B-76
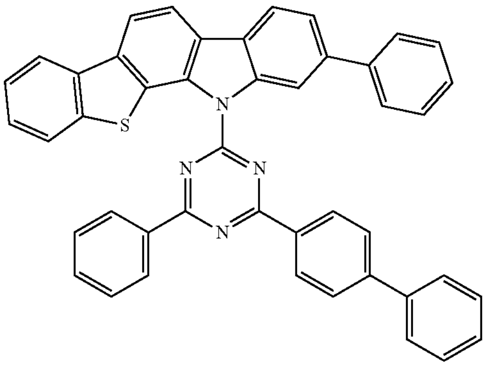
-continued
B-77
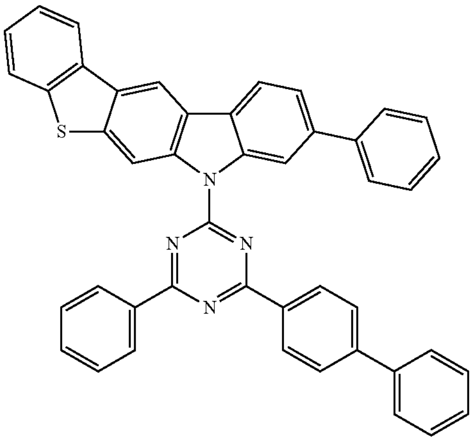
B-78
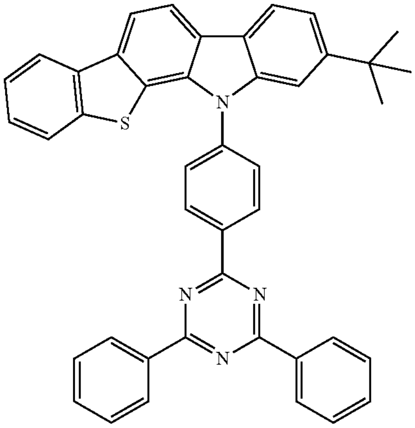
B-79
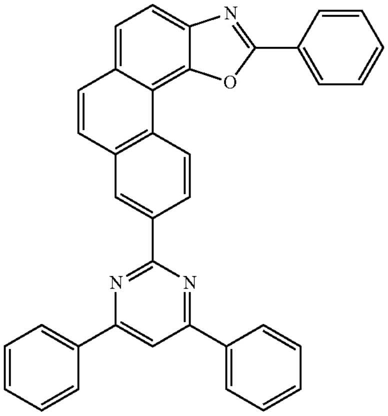

-continued
B-80
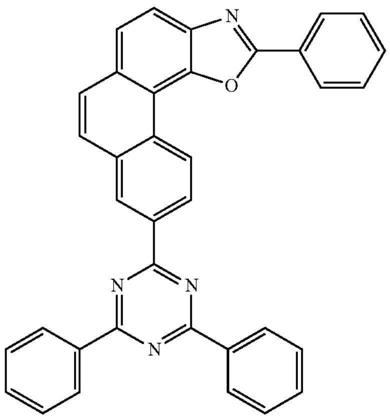
B-81
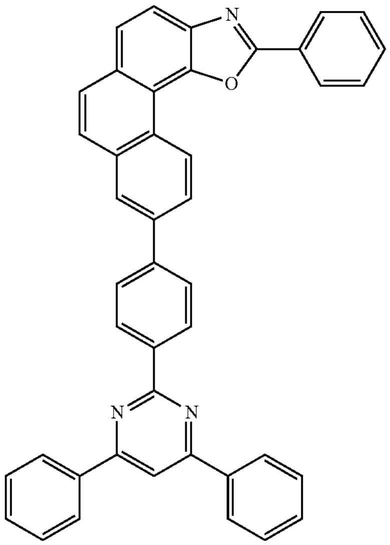
B-82
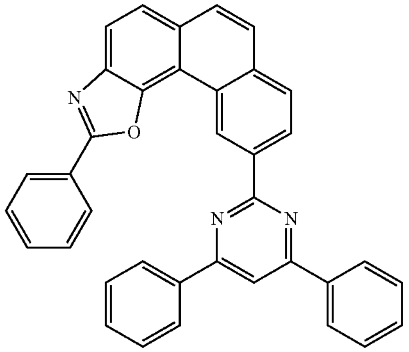
-continued
B-83
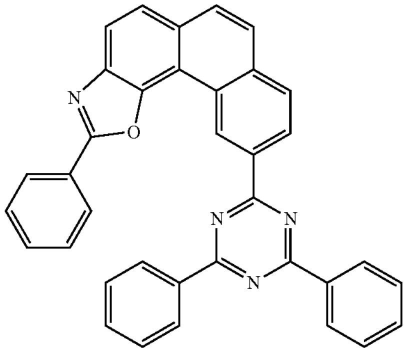
B-84
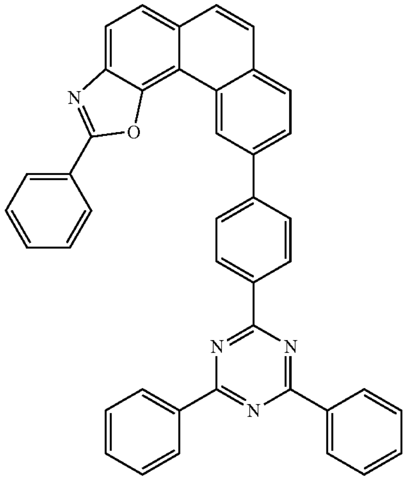
B-85
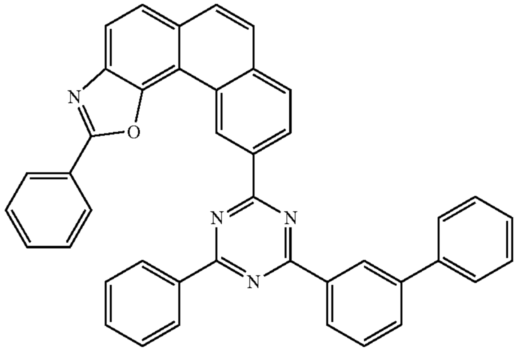

-continued
B-86
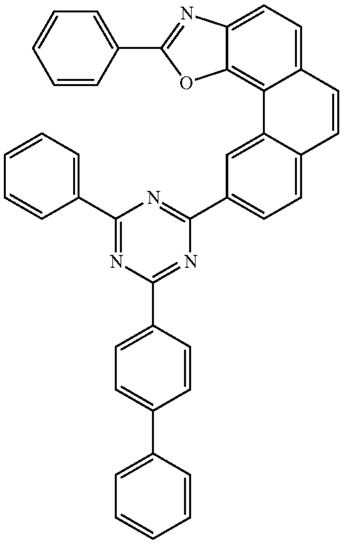
B-87
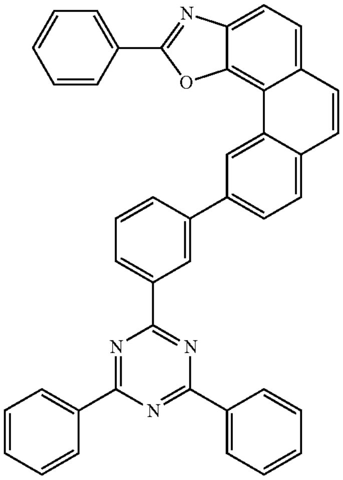
B-88
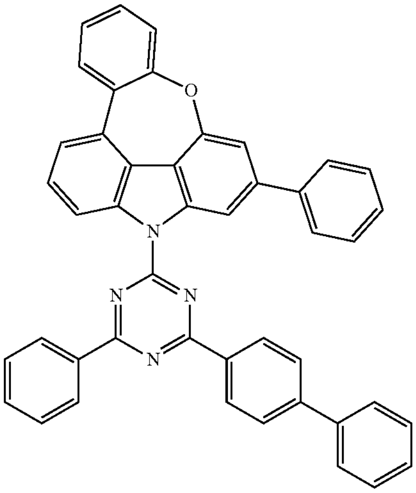
-continued
B-89
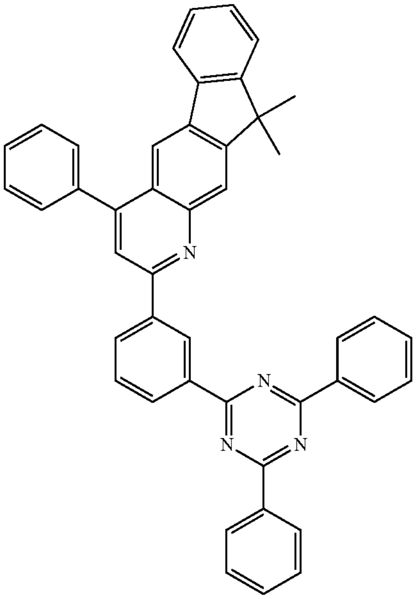
B-90
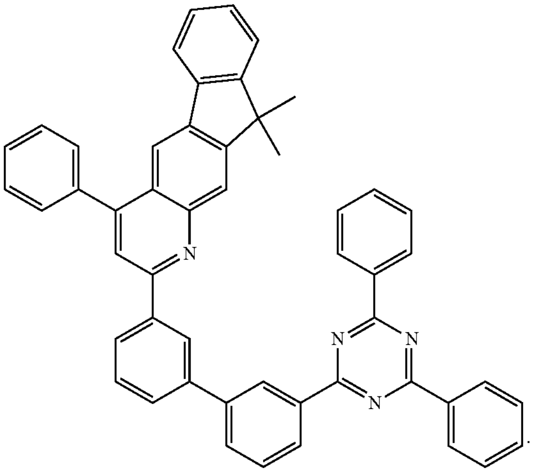
.
6. The organic electroluminescent device according to claim 1, wherein the compound represented by formula 2 is selected from the group consisting of:
C-1
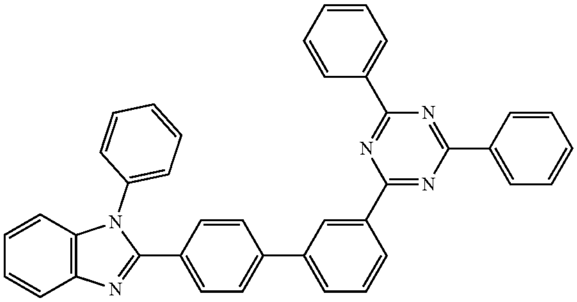

C-2
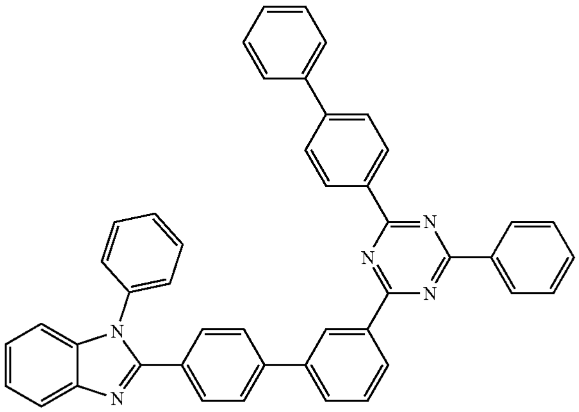
C-3
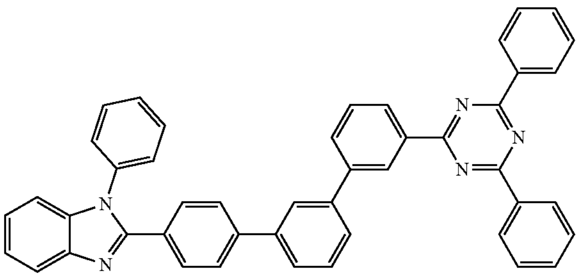
C-4
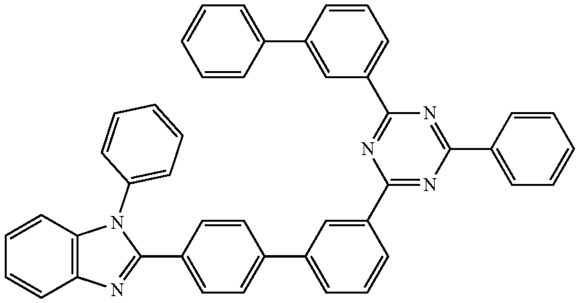
C-5
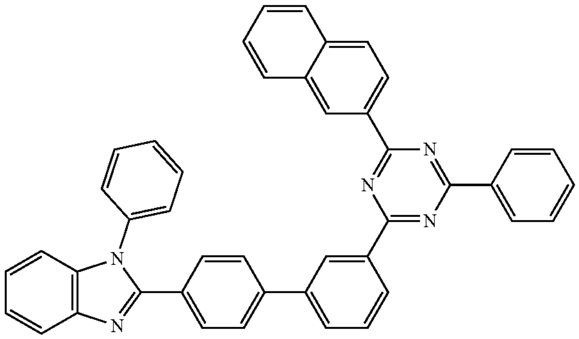
C-6
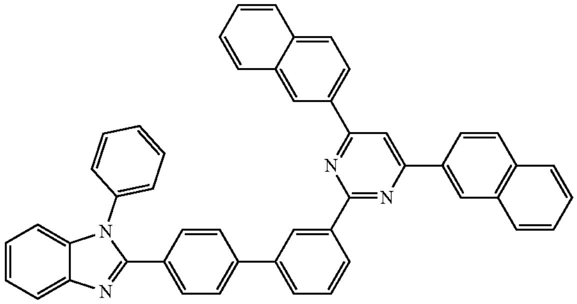
C-7
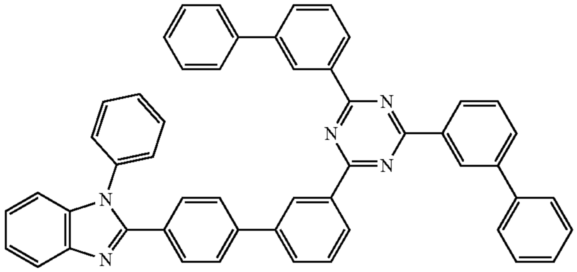
C-8
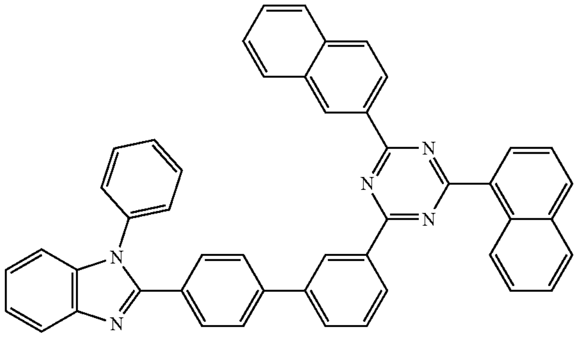
C-9
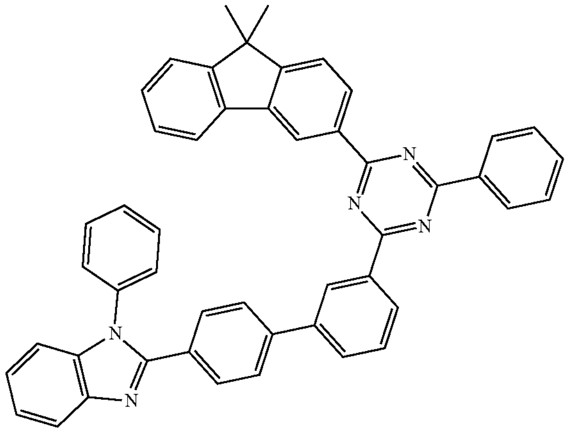

-continued
C-10
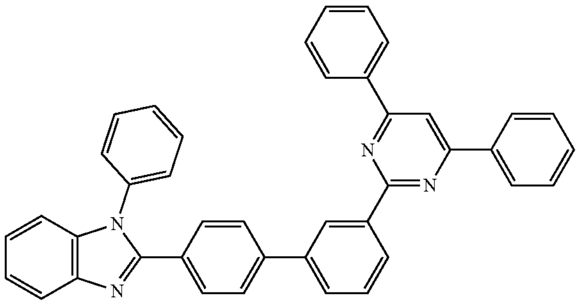
C-11
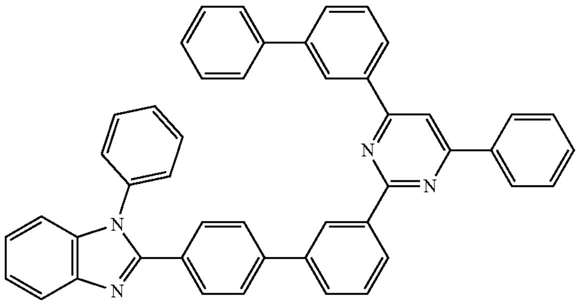
C-12
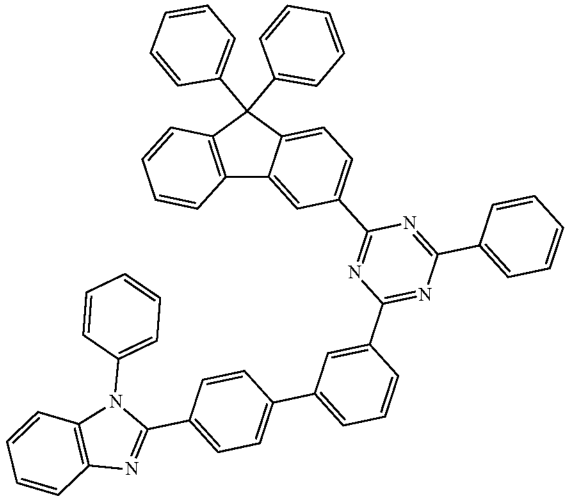
C-13
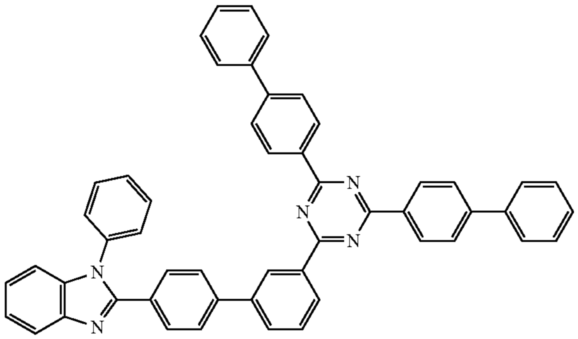
-continued
C-14
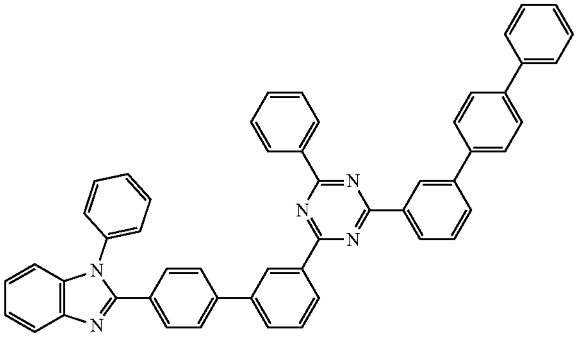
C-15
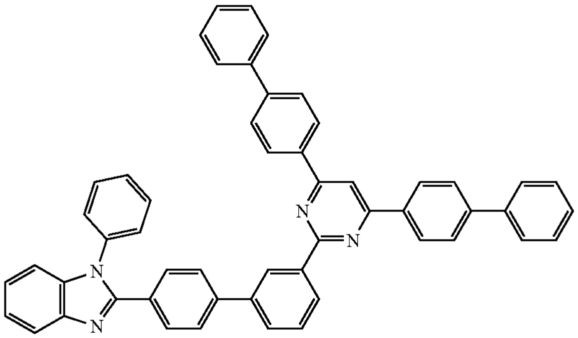
C-16
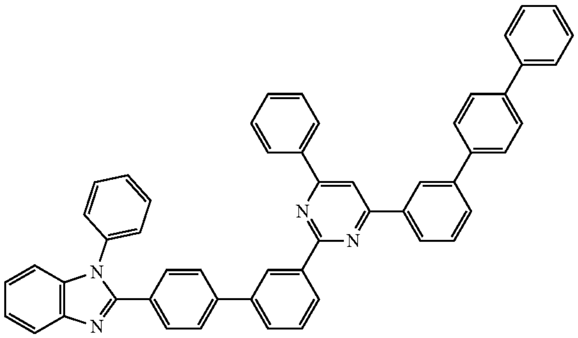
C-17
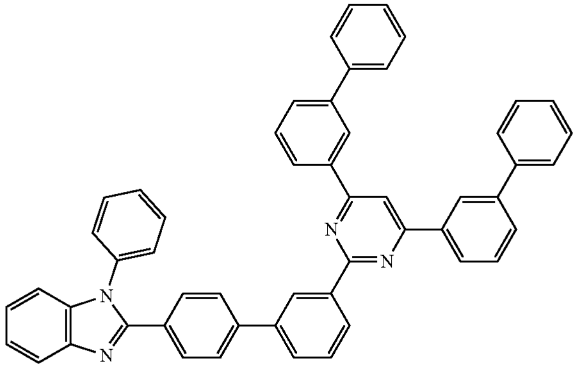

-continued
C-18
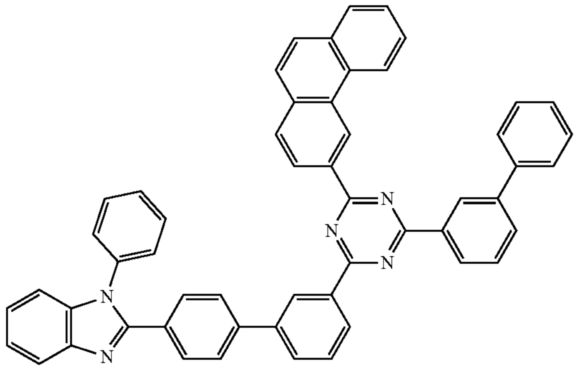
C-19
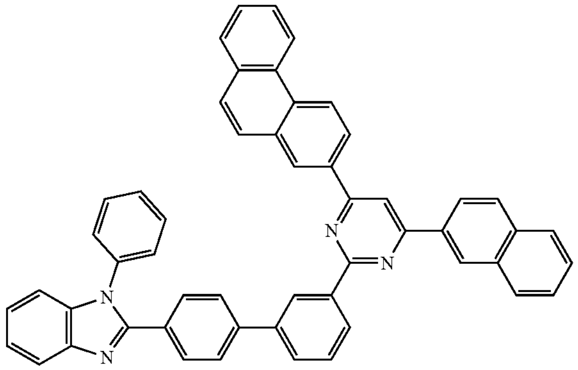
C-20
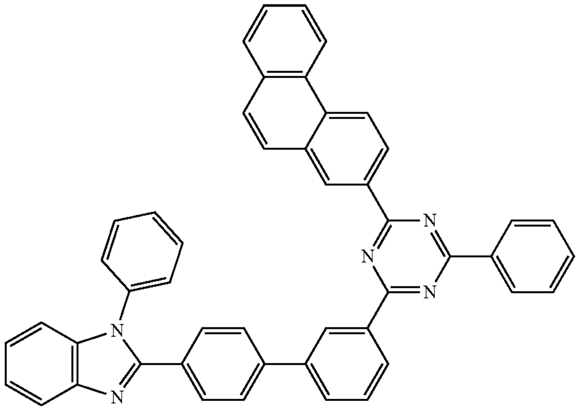
C-21
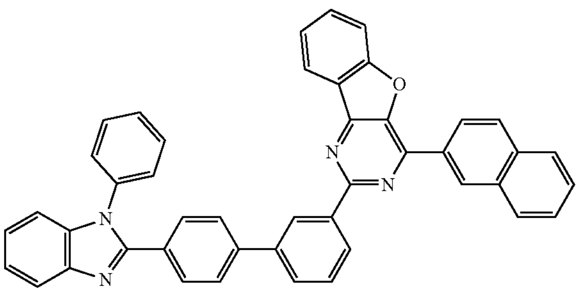
-continued
C-22
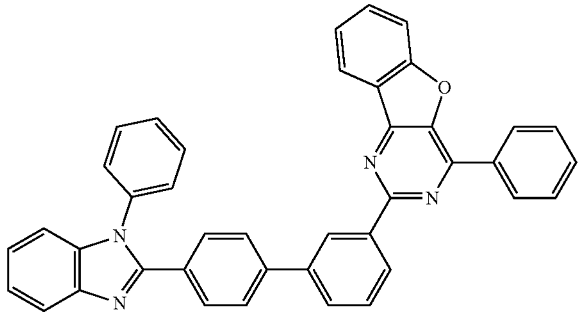
C-23
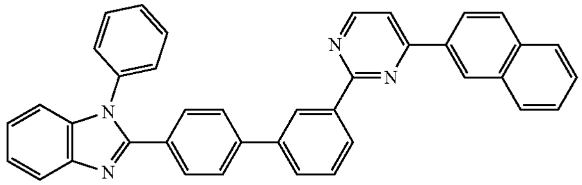
C-24
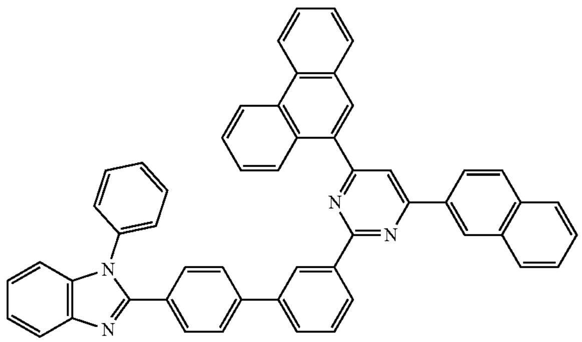
C-25
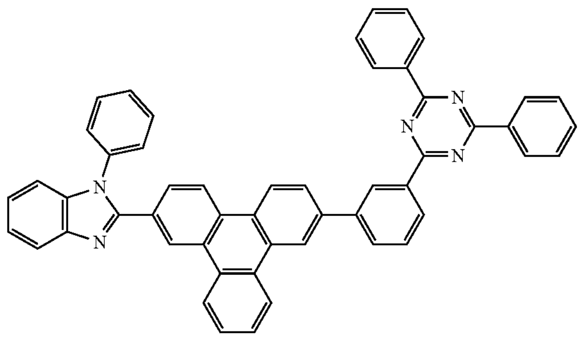

-continued

C-26

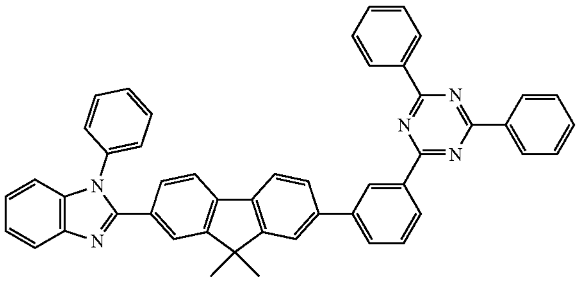

C-27

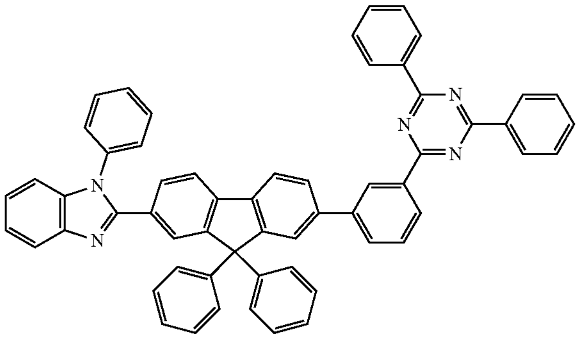

C-28

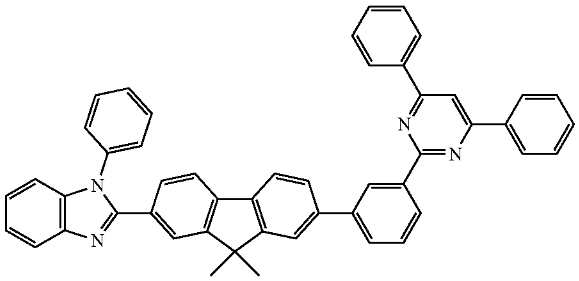

-continued

C-29

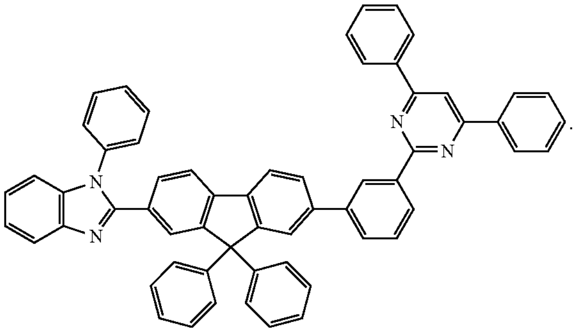

7. The organic electroluminescent device according to claim 1, wherein the light-emitting layer comprises a host compound and a dopant compound, the LUMO (lowest unoccupied molecular orbital) energy level of the electron buffer layer is higher than that of the host compound, and the LUMO energy level of the electron transport layer is higher than that of the electron buffer layer, with a proviso that the comparisons of the energy levels are based on absolute values.

8. The organic electroluminescent device according to claim 1, wherein the LUMO energy level of the electron transport layer (Ae) and the LUMO energy level of the host (Ah) satisfy the following equation:

$$Ae \leq Ah + 0.5 \text{ eV}$$

with a proviso that the comparison of the energy levels is based on absolute values.

9. The organic electroluminescent device according to claim 1, wherein the LUMO energy level of the electron transport layer (Ae) and the LUMO energy level of the electron buffer layer (Ab) satisfy the following equation:

$$Ae \leq Ab \pm 0.2 \text{ eV}$$

with a proviso that the comparison of the energy levels is based on absolute values.

10. A display system comprising the organic electroluminescent device according to claim 1.

* * * * *